(12) United States Patent
Coombe et al.

(10) Patent No.: US 8,209,131 B2
(45) Date of Patent: Jun. 26, 2012

(54) THERAPEUTIC HEPARINS AND THEIR BINDING TO INTERLEUKINS 4 AND 5 AND PECAM-1

(75) Inventors: Deirdre Roma Coombe, Wembly Downs (AU); Warren Charles Kett, Darlington (AU); Barbara Mulloy, London (GB)

(73) Assignee: Curtin University of Technology, Bentley, Western Australia (AU)

( * ) Notice: Subject to any disclaimer, the term of this patent is extended or adjusted under 35 U.S.C. 154(b) by 1137 days.

(21) Appl. No.: 11/587,335

(22) PCT Filed: Apr. 19, 2005

(86) PCT No.: PCT/AU2005/000551
§ 371 (c)(1),
(2), (4) Date: Aug. 29, 2007

(87) PCT Pub. No.: WO2005/100374
PCT Pub. Date: Oct. 27, 2005

(65) Prior Publication Data
US 2008/0146522 A1     Jun. 19, 2008

(30) Foreign Application Priority Data

Apr. 19, 2004  (AU) ................................ 2004902088
Jul. 8, 2004    (AU) ................................ 2004903765

(51) Int. Cl.
| G01N 31/00 | (2006.01) |
| G01N 33/48 | (2006.01) |
| G01N 33/53 | (2006.01) |
| G06G 7/58  | (2006.01) |

(52) U.S. Cl. ................ 702/27; 702/19; 703/11; 435/7.1
(58) Field of Classification Search ........................ None
See application file for complete search history.

(56) References Cited

OTHER PUBLICATIONS

Leveugle, B. et al "Heparin oligosaccharides that pass the blood-brain barrier . . . " J. Neurochem. (1998) vol. 70, No. 2, pp. 736-744.*
Chai, W. et al "Characterization of heparin oligosaccharide mixtures . . . " Anal. Chem. (1998) vol. 70, No. 10, pp. 2060-2066.*
Li et al. Mutants of Single Chain Interleukin 5 Show Asymmetric Recruitment of Receptor α and βc Subunits. Journal of Biological Chemistry, 271, 31729-31734.*
Graber at al. Identification of Key Charged Residues of Human Interleukin-5 in Receptor Binding and Cellular Activation . Journal of Biological Chemistry, 270, 15762-15769.*
Kitchen et al. Nature Reviews Drug Discovery, 3, 935-949, 2004.*
Tavernier et al. Proc. Natl. Acad. Sci. USA, vol. 92, pp. 5194-5198, 1995.*
Coombe, D.R. And Kett, W.C. 2005 "Heparan sulfate-protein interactions: therapeutic potential through structure-function insights" *Cell Mol Life Sci* 62(4):410-424.
Delisser, H.M. et al. 1993 "Platelet/endothelial cell adhesion molecule-1 (CD31)-mediated cellular aggregation involves cell surface glycosaminoglycans" *J Biol Chem* 268:16037-16046.
Lipscombe, R.J. et al. 1998 "Interleukin-5 binds to heparin/heparin sulfate. A model for an interaction with extracellular matrix" *J Leukocyte Biology* 63:342-350.
Lortat-Jacob, H. et al. 1997 "Human interleukin 4 is a glycosaminoglycan-binding protein" *Cytokine* 9:101-105.
Sun, Q.-H. et al. 1998 "Cell surface glycosaminoglycans do not serve as ligands for PECAM-1" *J Biol Chem* 273:11483-11490.
Sun, Q.-H. et al. 1996 "PECAM-1 is not a heparin-binding protein" *Molecular Biology of the Cell* 7:434A. Meeting Info: Annual meeting of the 6th International Congress on Cell Biology and the 36th American Society for Cell Biology. San Francisco, CA, USA. Dec. 7-11, 1996. Abstract No. 2525.
Watt, S.M. et al. 1993 "The heparin binding PECAM-1 adhesion molecule is expressed by CD34+ hematopoietic precursor cells with early myeloid and B-Iymphoid cell phenotypes" *Blood* 82:2649-2663.

* cited by examiner

Primary Examiner — Michael Borin
(74) Attorney, Agent, or Firm — Knobbe Martens Olson & Bear LLP

(57) ABSTRACT

The present invention relates generally to chemical agents useful in the prophylaxis and/or treatment of disease conditions and in particular chronic disease conditions such as inflammatory including allergic diseases, metastatic cancers and infection by pathogenic agents including bacteria, viruses or parasites. More particularly, the chemical agents contemplated by the present invention are selected from glycosaminoglycan (GAG) molecules derived from a larger GAG, GAG-like molecules which resemble GAGs in some of their characteristics but may be derived from a larger non-GAG polysaccharide and molecules having a GAG-like composite structure as well as agents which bind to the same sites as GAGs, GAG-like molecules or GAG-like composite molecules. The present invention also provides assays to identify GAG and GAG-like therapeutic agents including GAG-like composite structures as well as analogs, homologs and orthologs thereof.

1 Claim, 30 Drawing Sheets

*E.coli* K5 capsular polysaccharide non-sulfated heparin backbone polysaccharide

IL-5 binding to heparin is inhibited by heparan sulfate modified with 3-OST-3

Response Units

- IL5 WT - 100nM (0 HS)
- IL5 WT - 100nM (5 ST3)
- IL5 WT - 100nM (10 ST3)
- IL5 WT - 100nM (20 ST3)

Time (seconds)

Figure 27

Response Units

IL-5 binding is inhibited by 10ug/ml of DP12 fragments modified by 3-OST-3

— IL5 WT (200nM) - 0 DP12
— - IL5 WT (200nM) - 10 DP12
— IL5 WT (200nM) - 10 ST3

Time (seconds)

Figure 28

THERAPEUTIC HEPARINS AND THEIR BINDING TO INTERLEUKINS 4 AND 5 AND PECAM-1

BACKGROUND OF THE INVENTION

1. Field of the Invention

The present invention relates generally to chemical agents useful in the prophylaxis and/or treatment of disease conditions and in particular chronic disease conditions such as inflammatory including allergic diseases, metastatic cancers and infection by pathogenic agents including bacteria, viruses or parasites. More particularly, the chemical agents contemplated by the present invention are selected from glycosaminoglycan (GAG) molecules derived from a larger GAG, GAG-like molecules which resemble GAGs in some of their characteristics but may be derived from a larger non-GAG polysaccharide and molecules having a GAG-like composite structure as well as agents which bind to the same sites as GAGs, GAG-like molecules or GAG-like composite molecules. The present invention also provides assays to identify GAG and GAG-like therapeutic agents including GAG-like composite structures as well as analogs, homologs and orthologs thereof.

2. Description of the Prior Art

Bibliographic details of the publications referred to by author in this specification are collected at the end of the description.

Reference to any prior art in this specification is not, and should not be taken as, an acknowledgment or any form of suggestion that this prior art forms part of the common general knowledge in any country.

The development of many disease conditions in a host involves the interaction between cell or viral entities or molecules produced thereby and cells in the particular host. One well studied interaction is between HIV, gp120 and lymphocyte CD4 receptors [Eckert and Kim, *Annu. Rev. Biochem.* 70: 777-810, 2001]. Despite some success, however, in antagonizing or facilitating these interactions, it has been difficult to identify an antagonist that exhibits a sufficiently broad spectrum of activity.

In work leading up to the present invention, the inventors investigated heparin-like glycosaminoglycans (HLGAGs) such as heparin and heparan sulfate and the oligosaccharides derived from them. Glycosaminoglycans (GAGs) are ubiquitous and play pivotal roles in many of the inflammatory processes within the human body. These large molecular weight polysaccharides contribute to such processes as cancer metastasis, arthritis, transplant rejection, allergic rhinitis and asthma and thus a greater understanding of these processes leads to improved drugs for the treatment of such conditions. Currently, one of the best known GAGs is the heparin family of sulfated polysaccharides and the anti-coagulant activity of these molecules is well understood.

However, HLGAGs are a heterogenous group of molecules [Conrad, *Heparin binding proteins*. Academic Press, San Diego, 1998; Lander and Selleck, *J. Cell Biol.* 148(2): 227-232, 2000]. Heparin and heparan sulfate, like all HLGAGs, are long linear polysaccharides [Sasisekharan and Venkataraman, *Curr. Opin. Cliem. Biol.* 4(6): 626-631, 2000; Casu, *Ann. N.Y. Acad. Sci.* 556: 1-17, 1989; Casu, *Adv. Carbohydr. Chem. Biochem.* 43: 51-134, 1985]. They are synthesized as non-sulfated chains of repeating disaccharide units comprising glucuronic acid (GlcA) and glucosamine (GlcN) which, in the golgi, are modified at various sites along their length. Heparin is more extensively modified than heparan sulfate and most of the GlcN units are modified by a sulfate group to become N-sulfated GlcN and most GlcA units are converted to iduronic acid (IdoA) through the action of epimerase. HLGAGs are heterogenous since modifications to the sulfate chains are often incomplete. The result is extensive regions of intermediate modification.

Thus, for example, heparan sulfate chains consist of highly sulfated, structurally flexible domains rich in 2-O-sulfated IdoA alternating with regions of low sulfation consisting predominantly of N-acetyl GlcN and GlcA, which are a rigid structure.

The sulfation patterns of HLGAGs are complex especially with respect to the positioning of 6-O-sulfates. Consequently, not all HLGAG molecules are identical. Similarly, not all molecules in a preparation of HLGAGs from a particular cell or tissue are identical; rather such preparations represent a family of molecules.

It is the sulfation pattern which largely determines the protein binding characteristics of a particular HLGAG. Some proteins bind only to particular structural motifs within a HLGAG chain and conversely some GAGs bind only to particular sites or regions on a protein. Anti-thrombin III, for example, binds to a unique pentasaccharide sequence displaying a particular arrangement of sulfate groups and the heparin pentasaccharide binds to a specific site on the anti-thrombin III protein [Whisstock et al., *J. Mol. Biol.* 301: 1287-1305, 2000]. Basic fibroblast-derived growth factor (FGF-2) and hepatocyte growth factor (HGF) both bind heparin, but the heparin structures that are essential for binding are quite different for each and are different from that required by anti-thrombin III [Maccarana et al., *J. Biol. Chem.* 268 (32): 23898-23905, 1993; Lyon et al., *J. Biol. Chem.* 269: 11216-11223, 1994]. Moreover, heparin has been shown to bind to a particular region on FGF-2 [Faham et al., *Science* 271: 1116-1120, 1996]. The binding of sulfated GAGs and proteins in the anti-coagulation cascade is very complex and the interaction of heparin with platelet factor IV (PF-IV) is something that has been problematic in some therapeutic applications. Elegant work has shown that, although the heparin-PF-IV is an extremely high affinity interaction, the specificity is also high, thus by adding functionality that is non-detrimental to heparin binding and yet detrimental to PF-IV binding, some selectivity may be achieved (Petitou et al., *Nature* 398: 417, 1999.) This was achieved by minimizing the number of highly sulfated regions to 4-5 saccharide units on the termini and having a non-charged oligosaccharide spacer separating the charged sections.

FGF-2 recognizes a motif containing a single IdoA 2-O-sulfate in a defined position, whereas for HGF, the positioning of the GlcN 6-O-sulfate groups are critical. Some heparin molecules within a preparation will carry both the anti-thrombin III binding pentasaccharide and the FGF-2 binding motif, whereas others will carry the HGF binding motif and the FGF-2 motif and not the anti-thrombin III binding pentasaccharide. Indeed, on average only one third of the molecules within a preparation of heparin carry the anti-thrombin III binding pentasaccharide [Conrad, 1998, Supra].

Thus, the molecules in a preparation of HLGAGs differ in the order, in the number, and in the types of protein binding sites. The challenge is to identify, in structural terms, the HLGAG motif that binds the protein of interest and the HLGAG binding site on the protein. The isolation and purification of that HLGAG motif should give a reagent that is potent and more specific in its binding behaviour. Once the carbohydrate structure of the motif is known, it is then possible to make structural analogs or orthologs (i.e. functionally equivalent structures) that may or may not contain GAGs as part of their structure and which can be clinically used.

The heterogeneity present in the heparin isolated from natural sources (mast cells of pigs) gives rise to many side effects. The search for a GAG, or a structural analogue, without, or with reduced anti-coagulant activity could pave the way for more effective treatments of the inflammatory conditions outlined above.

Sources of GAG polysaccharides include from natural sources, as well as synthetic or semi-synthetic sources.

Many "natural" type glycosidic linkages predominate as a function of various enzymatic systems that are responsible for the biosynthesis of these oligosaccharides. Accessing quantities of these complex oligosaccharides from natural sources necessitates repeated purification by chromatography and due to the similarity of many of these oligosaccharides, homogeneous samples are difficult to obtain.

The capsular polysaccharide from E. coli K5 is composed of an alternate α-N-acetyl glucosamine (α-GlcNAc) and β-glucuronic acid (β-GlcA) units and contains no sulfate or other charged groups (see FIG. 17). The heparin backbone consists of the following motif α-GlcNAc, β-GlcA, α-GlcNAc, β-iduronic acid (β-IdoA) with varying degrees of sulfation. The only difference between GlcA and IdoA is the configuration of the carboxylic acid group at C-5, thus the heparin backbone and the E. coli K5 backbone are extremely similar in structure (FIG. 17). Indeed the K5 polysaccharide displays very low immunogenicity. Escherichia coli K5 is capable of producing approximately 50 mg/L from a growth medium and thus is ideally suited for the multi-gram production of the desired heparin-like backbone.

Suitable strains of E. coli for the production of K5 polysaccharide are NCDC Bi 626-42 and NCDC Bi 8337-41 and both are available from the American Type Culture Collection (ATCC). A number of publications describe isolation of the K5 polysaccharide. See, for example, Leali et al., *J. Biol. Chem.* 276: 37900-37908, 2001; and Finke et al., *J. Bacteriol.* 173: 4088-4094, 1991. Briefly, a medium rich in glycerol in preference to glucose is used to grow the bacteria. Conditioned media is collected from late logarithmic phase cultures and concentrated using a 10,000 Da cut-off ultrafiltration membrane. The polysaccharide is recovered by acetone precipitation, any proteins are digested with protease II and ultrafiltration and precipitation is used to recover the polysaccharide. Some methods also suggest an anion exchange chromatography step (U.S. Pat. No. 5,341,876).

In accordance with the present invention, GAG and GAG-like molecules including GAG-like composite molecules are identified which interact with target ligands such as cytokines or growth factors. Such molecules, including their chemical analogs, homologs and orthologs, are proposed to have useful therapeutic or diagnostic properties.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The present invention is predicated in part on the identification of chemical agents which inhibit interaction between a cell surface HLGAG and a cell-free or cell-associated ligand, or an extracellular HLGAG and a cell-associated ligand or which inhibit interaction between an extracellular HLGAG and a cell-free ligand. Conveniently, the chemical agents are cell-free GAG molecules including a family of cell-free GAG molecules or GAG-like molecules or their "functional" analogs, homologs or orthologs. By "functional" in this context means that the entity exhibits a binding property of the parent GAG molecule or exhibits an antagonistic property against the parent GAG. A GAG-like molecule includes a GAG-like composite structure having GAG or GAG-like components and non-GAG components. The GAG or GAG-like molecules or GAG-like composite molecules may be derived from naturally occurring HLGAGs or may be obtained by a process of chemical modification of a non-GAG polysaccharide or may be a composite structure which may only in part comprise a saccharide backbone.

These GAG or GAG-like oligosaccharides or GAG-like composite molecules are generally regarded as semi-synthetic and are generated from large polymeric polysaccharides. The semi-synthetic oligosaccharides may have varying degrees of charged species, for example sulfates and/or phosphates. In addition, compounds may undergo a number of other modifications including modifications such as the addition of side branches and phosphorylation of the GAG oligosaccharides. A library can also be made of the composite structures. In this case there will be differences in the length of the negatively charged units that resemble GAGs, differences in the length and composition of the linker that connects the negatively charged regions that resemble GAGs and differences in the angles and flexibility of the linker. Means for screening the library are disclosed by determining which GAG oligosaccharides, or GAG-like oligosaccharides (which may or may not be branched), or composite structures act as ligands for proteins and other molecules involved in disease situations. The identification of these fractions then permits the development of a range of antagonists or agonists to modulate the interaction. It is proposed that these molecules are useful in the prophylaxis and/or treatment of disease conditions such as but not limited to inflammatory conditions, metastatic cancers, allergic conditions like allergic rhinitis and asthma and diseases including infection by bacterial, viral or parasitic agents. Disease conditions include infection by HIV, SARS virus and influenza.

Accordingly, one aspect of the invention is directed to a GAG oligosaccharide having the formula:—

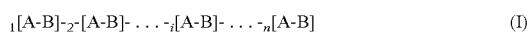

$$_1[A-B]-_2-[A-B]-\ldots-_i[A-B]-\ldots-_n[A-B] \quad (I)$$

or a GAG-like oligosaccharide, GAG-like composite or chemical analog, homolog or ortholog of the GAG oligosaccharide of Formula (I);

wherein:

A is an oligosaccharide, disaccharide or monosaccharide monomer unit comprising a saccharide such as, but not limited to, glucuronic acid, iduronic acid, glucosamine, mannose, mannan, dextran, glucose, fructose, sucrose, heptulose, pentose or sulfated forms thereof;

B may be the same as A or is a monomer unit comprising a glucosamine residue, a glucosamine derivative and/or a sulfated and/or a phosphorylated form thereof and/or acetylated form thereof or alkyl ether derivatives comprising methyl, ethyl, propyl or butyl;

wherein the monomer units, A and B, are linked by glycosidic bonds;

$_i[A-B]$ is the same or different A-B disaccharide building blocks and i denotes the position of the disaccharide along the chain, measured from one end and wherein i is an integer, $1 \leq i \leq n$;

$_n[A-B]$ is the same or different A-B disaccharide building blocks and n denotes the building block at the opposite end of $_1[A-B]$; and n is from about 2 to about 10 and represents the length of chains of repeating A-B units;

with the proviso that $_1[A\text{-}B]\text{-}_2[A\text{-}B]\text{-}\ldots\text{-}_i[A\text{-}B]\text{-}\ldots\text{-}_n[A\text{-}B]$ is not a full length HLGAG molecule;

wherein said GAG oligosaccharide, GAG-like oligosaccharide, GAG-like composite or analog, homolog or ortholog binds to a ligand.

Another aspect of the invention provides a GAG-like composite molecule having the formula:

  (II) and

  (III).

or a chemical analog, homolog or ortholog of the molecule of Formula (II) or Formula (III);

wherein X is a molecule defined by the general formula:

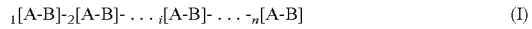  (I)

or a GAG-like oligosaccharide, GAG-like chemical analog, homolog or ortholog of the GAG oligosaccharide of Formula (I);

wherein:

A is an oligosaccharide or monosaccharide monomer unit comprising a saccharide such as, but not limited to, glucuronic acid, iduronic acid, glucosamine, mannose, mannan, dextran, glucose, fructose, sucrose, heptulose, pentose or sulfated forms thereof;

B may be the same as A or is a monomer unit comprising a glucosamine residue, a glucosamine derivative and/or a sulfated and/or a phosphorylated form thereof and/or acetylated form thereof or alkyl ether derivatives comprising methyl, ethyl, propyl or butyl;

wherein the monomer units, A and B, are linked by glycosidic bonds;

$_i[A\text{-}B]$ is the same or different A-B disaccharide building blocks and i denotes the position of the disaccharide along the chain, measured from one end and wherein i is an integer, $1 \leq i \leq n$;

$_n[A\text{-}B]$ is the same or different A-B disaccharide building blocks and n denotes the building block at the opposite end of $_1[A\text{-}B]$; and n is from about 2 to about 10 and represents the length of chains of repeating A-B units;

or a GAG-like oligosaccharide, GAG-like composite or chemical analog, homolog or ortholog thereof;

with the proviso that $_1[A\text{-}B]\text{-}_2[A\text{-}B]\text{-}\ldots\text{-}_i[A\text{-}B]\text{-}\ldots\text{-}_n[A\text{-}B]$ is not a full length HLGAG molecule;

P is a peptide, polypeptide or protein, chemical moiety, saturated or unsaturated fatty acid, lipid, dendrimer, saccharide, polyol, dextran, polyethylene glycol or branched or unbranched, saturated or unsaturated hydrocarbon chain or a flexible linker;

l and m are integers such that l, m=1 ... q;

q is an integer $1 \leq q \leq 9$;

wherein said GAG oligosaccharide, GAG-like oligosaccharide, GAG-like composite or analog, homolog or ortholog binds to a ligand.

The present invention further provides GAG oligosaccharides, GAG-like oligosaccharides, GAG-like composite molecules or non-GAG or non-GAG-like molecules which bind to the same target site on a ligand to which a GAG oligosaccharide binds.

Preferred ligands are peptides, polypeptides or proteins, such as cytokines or growth factors. Ligands contemplated herein include those selected from the list consisting of βc, Cyclophilin A, IL-1, IL-2, IL-3, IL-4, IL-5, IL-6, IL-7, IL-8, IL-10, IL-12, IL-13, G-CSF, M-CSF, GM-CSF, BDNF, CNTF, EGF, EPO, FGF1, FGF2, FGF3, FGF4, FGF5, FGF6, FGF7, FGF8, FGF9, FGF10, FGF11, FGF12, FGF12, FGF13, FGF14, FGF15, FGF16, FGF17, FGF18, FGF19, FGF20, FGF21, FGF22, FGF23, LIF, MCP1, MCP2, KC, MCP3, MCP4, MCP5, M-CSF, MIP1, MIP2, NOF, NT 3, NT4, NT5, NT6, NT7, OSM, PBP, PBSF, PDGF, PECAM-1, PF4, RANTES, SCF, TGFα, TGFβ$_1$, TGFβ$_2$, TGFβ$_3$, TNFα, TNFβ, TPO, VEGF, GH, chemokines, eotaxin (eotaxin-1, -2 or -3); or a soluble or cell- or virus-bound receptor. Particularly preferred ligands are IL-5, IL-4 and PECAM-1, gp120, βc chain of the IL-5 receptor and cyclophilin A.

The GAG oligosaccharide may be appended with a single saccharide, giving rise to an oligosaccharide of length $[A\text{-}B]_n\text{-}A$ or $B\text{-}[A\text{-}B]_n$.

B may also have mono-, di- or tri-saccharides appended to hydroxyl groups such as but not limited to the 6 position or in a terminal saccharide to give a branched structure; these attached saccharide units may be either sulfated, non-sulfated, phosphorylated or non-phosphorylated. When A is glucosamine, then A may also have mono-, di- or tri-saccharides appended to hydroxyl groups such as but not limited to the 6 position or in a terminal saccharide to give a branched structure; these attached saccharide units may be either sulfated, non-sulfated, phosphorylated or non-phosphorylated.

$_i[A\text{-}B]$ may have a terminal saccharide that is 4-deoxy-L-threo-hex-4-enopyranosyluronic acid or a derivative of a glucosamine resulting from treatment with nitrous acid such as 2,5-anhydro-D-manitol or a 2,5-anhydro-D-mannose or derivatives thereof.

Another aspect of the present invention provides a composition comprising one or more of the GAG oligosaccharides, GAG-like oligosaccharides and/or GAG-like composite molecule and one or more pharmaceutically acceptable carriers or diluents.

The present invention flirter extends to a site on a ligand and in particular a linear or conformational structure with which a GAG, GAG-like molecule or GAG-like composite or parts thereof interact.

The present invention further provides GAG oligosaccharides, GAG-like oligosaccharides, GAG-like composite molecules or non-GAG or non-GAG-like molecules including chemical analogs, homologs or orthologs thereof which bind to the same target site on a peptide, polypeptide or protein to which a GAG oligosaccharide binds.

Particularly preferred targets are IL-4, IL-5, Cyclophilin A and PECAM-1.

The target ligand IL-5 and the GAG oligosaccharide, GAG-like oligosaccharide, GAG-like composite molecule or non-GAG or non-GAG-like molecule interact with a three dimensional site defined by one or more residue(s) on IL-5 selected from the group consisting of: R32, R67, K70, K76, K77, K83, K84, K85, E88, E89, R90, R91 and/or R92.

In a yet further preferred embodiment, the GAG oligosaccharide, GAG-like oligosaccharide, GAG-like composite molecule or non-GAG or non-GAG-like molecule comprises the saccharide structure ΔUA2SGlcNS6S-(UA2SGlcNS6S)$_5$ or is an analog, homolog or ortholog thereof or binds to the same site as ΔUA2SGlcNS6S-(UA2SGlcNS6S)$_5$.

The target ligand PECAM-1 and the GAG oligosaccharide, GAG-like oligosaccharide, GAG-like composite molecule or non-GAG or non-GAG-like molecule bind to a three dimensional structure formed by any one or more of Domains 2, 3, 5 or 6 on PECAM-1. In a yet further preferred embodiment, the GAG oligosaccharide, GAG-like oligosaccharide, GAG-like composite molecule or non-GAG or non-GAG-like molecule interacts with Domain 2 and/or 3 or a three dimensional structure formed therefrom on PECAM-1.

The target ligand IL-4 and GAG oligosaccharide, GAG-like oligosaccharide, GAG-like composite molecule or non- GAG or non-GAG-like molecule interact with a three dimensional structure defined or formed by one or more residue(s) on IL-4 selected from the group consisting of: E9, K12, R53, E60, K61, H74, R75, K77, Q78, R81, R84, R85, D87 and/or R88. In a yet further preferred embodiment, the GAG oligosaccharide, GAG-like oligosaccharide, GAG-like composite molecule or non-GAG or non-GAG-like molecule comprises the saccharide structure selected from the group consisting of: ΔUA2SGlcNS6S-(UA2SGlcNS6S)$_4$, ΔUA2SGlcNS6S-(UA2SGlcNS6S)$_3$-UAGlcNS6S, ΔUA2SGlcNS6S-UAGlcNAc6S-UA2SGlcNS6S-UA2SGlcNS-UA2SGlcNS6S, ΔUA2SGlcNS6S-UAGlcNAc6S-UA2SGlcNS6S-UA2SGlcNS6S-UA2SGlcNS, ΔUA2SGlcNS6S-UA2SGlcNS-UA2SGlcNS6S-UAGlcNAc6S-UA2SGlcNS6S, ΔUA2SGlcNS-UA2SGlcNS6S-UA2SGlcNS6S-UAGlcNAc6S-UA2SGlcNS6S, or an analog, homolog or ortholog thereof or binds to the same site as the above GAG molecules.

Still another aspect of the present invention provides a method for generating libraries of GAG oligosaccharides or GAG-like oligosaccharides (which may or may not be branched) or GAG-composite structures and methods for identifying GAG oligosaccharides and/or parts or portions thereof, or GAG-like oligosaccharides (which may or may not be branched), or GAG-composite structures which bind to a particular protein. The GAGs or other structures produced according to the method of the present invention have application for treating any disease that involves interaction between GAG-like molecules and a ligand, such as a protein. The GAGs or other structures are particularly useful in the treatment of inflammatory or allergic disease conditions and metastatic cancers and infection by pathogenic agents such as bacteria, viruses or parasites.

The GAG, GAG-like and GAG-like composite molecules of the present invention may be derived from polymers via truncation and at least one of deacetylation, sulfation, desulfation, phosphorylation and attachment of side chains.

Preferred starting polymers include inter alia *E. coli* K5 polysaccharide, chitin or chitosan.

In an alternate embodiment of the present invention, GAG oligosaccharides are generated by the method comprising size fractionating a population of starting polymer such as heparin, heparan sulfate molecules, K5 polysaccharide, chitin or chitosan to generate non-full length fractions which interact with a ligand. Heparin comprises mixtures of glucuronic and iduronic acids in some of the disaccharide units and varying degrees of sulfation. Fractionation may be by any convenient means such as by gel filtration column and is based on different length saccharide chains generally but not exclusively from a DP4 to about a DP20 including DP5, DP6, DP7, DP8, DP9, DP10, DP11, DP12, DP13, DP14, DP15, DP16, DP17, DP18, DP19 or DP20. Another form of separation is on the basis of extent of sulfation. The separation may also be based on a combination of these two parameters.

Another aspect of the present invention is the provision of 6-O phosphorylated GAG oligosaccharides. These molecules are generated by the inclusion of a phosphorylation step when generating the library of GAG oligosaccharides. It is contemplated that this phosphorylation step and any associated desulfation steps that may be necessary can be performed on both the semi-synthetic oligosaccharides derived from polymers such as *E. coli* K5 polymer, chitin or chitosan, and oligosaccharides produced by fractionation of HLGAGs such as heparin or heparan sulfate or fractionation of other polymers such as K5, chitin or chitosan.

Another aspect of the present invention is directed to a method for generating a medicament for treating a disease condition in a subject, said method comprising producing a range of GAG oligosaccharides or GAG-like oligosaccharides or composite structures according to the methods of the subject invention and screening each GAG or GAG-like oligosaccharides or composite structures for an ability to interact with or modulate the ligand. The GAG oligosaccharide which interacts with or modulates the ligand is identified and either the oligosaccharide or an analog, agonist or antagonist thereof is used in the manufacture of the medicament.

Yet another aspect of the present invention contemplates a method of treatment of a disease condition in a subject, the disease condition resulting from interaction between a HLGAG on a surface of a cell in said host and a ligand, or a HLGAG in the extracellular matrix in said host and a ligand that may or may not be cell associated, or a protein-ligand interaction in said host that can be disrupted by a HLGAG where the protein may be cell associated and the ligand soluble or both protein and ligand may be cell associated, said method comprising administering to said subject an effective amount of a medicament, said medicament being a GAG oligosaccharide, or GAG-like oligosaccharides, or composite structures, produced and identified according to the present invention, that interacts with said ligand and incorporating said fraction into a medicament or obtaining a chemical analog or homolog thereof and incorporating same into said medicament.

FIG. 3 is a graphical representation showing rhIL-4 HLGAG filter-binding assay. Either 10 nmol (♦) or 20 nmole (■) rhIL-4 was incubated with various amounts of fluorescent-labeled heparin. Unbound heparin was removed by centrifugation, and bound heparin was redissolved with 2M NaCl. The amount of bound heparin was determined with a Wallac Victor 1420 96 well plate reader, and quantified using standard solutions of fluorescent heparin diluted in the same buffer. The data are the average of two individual experiments.

FIGS. 4A and 4B are graphical representations showing competitive inhibition of IL-4/IL-5 heparin interaction. Either IL-4 or IL-5 was incubated with a large molar excess of HLGAG fragments of the sizes indicated. These mixtures were injected over the BIAcore sensor chips carrying immobilized HLGAGs, and the level of binding was recorded, and compared with the binding observed by the proteins without inhibitor. Panel A—IL-4. Panel B—IL-5. Fragment pools that could reduce binding by greater than 50% were targeted for further analysis.

FIGS. 5A-5C are graphical representations showing direct binding of proteins to immobilized HLGAG fragments. The fragments were biotinylated through their reducing terminus and immobilized on streptavidin sensor chips. Standard solutions of the proteins of interest were injected over the surfaces, and the amount of binding was determined. Panel A, rhIL-4. Panel B, flag-PECAM-1. Panel C, CypA. The binding data are the average of three separate binding experiments±standard error.

Figure 6:
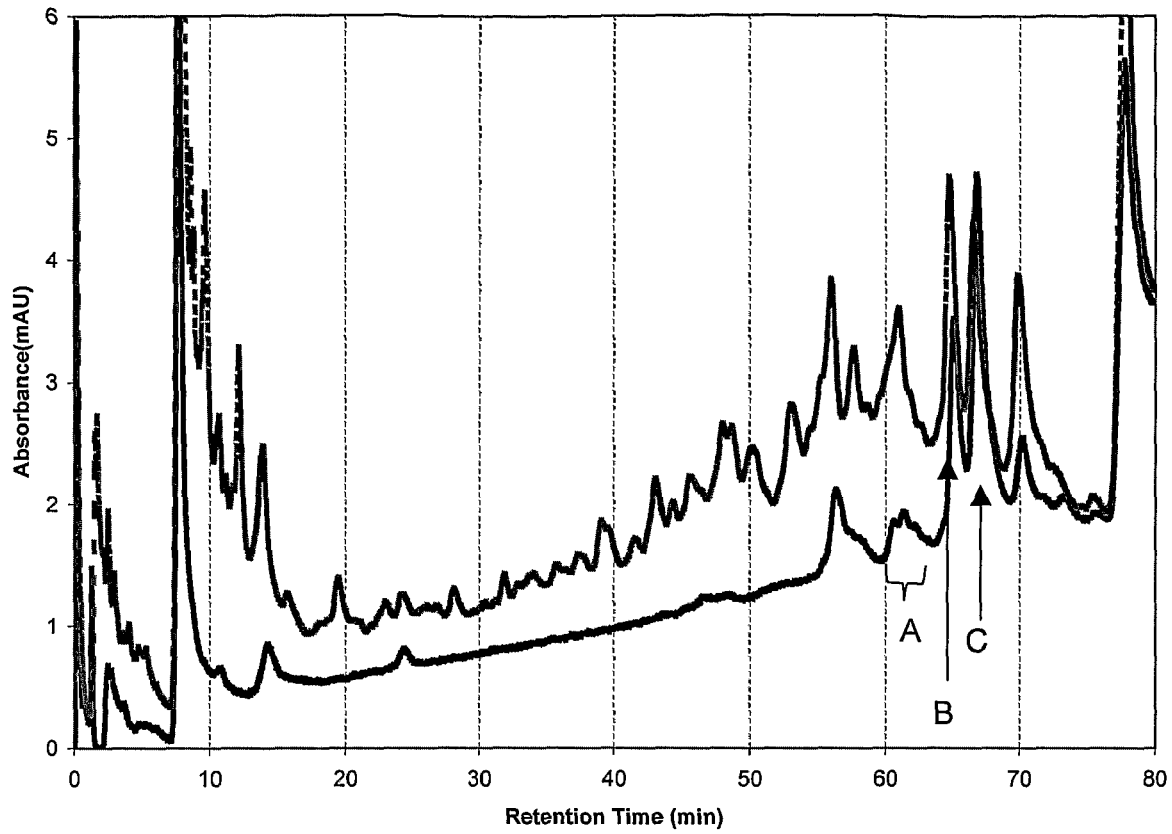

FIG. 6 is a graphical representation showing anion exchange chromatography of DP10 size pool (lighter curve) and the IL-4 affinity purified sub-fraction of DP10 (darker curve). The labels A-C denote the fractions analyzed by MALDI MS.

Figure 7:
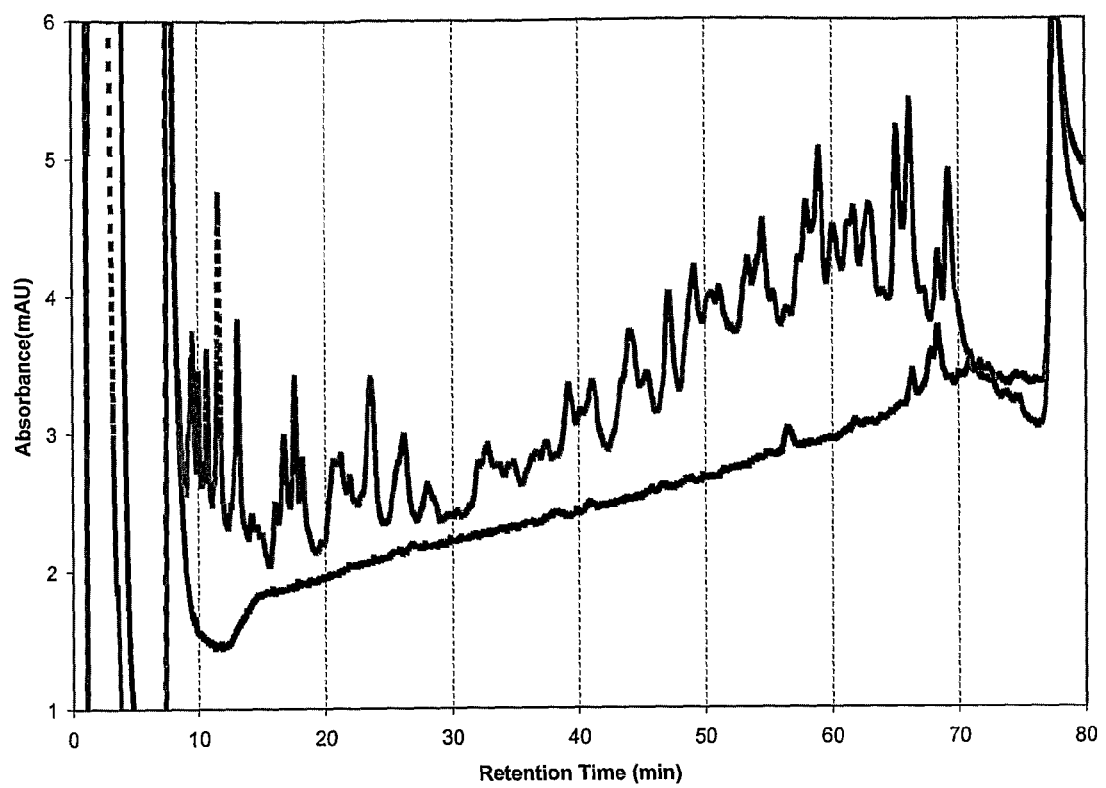

FIG. 7 is a graphical representation showing anion exchange chromatography of DP12 size pool (lighter curve) and the IL-5 affinity purified sub-fraction of DP12 (darker curve).

Figure 8:
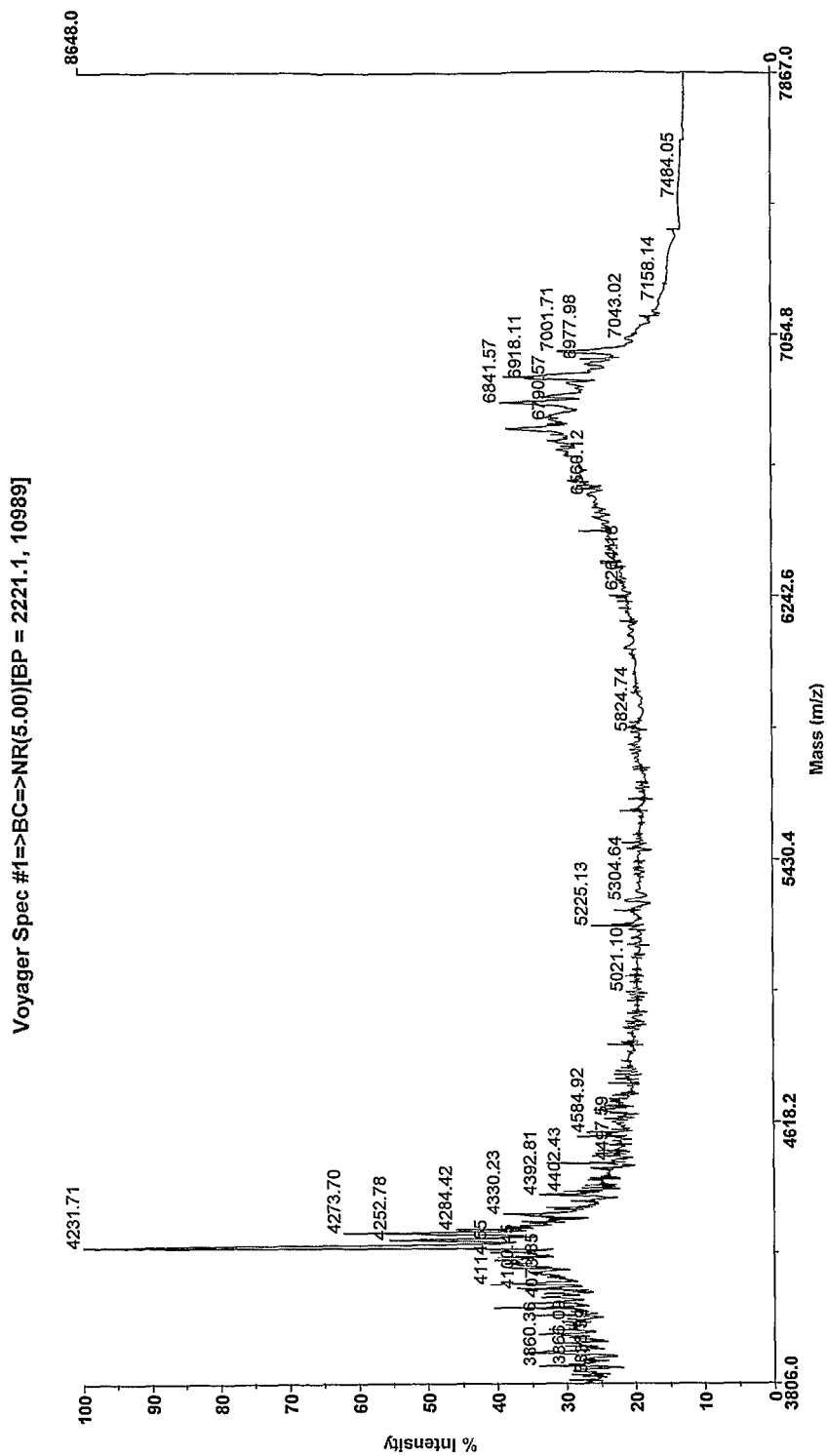

FIG. 8 is a graphical representation showing MALDI mass spectrum of DP 10 fraction A (from the chromatogram in FIG. 6). The mass of the oligosaccharide is deduced from the mass of the peptide and the peptide-oligosaccharide complexes.

Figure 9:
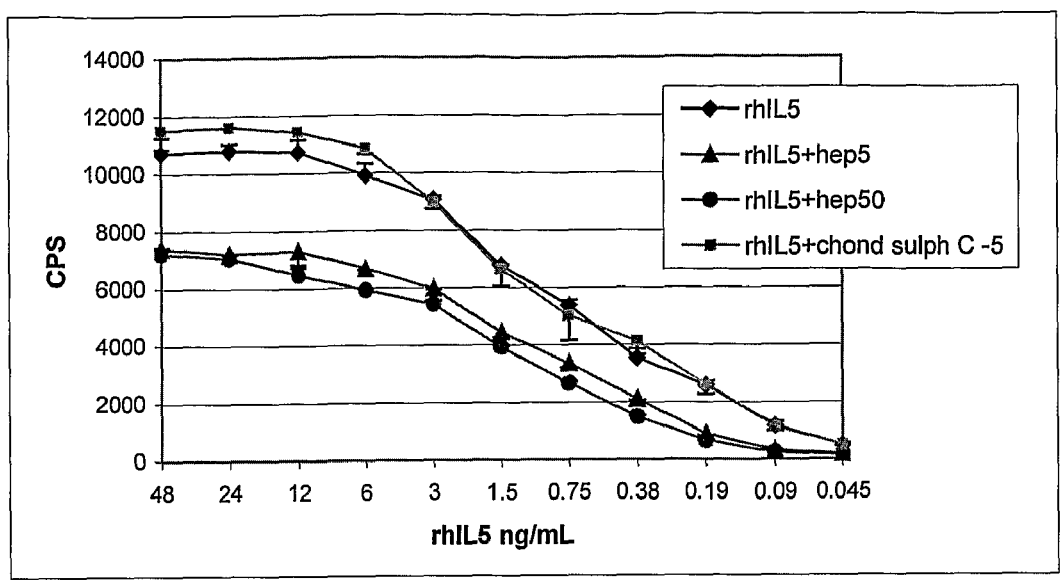

FIG. 9 is a graphical representation showing Bioassay using Baf-IL-5 cells. Panel A: rhIL-5 was added at the concentrations shown in the presence of heparin at 5 μg/mL and 50 μg/mL, or chondroitin sulfate C at 5 μg/mL, or without added GAGs. Luciferase activity was measured after 48 hours and is expressed as counts per second (CPS). The data shown are the average of two replicates. Panel B shows the effect of various concentrations of heparin on the proliferation of Baf-IL-5 cells in the presence of 6 ng/ml rhIL-5. The data are presented as a % inhibition of proliferation in the presence of various concentrations of heparin compared to a no heparin control.

Figure 10:
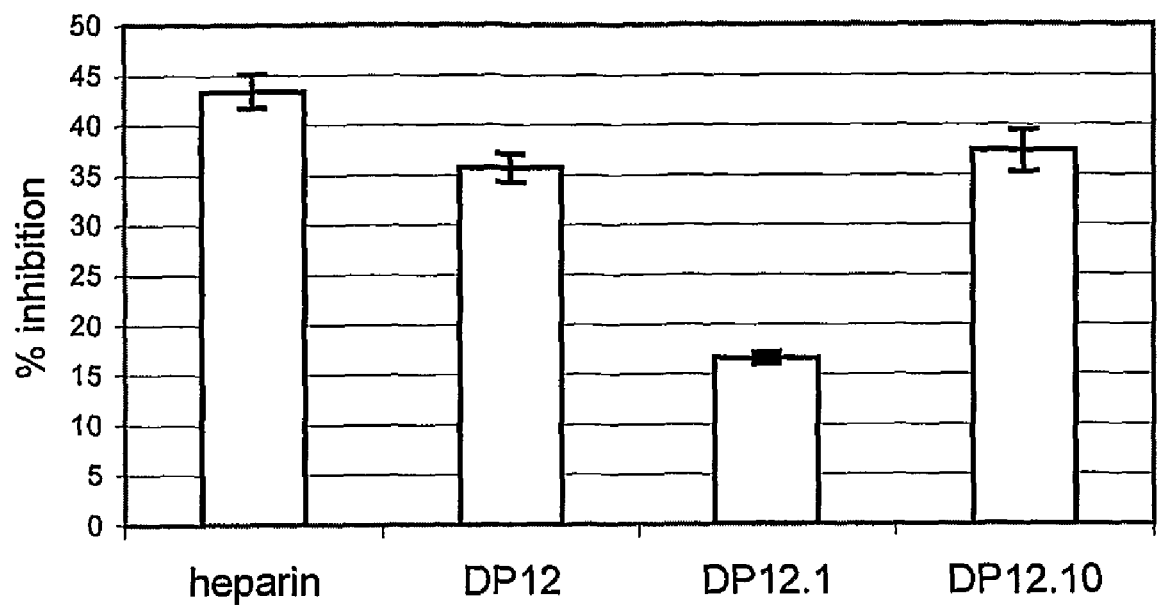

FIG. 10 is a graphical representation showing the effect of heparin (0.4 μM), the DP12 (1 μM) pool of heparin fragments and selected sub-fractions of the DP12 pool (each at 1 μM) on the IL-5 (0.07 ng/ml) dependent proliferation of Ba/F-IL-5 cells. These sub-fractions either exhibit strong binding to IL-5 (DP12.10), or they have little binding activity (DP12.1). Data are expressed as % inhibition relative to the proliferation observed in the absence of heparin or the heparin fragments. Means and standard deviations of a minimum of three replicates.

Figure 11:
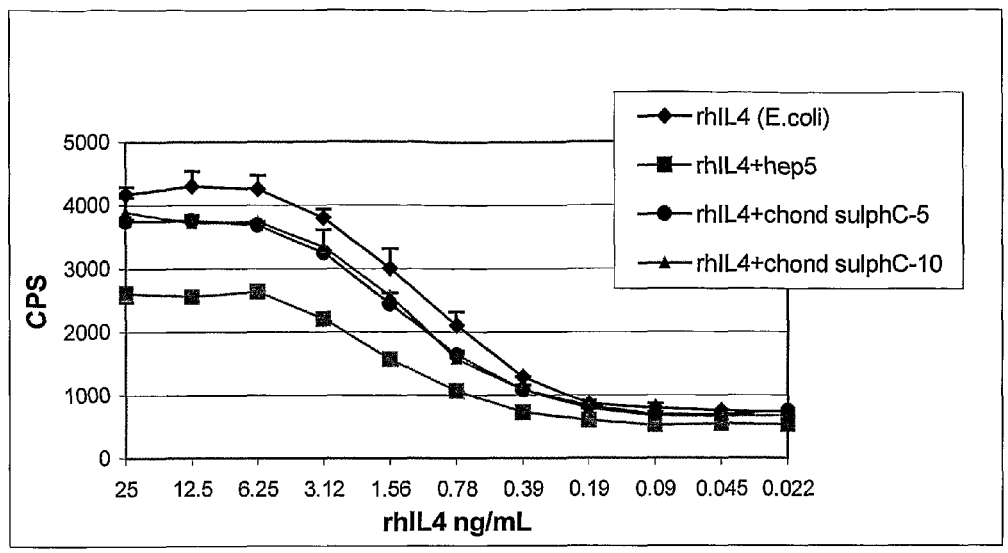
Figure 11:
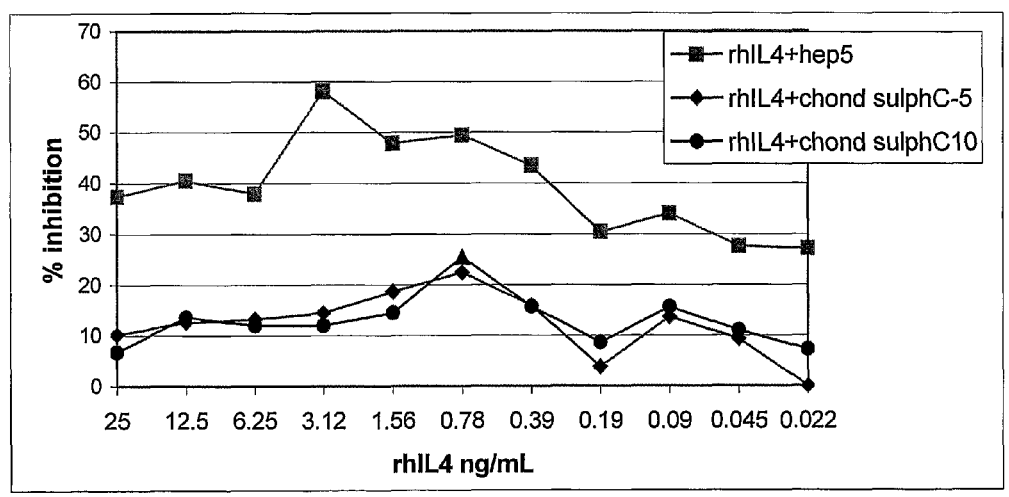

FIG. 11 are graphical representations showing the effect of heparin at 5 μg/mL and chondroitin sulfate C at 5 μg/mL and 10 μg/mL on the IL-4 induced proliferation of TF1.8 cells. The data are presented as luciferase activity measured as counts per second (CPS) (A). The data in (B) has been calculated as % inhibition of proliferation relative to the proliferation obtained with the appropriate concentration of cytokine but in the absence of GAG.

Figure 12:
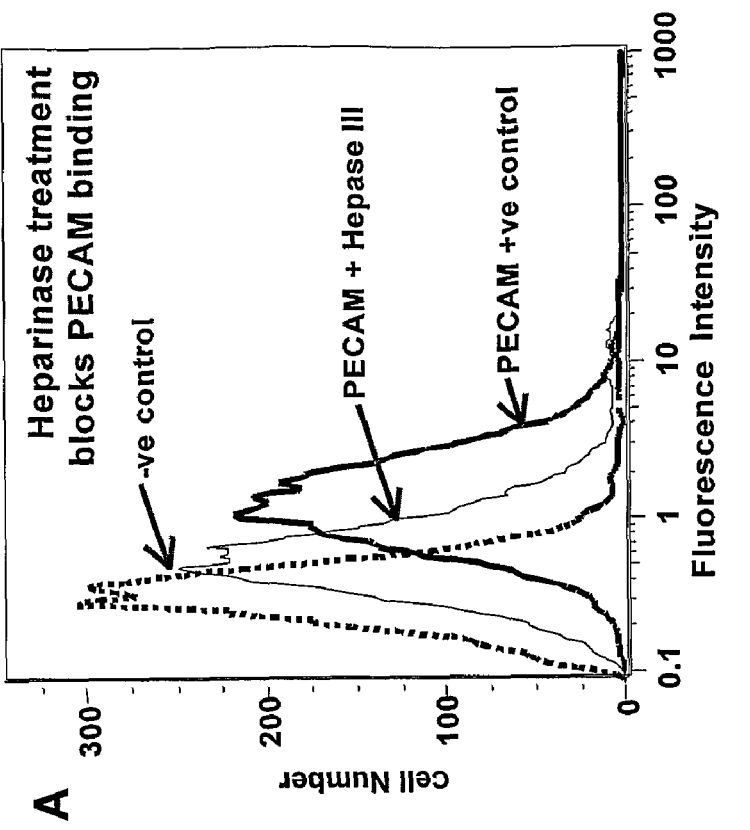
Figure 12:
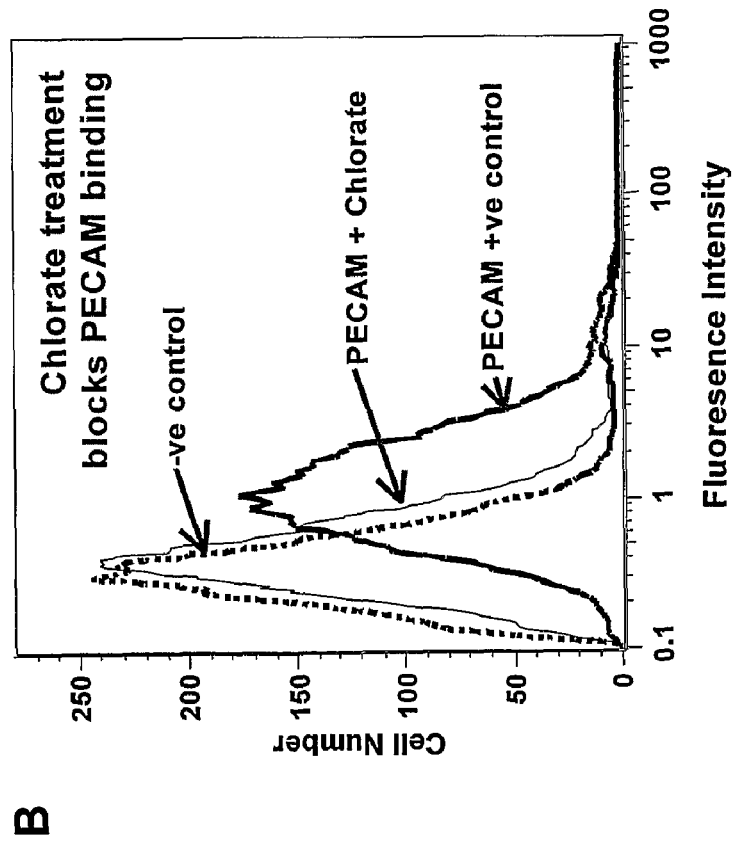

FIG. 12 is a graphical representation showing flag-PECAM-1 binding to A2058 melanoma cells. The negative control consisting of the anti-PECAM-1 polyclonal antibody and the FITC-conjugated anti-rabbit second antibody is shown in the dotted histogram. flag-PECAM-1 binding detected with the anti-PECAM-1 polyclonal antibody and the FITC-conjugated anti-rabbit second antibody in the absence of heparinase III treatment (bold histogram) and after heparinase III treatment (light line). Panel B shows the effect of chlorate treatment of A2058 cells on the ability of flag-PECAM-1 to bind to these cells. The binding of flag-PECAM-1 is measured by flow cytometry following visualisation using an anti-PECAM-1 polyclonal antibody and a FITC conjugated second antibody. Positive control is flag-PECAM-1 binding to untreated A2058 cells, negative control is anti-PECAM-1 polyclonal antibody and the FITC conjugated second antibody without flag-PECAM-1.

Figure 13:
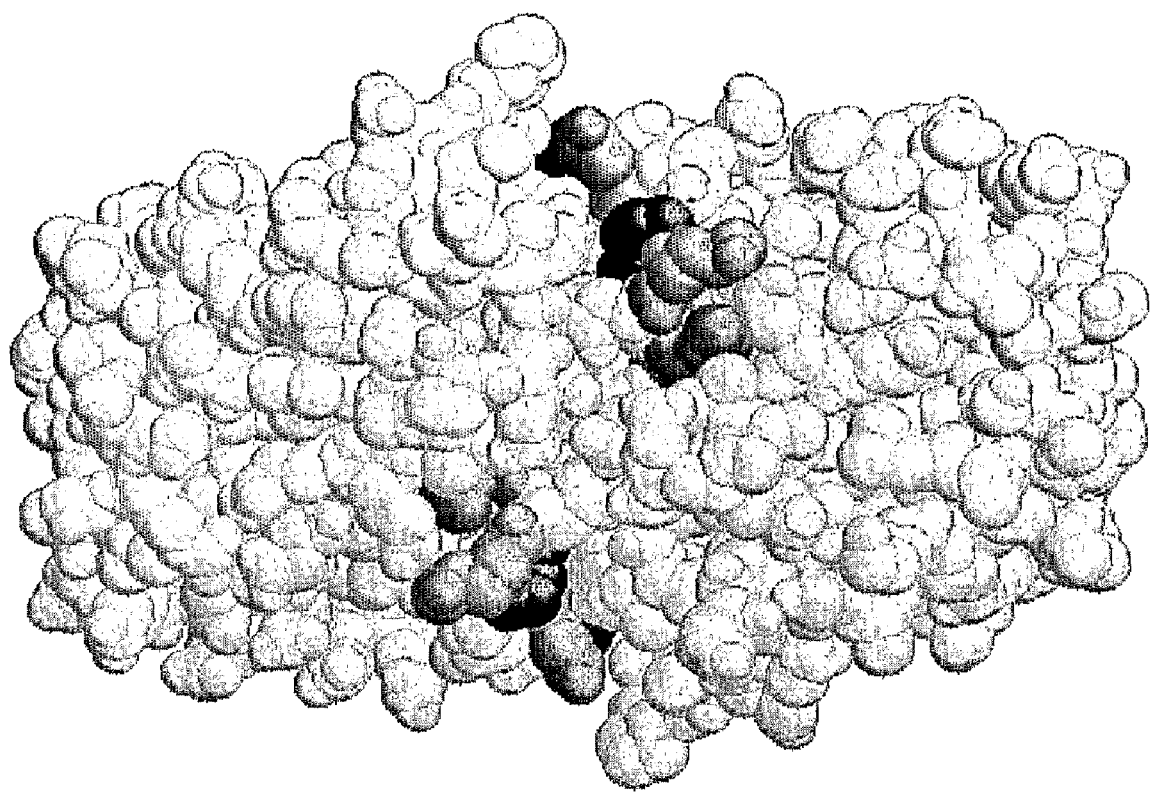

FIG. 13 is a representation showing the location of amino acids mutations that affect IL-5 binding to HLGAGs. Amino acid changes that affect the level of IL-5-HLGAG binding were compiled, and mapped on a three-dimensional protein model. Several amino acids on rhIL-5 have been shown to be important for HLGAG binding, namely, mutation of lysine 84, lysine 85. The binding site extends along the C-helix and includes lysine 77, lysine 76, lysine 70 and arginine 67. Amino acids on the adjacent β-pleated sheet namely, arginine 90 and arginine 91 may also be involved.

FIG. 14 is a schematic representation of IL-4 target 1, comprised of a regular repeat of the trisulfated disaccharide.

FIG. 15 is a schematic representation of IL-4 target 2.

FIG. 16 is a schematic representation of IL-5 target 1, comprised of a regular repeat of the trisulfated disaccharide.

FIG. 17 is a diagrammatic representation of *E. coli* K5 capsular polysaccharide and non-sulfated heparin backbone polysaccharide.

FIG. 18 is a graphical representation showing the results of a BIAcore assay of domains D1-D6 of PECAM-1 binding to the heparin chip in the presence or absence of exogenous heparin at 2.5 μM. In these experiments 1 μM of purified PECAM-1 was used.

FIG. 19 is a diagrammatic representation of the various PECAM-1 constructs using both the Flag expression system (Panel A) and the fusion protein expression system (Panel B).

FIG. 20 is a graphical representation showing, in panel A, an electrophoresis gel indicating the purity of the PECAM-Fc domain deletion proteins. While in Panel B the binding of PECAM-Fc fusion proteins to heparin immobilised on a biosensor chip. Legend: I: D1-Fc; II: D1-2-Fc; III D1-3-Fc; IV: D1-4-Fc; V: D1-5-Fc and VI: D1-6-Fc.

FIG. 21 is a graphical representation showing the binding of the Flag-PECAM-1 domain constructs to heparin immobilised on a BIAcore chip. Refer to FIG. 19 for which domains are included in each of the proteins indicated.

FIG. 22 is a graphical representation showing the results of a BIAcore assay investigating the effects of exogenous heparin on the binding of Flag-PECAM-1 constructs to heparin immobilised on a biosensor chip. Note that the binding of all constructs to the biosensor chip was almost totally inhibited by the addition of 2.5 μM heparin. In all cases 1 μM of protein was used.

FIG. 23 is a graphical representation showing the binding of Flag-PECAM-1 extracellular domains to A2058 melanoma cells. A: Flag-PECAM-1 D1-6; B: Flag-PECAM-1 D1-3; C: Flag-PECAM D1-2. Flag-PECAM-1 domains (solid line), Control (dotted line), Flag-PECAM-1 domains plus 50 μg heparin (dashed line). PECAM-1 domain binding is detected by an anti-PECAM-1 polyclonal antibody and a FITC labeled second antibody, with quantification by flow cytometry.

FIG. 24 is a graphical representation depicting the binding of different concentrations of IL-4 to heparin immobilised on a biosensor chip as measured using BIAcore.

FIG. 25 is a graphical representation showing IL-4 mutants expressed using baculovirus expression and the proteins purified by affinity chromatography on an anti-IL-4 (11B4.6) column. The binding of the mutants to a heparin-coupled biosensor chip was compared to that of wild-type IL-4 at a concentration range of 62.5 nM-1 μM. The binding of wild type IL-4 is set at 100%.

FIG. 26 is a graphical representation depicting a molecular model of a heparin pentasaccharide consisting of repeats of the trisulfated disaccharide (Ido2SGlcNS6S), binding to IL-4. The twenty best binding positions are shown. The helical structure of the protein has been displayed and the amino acids believed to contribute to the heparin binding site are indicated as space-filled models.

FIG. 27 is a graphical representation of a sensorgram obtained using BIAcore 2000 when IL-5 in the presence or absence of 3-OST-3 modified heparan sulfate is passed over immobilized heparin.

FIG. 28 is a graphical representation of a sensorgram obtained using BIAcore 2000 when IL-5 in the presence or absence of 3-OST-3 modified DP12 fragments are passed over immobilized heparin.

DETAILED DESCRIPTION OF THE PREFERRED EMBODIMENTS

The present invention relates generally to preparations of GAG molecules and to individual members or fractions of GAG molecules, including GAG-like oligosaccharides and GAG-composite molecules composed of GAG-like structures and non-GAG linkers as well as chemical analogs, homologs or orthologs thereof useful in the treatment of a range of conditions such as inflammatory or allergic conditions like allergic rhinitis and asthma, metastatic cancer or infection by a pathogenic agent including bacteria, viruses and parasites such as HIV, a corona virus including the SARS virus, the avian influenza virus, or the malaria parasite. Reference to a "GAG" molecule includes reference to a GAG-like molecule including GAG-like molecules produced on a non-GAG backbone. The present invention also relates to the site on the ligand to which the GAG molecules or GAG-composite molecules bind. Generally, this binding site will be dictated by the three-dimensional configuration of the ligand.

Before describing the present invention detail, it is to be understood that unless otherwise indicated, the subject invention is not limited to specific formulations of components, manufacturing methods, dosage regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to a "GAG" includes a single GAG, as well as two or more GAGs; reference to "an active agent" includes a single active agent, as well as two or more active agents; and so forth.

In describing and claiming the present invention, the following terminology is used in accordance with the definitions set forth below.

The terms "compound", "active agent", "chemical agent", "pharmacologically active agent", "medicament", "active" and "drug" are used interchangeably herein to refer to a chemical compound that induces a desired pharmacological and/or physiological effect. The terms also encompass pharmaceutically acceptable and pharmacologically active ingredients of those active agents specifically mentioned herein including but not limited to salts, esters, amides, prodrugs, active metabolites, analogs and the like. When the terms "compound", "active agent", "chemical agent" "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc.

Reference to a "compound", "active agent", "chemical agent" "pharmacologically active agent", "medicament", "active" and "drug" includes combinations of two or more actives such as two or more GAG molecules or GAG-composite molecules or a GAG molecule and another therapeutic agent. A "combination" also includes multi-part such as a two-part pharmaceutical composition where the agents are provided separately and given or dispensed separately or admixed together prior to dispensation.

For example, a multi-part pharmaceutical pack may have a GAG or population of GAGs and one or more anti-microbial or anti-viral agents.

The terms "effective amount" and "therapeutically effective amount" of an agent as used herein mean a sufficient amount of the agent to provide the desired therapeutic or physiological effect. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like. A pharmaceutical composition may also be described depending on the formulation as a vaccine composition.

Similarly, a "pharmacologically acceptable" salt, ester, amide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms of the disease condition or infection, elimination of symptoms and/or underlying cause, prevention of the occurrence of symptoms of the disease condition or infection and/or their underlying cause and improvement or remediation of damage following a disease condition or infection.

"Treating" a patient may involve prevention of a disease condition or infection or other disease condition or adverse physiological event in a susceptible individual as well as treatment of a clinically symptomatic individual by inhibiting a disease condition or infection or downstream condition by a pathogen such as a virus, a prokaryotic organism or eukaryotic organism. Thus, for example, the subject method of "treating" a patient with an infection or with a propensity for one to develop encompasses both prevention of the infection or other disease condition as well as treating the infection or other disease condition once established. In any event, the present invention contemplates the treatment or prophylaxis of an infection by a pathogenic organism or virus or the treatment of another disease condition. Examples of prokaryotic organisms include *Salmonella, Escherichia, Klebsiella, Pasteurella, Bacillus* (including *Bacillus anthracis*), *Clostridium, Corynebacterium, Mycoplasma, Ureaplasma, Actinomyces, Mycobacterium, Chlamydia, Chlamydophila, Leptospira, Spirochaeta, Borrelia, Treponema, Pseudomonas, Burkholderia, Dichelobacter, Haemophilus, Ralstonia, Xanthomonas, Moraxella, Acinetobacter, Branhamella, Kingella, Erwinia, Enterobacter, Arozona, Citrobacter, Proteus, Providencia, Yersinia, Shigella, Edwardsiella, Vibrio, Rickettsia, Coxiella, Ehrlichia, Arcobacteria, Peptostreptococcus, Candida, Aspergillus, Trichomonas, Bacterioides, Coc-* cidiomyces, Pneumocystis, Ctyptosporidium, Porphyromonas, Actinobacillus, Lactococcus, Lactobacillua, Zymononas, Saccharomyces, Propionibacterium, Streptomyces, Penicillum, Neisseria, Staphylococcus, Campylobacter, Streptococcus, Enterococcus or Helicobacter. Examples of viruses include human immunodeficiency virus (HIV), Varicella-Zoster virus (VZV), herpes simplex virus (HSV), human papillomavirus (HPV), Hepatitis B virus (HBV), Hepatitis A virus (HAV), rhinovirus, echovirus, Coxsackievirus, cytomegalovirus, flavivirus, Ebola virus, paramyxovirus, influenza virus, enterovirus, Epstein-Barr virus, Marburg virus, polio virus, rabies virus, rubella virus, smallpox virus, rubeola virus, vaccina virus, adenovirus, corona virus including the SARS virus, influenza viruses including avian influenza virus and rotavirus. In a preferred embodiment, the disease is allergic rhinitis.

"Patient" as used herein refers to an animal, preferably a mammal and more preferably human who can benefit from the pharmaceutical formulations and methods of the present invention. There is no limitation on the type of animal that could benefit from the presently described pharmaceutical formulations and methods. A patient regardless of whether a human or non-human animal may be referred to as an individual, subject, animal, host or recipient. The compounds and methods of the present invention have applications in human medicine, veterinary medicine as well as in general, domestic or wild animal husbandry. For convenience, an "animal" includes an avian species such as a poultry bird, an aviary bird or game bird. A poultry bird such as a duck is a preferred example of an avian species.

As indicated above, the preferred animals are humans or other primates such as orangutangs, gorillas, marmosets, livestock animals, laboratory test animals, companion animals or captive wild animals, as well as avian species.

Examples of laboratory test animals include mice, rats, rabbits, guinea pigs and hamsters. Rabbits and rodent animals, such as rats and mice, provide a convenient test system or animal model. Livestock animals include sheep, cows, pigs, goats, horses and donkeys. Non-mammalian animals such as avian species (such as ducks), zebrafish, amphibians (including cane toads) and *Drosophila* species such as *Drosophila melanogaster* are also contemplated.

In this specification, the term "GAG" is used to generically define molecules of the glycosaminoglycan group, the defining structural features of which are well known to those of skill in the art. As used in the specification, the term GAG oligosaccharide is any GAG molecule that is shorter, as measured by number of monosaccharide residues, than corresponding GAG polysaccharide from which it is derived. As indicated above, a "GAG" includes GAG-like molecules, such molecules produced on a non-GAG backbone as well as GAG-like composite molecules comprising one or more GAG-like portions joined by a non-GAG linker Accordingly, one aspect of the invention is directed to a GAG oligosaccharide having the formula:—

  (II) or

  (III).

or a chemical analog, homolog or ortholog of the molecule of Formula (II) or Formula (III);
wherein X is a molecule defined by the general formula:

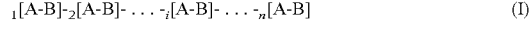  (I)

or a GAG-like oligosaccharide, GAG-like chemical analog, homolog or ortholog of the GAG oligosaccharide of Formula (I);

wherein:
A is an oligosaccharide or monosaccharide monomer unit comprising a saccharide such as, but not limited to, glucuronic acid, iduronic acid, glucosamine, mannose, mannan, dextran, glucose, fructose, sucrose, heptulose, pentose or sulfated forms thereof;
B may be the same as A or is a monomer unit comprising a glucosamine residue, a glucosamine derivative and/or a sulfated and/or a phosphorylated form thereof and/or acetylated form thereof or alkyl ether derivatives comprising methyl, ethyl, propyl or butyl;
wherein the monomer units, A and B, are linked by glycosidic bonds;
$_i[A-B]$ is the same or different A-B disaccharide building blocks and i denotes the position of the disaccharide along the chain, measured from one end and wherein i is an integer, $1 \leq i \leq n$;
$_n[A-B]$ is the same or different A-B disaccharide building blocks and n denotes the building block at the opposite end of $_1[A-B]$; and
n is from about 2 to about 10 and represents the length of chains of repeating A-B units;
or a GAG-like oligosaccharide, GAG-like composite or chemical analog, homolog or ortholog thereof;
with the proviso that $_1[A-B]-_2[A-B]- \ldots -_i[A-B]- \ldots -_n[A-B]$ is not a full length HLGAG molecule;
P is a peptide, polypeptide or protein, chemical moiety, saturated or unsaturated fatty acid, lipid, dendrimer, saccharide, polyol, dextran, polyethylene glycol or branched or unbranched, saturated or unsaturated hydrocarbon chain or a flexible linker;
l and m are integers such that l, m=1 . . . q;
q is an integer $1 \leq q \leq 9$;
wherein said GAG oligosaccharide, GAG-like oligosaccharide, GAG-like composite or analog, homolog or ortholog binds to a ligand such as but not limited to a ligand selected from the list consisting of βc, Cyclophilin A, IL-1, IL-2, IL-3, IL-4, IL-5, IL-6, IL-7, IL-8, IL-10, IL-12, IL-13, G-CSF, M-CSF, GM-CSF, BDNF, CNTF, EGF, EPO, FGF1, FGF2, FGF3, FGF4, FGF5, FGF6, FGF7, FGF8, FGF9, FGF10, FGF11, FGF12, FGF12, FGF13, FGF14, FGF15, FGF16, FGF17, FGF18, FGF19, FGF20, FGF21, FGF22, FGF23, LIF, MCP1, MCP2, KC, MCP3, MCP4, MCP5, M-CSF, MIP1, MIP2, NGF, NT 3, NT4, NT5, NT6, NT7, OSM, PBP, PBSF, PDGF, PECAM-1, PF4, RANTES, SCF, TGFα, TGFβ$_1$, TGFβ$_2$, TGFβ$_3$, TNFα, TNFβ, TPO, VEGF, GH, chemokines, eotaxin (eotaxin-1, -2 or -3); or a soluble or cell- or virus-bound receptor. Particularly preferred ligands are IL-4, IL-5 and PECAM-1, gp120, βc chain of IL-5 receptor and cyclophilin A The oligosaccharide may be appended to in a single saccharide, giving rise to an oligosaccharide of length $_n[A-B]$-A or B-$_n[A-B]$.

B may also have mono-, di- or tri-saccharides appended to hydroxyl groups such as but not limited to the 6 position or on a terminal saccharide to give a branched structure; these attached saccharide units may be either sulfated, non-sulfated, phosphorylated or non-phosphorylated. When A is glucosamine, then A may also have mono-, di- or tri-saccharides appended to hydroxyl groups such as but not limited to the 6 position or on a terminal saccharide to give a branched structure; these attached saccharide units may be either sulfated, non-sulfated, phosphorylated or non-phosphorylated.

$_i[A-B]$ may have a terminal saccharide that is 4-deoxythreo-hex-4-enopyranosyluronic acid or a derivative of a glucosamine resulting from treatment with nitrous acid such as 2,5-anhydro-D-manitol or a 2,5-anhydro-D-mannose or derivatives thereof.

The present invention further provides GAG oligosaccharides, GAG-like oligosaccharides, GAG-like composite molecules or non-GAG or non-GAG-like molecules which bind to the same target site on a peptide, polypeptide or protein to which a GAG oligosaccharide binds.

In one preferred embodiment, the target protein is IL-5 and the GAG oligosaccharide, GAG-like oligosaccharide, GAG-like composite molecule or non-GAG or non-GAG-like molecule interacts with a three dimensional site defined by one or more residue(s) on IL-5 selected from the group consisting of: R32, R67, K70, K76, K77, K83, K84, K95, E88, E89, R90, R91 and/or R92. In a yet further preferred embodiment, the GAG oligosaccharide, GAG-like oligosaccharide, GAG-like composite molecule or non-GAG or non-GAG-like molecule comprises the saccharide structure ΔUA2SGlcNS6S-(UA2SGlcNS6S)$_5$ or an analog, homolog or ortholog thereof, or a molecule which binds or interacts with the same site as structure ΔUA2SGlcNS6S-(UA2SGlcNS6S)$_5$.

In another preferred embodiment, the target protein is PECAM-1 and the GAG oligosaccharide, GAG-like oligosaccharide, GAG-like composite molecule or non-GAG or non-GAG-like molecule binds to a three dimensional site defined by or contributed to by any one or more of Domains 2, 3, 5 or 6 on PECAM-1. In a yet further preferred embodiment, the GAG oligosaccharide, GAG-like oligosaccharide, GAG-like composite molecule or non-GAG or non-GAG-like molecule interacts with Domain 2 and/or 3 on PECAM-1.

In yet another preferred embodiment, the target protein is IL-4 and GAG oligosaccharide, GAG-like oligosaccharide, GAG-like composite molecule or non-GAG or non-GAG-like molecule interacts with a three dimensional site defined by any one or more residue(s) on IL-4 selected from the group consisting of: E9, K12, R53, E60, K61, H74, R75, K77, Q78, R81, R84, R85, D87 and R88. In a yet further preferred embodiment, the GAG oligosaccharide, GAG-like oligosaccharide, GAG-like composite molecule or non-GAG or non-GAG-like molecule comprises the saccharide structure selected from the group consisting of: ΔUA2SGlcNS6S-(UA2SGlcNS6S)$_4$, ΔUA2SGlcNS6S-UA2SGlcNS6S)$_3$-UAGlcNS6S, ΔUA2SGlcNS6S-UAGlcNAc6S-UA2SGlcNS6S-UA2SGlcNS-UA2SGlcNS6S, ΔUA2SGlcNS6S-UAGlcNAc6S-UA2SGlcNS6S-UA2SGlcNS6S-UA2SGlcNS, ΔUA2SGlcNS6S-UA2SGlcNS-UA2SGlcNS6S-UAGlcNAc6S-UA2SGlcNS6S, ΔUA2SGlcNS-UA2SGlcNS6S-UA2SGlcNS6S-UAGlcNAc6S-UA2SGlcNS6S, or an analog, homolog or ortholog thereof, or a molecule which binds or interacts to a three dimensional structure defined by the binding of the above-mentioned GAG molecules.

Analysis of a set of IL-4 mutants for their ability to bind heparin and for their ability to induce proliferation of the growth factor-dependent cell line, TF1.8, indicates that the heparin binding site overlaps the IL-4R alpha binding site. A key residue for both being R88. Other residues involved in both heparin binding and the binding of IL-4R alpha are R81, R84, R53 and possibly E9. E9 is a key residue for IL-4R alpha binding but it is on the edge of the heparin binding site.

The term "HLGAG" (heparin-like glycosaminoglycan) is used as a term to indicate common cell surface GAG molecules. Used in this context, the term refers to full-length molecules of this type such as heparin and heparan sulfate. It is these cell surface GAGs which interact with ligands and can lead to disease conditions such as inflammatory diseases, metastatic cancers or susceptibility to infection by pathogenic agents.

Heparin and heparan sulfates consist of repeating disaccharide units comprising a hexuronic acid (HexA) and a D-glucosamine (GlcN) linked to each other and to other disaccharides by 1→4 linkages. The uronic acid may be either a β-D-glucuronic acid (GlcA) or α-L-iduronic acid (IdoA). Both occur as underivatised monosaccharides or as 2-O-sulfated residues. The glucosamine (GlcNAc) may be either N-sulfated or N-acetylated, or rarely exist as a free amine. N-sulfated-glucosamines may be O-sulfated at C3 (rarely), or at C6, or both C3 and C6, or carry no sulfates. Similarly, the N-acetylated glucosamines may be O-sulfated at C6 or unsulfated.

The present invention is predicated in part on the identification of chemical agents which inhibit interaction between a cell surface HLGAG and a cell-free or cell-associated ligand, or an extracellular HLGAG and a cell associated ligand, or an extracellular HLGAG and a cell-free ligand. Conveniently, the chemical agents are first identified using cell-free GAG molecules or a family of cell-free GAG molecules, which may be derived from naturally occurring HLGAGs or by a process of chemical modification of a non-GAG polysaccharide.

Up to the present time, particularly-convenient HLGAG molecules are heparan sulfate or heparin. Both heparan sulfate and heparin are a heterogenous mixture of different length molecules, having different sulfation patterns and where the uronic acid component of the repeating disaccharide HLGAG may also be iduronic acid. As a result of the heterogenous mixture, it is not readily apparent which fraction is responsible for interaction with a ligand. Consequently, it is not readily apparent which part of the molecule interacts with the ligand.

Reference to "GAGs" or a "population of GAGs" may mean one and the same entity. A GAG, therefore, may comprise a population of the same or different GAGs. Generally, however, the GAG represents a heterogenous population of GAG molecules including GAG-like molecules.

In a first embodiment, therefore, the present invention provides a method for generating libraries of GAG oligosaccharides, and methods for identifying GAG oligosaccharides or a part or region thereof which can bind to a ligand. The GAGs produced according to the methods of the present invention have application for treating any disease that involves interaction between GAG-like molecules and a ligand. Preferred diseases include inflammatory or allergic diseases and metastatic cancers and infection by a pathogenic agent.

Preferably, the ligand is a peptide, polypeptide or protein although the present invention extends to the ligand being a carbohydrate, lipid, glycoprotein or a molecule obtained from natural product screening or from a chemical library. Examples of protein ligands include, but are not limited to: a cytokine including an interleukin (e.g. IL-1, IL-2, IL-3, IL-4, IL-5, IL-6, IL-7, IL-8, IL-9, IL-10, IL-11, IL-12, IL-13, IL-14 or IL-15), interferon (e.g. α-interferon, β-interferon, γ-interferon) or a growth factor including but not limited to G-CSF, M-CSF, GM-CSF, BDNF, CNTF, EGF, EPO, FGF1, FGF2, FGF3, FGF4, FGF5, FGF6, FGF7, FGF8, FGF9, FGF10, FGF11, FGF12, FGF12, FGF13, FGF14, FGF15, FGF16, FGF17, FGF18, FGF19, FGF20, FGF21, FGF22, FGF23, LIF, MCP1, MCP2, MCP3, MCP4, MCP5, M-CSF, MIP1, MIP2, KC, NGF, NT 3, NT4, NT5, NT6, N17, OSM, PBP, PBSF, PDGF, PECAM-1, PF4, RANTES, SCF, TGFα, TGFβ$_1$, TGFβ$_2$, TGFβ$_3$, TNFα, TNFβ, TPO, VEGF, GH, insulin and the like; an enzyme; chemokines such as eotaxin (eotaxin-1, -2 or -3); or a soluble or cell- or virus-bound receptor.

The GAG oligosaccharides of the present invention can be generated from any of a number of polysaccharide polymers. In a preferred embodiment of the present invention, the polysaccharides contemplated as starting material include *E. coli* K5 polysaccharide or its equivalent from another prokaryotic or eukaryotic organism, chitin and/or chitosan. In addition, the starting material may be a polysaccharide of a different structure e.g. a dextran. Non-GAG polysaccharide based molecules and molecules that are composed of GAG-like sections (which may or may not be a GAG) linked by non-GAG structures are referred to herein as "GAG-composite molecules" or "composite molecules".

As used herein the terms "GAG-composite" structures or molecules or "composite" structures or molecules are used interchangeably. In one embodiment, a GAG-composite structure comprises a saccharide structure that binds a target protein. Preferably, the saccharide structure comprises two or more highly charged (eg. sulfated or phosphorylated) trisaccharides or disaccharides or tetrasaccharides or pentasaccharides or hexasaccharides or heptasaceharides or octasaccharides or any combination of these saccharides separated by a linker or linkers. It is preferable that the linker is not based on a GAG-like backbone. Rather, a linker such as an alkyl chain or a polyol structure, or polyethylene glycol is preferable. Further, it is not necessary for the highly charged saccharides to be based on GAG structures. Other sugars, such as a mannan, or chitosan, or dextran for example, may be used as the scaffold upon which to display the charged groups.

The oligosaccharides of the present invention are derived from these polymers via truncation and at least one deacetylation, sulfation, desulfation, phosphorylation and/or attachment of side chains.

It addition to just one of the above derivatizations, two, three, four or all five of the derivatization steps may be employed.

None of these derivatization steps needs occur in any particular order. Particular oligosaccharides are generated depending on the order and number of additional steps used in the preparation of the library.

Truncation of the polysaccharides into oligosaccharides can be achieved via a number of mechanisms. The truncating of the K5 capsular polysaccharide, for example, may be achieved at a variety of stages: on the natural polysaccharide, the de-N-acetylated polysaccharide or the sulfated polysaccharide. The methods employed to truncate the polysaccharide include enzymatic, chemical, thermal and ultrasonic protocols such as described by Alban and Franz, *Biomacromolecules* 2: 354, 2001.

Enzymatic truncation of the polysaccharide may also be possible at various stages. Heparinase III, Heparinase II and Heparinase I enzymes cleave the sulfalted K5 polysaccharide to give lower molecular weight fragments. Heparinase III may truncate the natural K5 polysaccharide to the desired length of polymerization (Nader et al., *Glycoconjugate Journal* 16: 265-270, 1999) β-D-glucuronidase and chondroitinase AC also degrade the natural unmodified K5 polysaccharide (Lidholt et al., *J. Biol. Chem.* 272: 2682, 1997.

The presence of an N-acetyl group on the glucosamine unit effectively protects this glycosidic linkage from cleavage when exposed to nitrous acid. The selective removal of the N-acetyl groups through the agency of hydrazine may be accomplished by methods known in the art. See, for example, Shaklee and Conrad, *Biochem. J.* 235: 225, 1986; Shively and Conrad, *Biochemistry* 15: 3932-3939, 1976; and Shaklee and Conrad, *Biochem. J.* 217: 187-197, 1984. The truncation of the K5 glucosamine-glucuronic acid polymer is then possible through the use of nitrous acid that enables the cleavage of an α-glycosidic bond of the glucosamine residue. By modifying the reaction conditions, it is possible to obtain varying sizes of K5 derived oligosaccharides. The use of size exclusion chromatography enables reasonable quantities of K5 derived DP 4-DP 20 to be obtained.

The presence of an N-acetyl group on the glucosamine unit within the chitin polysaccharide effectively protects this glycosidic linkage from cleavage when exposed to nitrous acid. The selective removal of the N-acetyl groups through the agency of hydrazine is a well known procedure. See Shaklee and Conrad, 1986, Supra; Shively and Conrad, 1976, Supra; and Shaklee and Conrad, 1984, Supra. The truncation of the hexosamine polymer is then possible through the use of nitrous acid that enables the cleavage of the α-glycosidic in heparan sulfate, dermatan sulfate, keratan sulfate and chondroitin sulfate. The chitosan glycosidic linkage is P and thus may give differing reactivity and cleavage reactions to the at glycosidic linkage.

The chemical sulfation of heparin-type oligosaccharide backbones has been extensively studied. Some degree of selectivity has been achieved using varied reaction conditions and the reactivity of certain hydroxyl groups has been determined (see Ogamo et al., *Carbohydr. Res.* 193: 165-172, 1989). Furthermore, some selectivity has been achieved by first per-sulfating the oligosaccharide and then selectively de-sulfating certain positions.

Investigations by the subject inventors, aimed at determining the degree of sulfation necessary for protein binding, have shown that some non-sulfated regions may improve the specificity of the GAG-Ligand binding event. In order to enable some control over the degree of sulfation of the oligosaccharides, controlled hydazinolysis is used by deliver a partially de-N-acetylated polysaccharide. The presence of an N-acetyl group confers protection upon the neighbouring glycosidic linkage during the nitrous acid cleavage and is not sulfated. Thus, the presence of some N-acetyl groups results in some non-sulfated regions throughout the oligosaccharide. The binding of sulfated GAGs and proteins in the anti-coagulation cascade is complex and the interaction of heparin with platelet factor IV (PF-IV) is something that has been problematic in some therapeutic applications. However, although the heparin-PF-IV interaction occurs at an extremely high affinity, the specificity is also high, thus by adding functionality that is non-detrimental to heparin binding and yet detrimental to PF-IV binding, some selectivity may be achieved. This is discussed by Petitou et al., 1999, Supra). This is achieved by minimizing the number of highly sulfated regions to 4-5 saccharide units on the termini and having a non-charged oligosaccharide spacer separating the charged sections.

The selective protection of the 6-OH is accomplished which then allows for the selective sulfation of the 2 and 4 hydroxyl groups. Alternatively, the 6-O sulfate is the most reactive and the most hydrolysed, giving another way to access the free 6-OH. Additionally, protection of the 2-amino group and the 3-hydroxyl group can be achieved using copper (II) ions allowing for the selective sulfation of the 6-OH (Terbojevich et al., *Makromol. Chem.* 190: 2847-2855, 1989.)

Additionally, the presence of free 6-OH groups is an opportunity to append further mono-, di- or tri-saccharides on to the free OH group giving a branched structure. Branched versions of β-1,3 glucan sulfates have been shown to display a higher anticoagulant activities than the corresponding linear versions with identical molecular weight and degree of sulfation (Alban and Franz, *Biomacromolecules* 2: 354-361, 2001). These attached saccharide units may be either sulfated or non-sulfated, or phosphorylated or non-phosphorylated as required.

Sulfation of K5, then hydazinolysis, to remove NHAc but leaving O-sulfation and N-sulfation intact, then selective N-sulfation, gives different sulfation patterns to deacetylation then N and O-sulfation of K5.

The chemical sulfation of chitosan type oligosaccharide backbones has been extensively studied. See, for example, Hirano et al., *Chitin. Nat. Tecnol., [Proc. Int. Conf. Chitin Chitosan]*, 3$^{rd}$ Ed., (Pub 1986) 461-468, 1985). Some selectivity is achieved by first per-sulfating the oligosaccharide and then selectively de-sulfating certain positions in analogous fashion to the heparan sulfate and K5 polysaccharide (Baumann et al., *Carbohydr. Res.* 308: 381-388, 1998).

In an alternate embodiment of the present invention, GAG oligosaccharides are generated by the method comprising size fractionating a population of heparin or heparan sulfate molecules or other polymers such as K5 polysaccharide, chitin or chitosan to generate non-full length fraction which interact with a ligand. Heparin comprises mixtures of glucuronic and iduronic acids in some of the disaccharide units and varying degrees of sulfation. Fractionation may be by any convenient means such as by gel filtration column and is based on different length saccharide chains generally but not exclusively from a DP4 to about a DP20 such as DP5, DP6, DP7, DP8, DP9, DP10, DP11, DP12, DP13, DP14, DP15, DP16, DP17, DP18 or DP19. Another form of separation is on the basis of extent of sulfation. The separation may also be based on a combination of these two parameters.

Another aspect of the present invention is the provision of novel phosphorylated GAG oligosaccharides. These molecules are generated by the inclusion of a phosphorylation step when generating the library of GAG oligosaccharides. This phosphorylation step and any associated desulfation steps that may be necessary, is performed on both the semi-synthetic oligosaccharides derived from polymers such as *E. coli* K5 polymer, chitin or chitosan, and oligosaccharides produced by fractionation of HLGAGs such as heparin or heparan sulfate.

The 6-O sulfate is the easiest O-sulfate to hydrolyse, giving a way to access free 6-OH. The free 6-OH is then phosphorylated to give the 6-O phosphate. The sulfate and phosphate esters have been shown to be equipotent in many compounds although in others phosphorylation changes the activity. It is also possible to N-phosphorylate the glucosamine residue.

The selective phosphorylation of a hydroxyl group is readily achieved using the phosphoramidate-oxidation method (Vieira de Almeida et al., *Tetrahedron* 55: 7251-7270, 1999; Dubreuil et al., *Tetrahedron* 55: 7573-7582, 1999 and references cited therein) This method has been widely employed for the formation of inositol phosphates, nucleotides and oligonucleotides. Alternatively, several other more rapid methods for the introduction of a phosphate group could be employed such as phosphoryl oxychloride in the presence of pyridine followed by aqueous hydrolysis. It may also be possible to enzymatically phosphorylate these oligosaccharides through the agency of a promiscuous hexose kinase enzyme.

Each oligosaccharide pool, as produced according to the methods described above, is then tested for its ability to interact or bind to a ligand. The ligand is chosen on the basis of the disease condition for which a therapeutic agent is sought. For example, IL-4 and IL-5 are useful ligands for allergic rhinitis and asthma, PECAM-1 is a useful ligand for inflammation and melanoma and gp120 or cyclophilin A are useful ligands for HIV infection. Clearly, any protein or non-protein ligand associated with a particular disease condition may be used.

Accordingly, another aspect of the present invention provides a method for identifying a population of GAG oligosaccharides that interact with a ligand.

The interaction with a ligand may be by any convenient means such as gel retardation, filter retardation, affinity co-electrophoresis, bioluminescent resonance energy transfer (BRET) assays, fluorescence resonance energy transfer (FRET assays, fluorescence polarisation (FP) assays, scintillation proximity assays or immobilization to biochips or other surfaces including those coupled with mass spectrometric detection.

The latter may be accomplished by first immobilizing the GAG oligosaccharide to a chip and then adding the ligand. Alternatively, the ligand may be immobilized to a chip and used to screen for the ability of a GAG oligosaccharide to bind thereto.

Yet another alternative is to immobilize a HLGAG, such as heparin, to a solid support and then screen for the ability of a GAG oligosaccharide, produced according to the methods above, to inhibit binding of a ligand to the immobilized heparin.

Accordingly, a particularly useful assay is to admix the ligand and the GAG oligosaccharide and screen for the ability for the GAG oligosaccharide to inhibit binding of the ligand to a HLGAG (e.g. heparin or heparan sulfate) bound to a chip.

Another aspect of the present invention contemplates, therefore, a method for producing GAG oligosaccharides or GAG-like composite molecules that interact with a ligand such as a protein, said method comprising producing a library of GAG oligosaccharides, or GAG-composite molecules and then screening each member of said library for an ability to interact with said ligand or to inhibit the interaction between the ligand and HLGAGs known to interact with said ligand.

In one preferred embodiment, the GAG oligosaccharide or GAG-like composite molecule binds a secreted cellular product which may be a protein and, in so doing, inhibits the interaction between the ligand and a HLGAG such as heparin.

There are, of course, any number of other assays, which may be used to screen for interaction between a GAG oligosaccharide or GAG-like composite molecule and a ligand or used to screen for inhibition of interaction between a ligand and a HLGAG known to bind to the ligand. Another assay is a filter binding assay. In this assay, one of a GAG oligosaccharide, or GAG-like composite molecule, or a ligand is labelled with a reporter molecule capable of providing an identifiable signal such as a fluorescent dye and both molecules are allowed to interact in solution. The resulting mixture is then passed through a filter capable of retarding one of the GAG oligosaccharide or GAG-like composite molecule or the ligand or only a GAG oligosaccharide-ligand complex or GAG-like composite molecule-ligand complex.

In one embodiment, for example, the filter is a nitrocellulose filter which retards proteins. In this case, if the GAG fraction, labeled with a reporter molecule, fails to pass through the filter, then the presence of the reporter signal in the filter indicates binding of the GAG to the protein.

In another embodiment, heparin or heparan sulfate is labeled with the reporter molecule and reacted with the protein in the presence of different GAG oligosaccharides or GAG-composite molecule. Passage of heparin or heparan sulfate through the filter is indicative of a GAG oligosaccharide or GAG-like composite molecule that has inhibited the interaction between the heparin/heparan sulfate and the protein.

Different GAGs will interact with different ligands, or different ligands will interact with different GAGs or both. Accordingly, another assay involves the use of affinity columns carrying immobilized ligands. The GAG oligosaccharides or GAG-like composite molecules are then passed through the column and the presence of retardation of the GAG oligosaccharides determined. A salt gradient is conveniently used to elute bound GAG oligosaccharides or GAG-like composite molecules. Once a fraction that binds to a ligand on a column is identified, the fraction can be further analyzed to obtain an indication of the number of different structural entities therein. Such analysis may comprise, for example, anion exchange chromatography, mass spectrometry or electrophoresis.

The present invention is not limited to any particular order of the steps described herein.

In relation to this latter embodiment, in one example, fractions of heparin are tested on an IL-5 affinity column. A fraction comprising GAG oligosaccharides of DP12 has been determined in accordance with the present invention to bind to IL-5. More specifically, subsequent anion exchange chromatography of the said DP12 fraction revealed that only a subset of the structures within the total DP 12 fraction/pool bound IL-5. It is likely that there are separate entities within the subset of structures that bind IL-5 and that these separate entities differ in their patterns of sulfation.

In another example, fractions of heparin are tested on an affinity column prepared by immobilizing IL-4. A fraction comprising GAGs of DP10 has been determined in accordance with the present invention to bind to IL-4. Subsequent anion exchange chromatography of the DP10 fraction revealed that only a subset of the structures within the total DP10 fraction bound IL-4. From mass spectrometric analysis it is evident that these structures differ in their pattern of sulfation.

The heparin-binding site on IL-4 and the site on IL-4 required for binding to IL-4R alpha are proposed to overlap. This is important for targeting and functional analysis.

Once GAG oligosaccharides that bind to a particular ligand have been identified, this fraction itself may be useful as a therapeutic to inhibit interaction between a protein (or other ligand) and a cell surface HLGAG (e.g. heparin or heparan sulfate). The protein (or other ligand) may be cell free or associated with a cell or virus such as a cell surface or viral surface. The said GAG oligosaccharide may also be useful as a therapeutic to modulate interaction between a secreted cellular product and extracellular matrix components or between a cell surface protein and extracellular matrix components, or between a protein and its ligand, both or either of which may be cell surface or cell associated. Alternatively, the GAG oligosaccharide may be used as a target to identify natural products or products from a chemical library that mimic the GAG oligosaccharide in terms of binding to a ligand or that inhibits or promotes the interaction between the HLGAG and the ligand. These molecules may be antagonists or agonist or chemical analogs of the GAG. Hence, an "analog" extends to and encompasses any structure which is functionally equivalent in that it binds and/or modulates a ligand in an analogous manner.

Reference herein to "modulate" or "modulation" extends to and encompasses inhibiting and/or promoting in interaction.

Accordingly, another aspect of the present invention is directed to a method for generating a medicament for treating a disease condition in a subject, said method comprising producing a range of GAG oligosaccharides or GAG-like composite molecules according to the method of the invention, and screening each GAG for an ability to interact with or modulate the ligand. The GAG oligosaccharide that interacts with or modulates the ligand is identified and using same or an analog, agonist or antagonist thereof in the manufacture of said medicament.

In one preferred embodiment, the modulation is an inhibition.

Types of ligands contemplated herein include those listed above such as PECAM-1, Cyclophilin A, gp120 and cytokines such as interleukin (IL)-1, 2, 3, 4, 5, 6, 7, 8, 10, 11, 12 and 13, G-CSF, GM-CSF, LIF, and M-CSF and chemokines such as eotaxin-1, eotaxin-2 and eotaxin-3. The diseases contemplated herein include allergic rhinitis, asthma, atopic dermatitis and other allergic diseases, HIV (human, canine, feline, equine, etc.), inflammatory diseases, deep vein thrombosis and melanoma and other cancers.

The subjects to be treated include humans, livestock animals (e.g. cattle, sheet, pigs, horses, donkeys), laboratory test animals (e.g. rabbits, guinea pigs, mice, rats) and companion animals (e.g. dogs, cats).

Yet another aspect of the present invention contemplates a method of treatment of a disease condition in a subject, said disease condition resulting from interaction between a HLGAG on a surface of a cell in said host and a ligand, or a HLGAG in the extracellular matrix in said host and a ligand that may or may not be cell associated, or a protein-ligand interaction in said host that can be disrupted by a HLGAG where the protein may be cell associated and the ligand soluble or both protein and ligand may be cell associated, said method comprising administering to said subject an effective amount of a medicament, said medicament being a GAG oligosaccharide, produced and identified according to the invention, that interacts with said ligand and incorporating said fraction into a medicament or obtaining a chemical analog or homolog thereof and incorporating same into said medicament.

Another aspect of the present invention provides a composition comprising one or more of:
(i) A GAG oligosaccharide as defined herein;
(ii) A GAG-like composite molecule as defined herein;
(iii) A GAG oligosaccharides, GAG-like oligosaccharide, GAG-like composite molecule or non-GAG or non-GAG-like molecule as defined herein;
(iv) an agonist of (i), (ii) or (iii);
(v) an antagonist of (i), (ii) or (iii);
(vi) a chemical analog, homolog or ortholog of (i) or (ii) or (iii) or (iv) or (v); and/or
(vii) a natural or chemical library analog, homolog or ortholog of (i), (ii), (iii), (iv), (v) and (vi).

The composition also comprises one or more pharmaceutically acceptable carriers and/or diluents.

All such agents above are referred to as "active ingredients" and the compositions are proposed for use as pharmaceuticals.

The pharmaceutical forms suitable for injectable use include sterile aqueous solutions (where water soluble), sterile powders for the extemporaneous preparation of sterile injectable solutions and inhalable forms. Such forms are preferably stable under the conditions of manufacture and storage and are generally preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active ingredients in the required amount in the appropriate solvent with the active ingredient and optionally other active ingredients as required, followed by sterilization or at least a process to reduce contaminating viruses, bacteria or other biological entities to acceptable levels for administration to a human or animal subject. In the case of sterile powders for the preparation of sterile injectable solutions, suitable methods of preparation include vacuum drying and the freeze-drying technique that yields a powder of active ingredient plus any additionally desired ingredient.

When the active ingredient is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per second, minute, hour, day, week, month or year.

The tablets, troches, pills and capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, anti-bacterial and anti-fungal agents, isotonic and absorption delaying agents and the like. The use of such media and agents for pharmaceutical active substances is well known in the art and except insofar as any conventional media or agent is incompatible with the active ingredient, their use in the therapeutic compositions is contemplated. Supplementary active ingredients can also be incorporated into the compositions.

The composition may also be formulated for local or topical administration. Techniques formulation and administration may be found in "Remington's Pharmaceutical Sciences", Mack Publishing Co., Easton Pa., 16th edition, 1980, Ed. By Arthur Osol. Thus, for local or topical administration, the subject compositions may be formulated in any suitable manner, including, but not limited to, creams, gels, oils, ointments, solutions, suspensions, powders, mists or aerosols. For transmucosal administration, penetrants appropriate to the barrier to be permeated are used in the formulation. Such penetrants are generally known in the art and include, but are not restricted to, benzalkonium chloride, digitonin, dihydrocytochalasin B, and capric acid.

The compositions of the subject invention in the form of lotions, creams or gels may contain acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, buffering agents, cellulose derivatives, emulsifying agents such as nonionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

In one particularly preferred embodiment, the present invention contemplates an inhalant pharmaceutical composition.

Once the GAG oligosaccharide or GAG-like composite molecule is identified that binds to a particular ligand, or a chemical analog is obtained or a natural product analog obtained where it acts in a similar manner as the GAG oligosaccharide, or acts as an agonist or antagonist, it may be useful to generate immunological reagents capable of interacting with the particular molecule or group of molecules. It may also be useful to generate immunological reagents in which the antigenic region corresponds to the HLGAG binding region of the ligand or part thereof. The preferred immunological reagents are antibodies and these are particularly useful for use in immunoassays. Such immunoassays can be useful to monitor levels of the target agents, to purify the target agents or to inhibit the function of the target agents.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques that are well known to those who are skilled in the art. (See, for example, Douillard and Hoffman, Basic Facts about Hybridomas, in *Compendium of Immunology* Vol. II, ed. by Schwartz, 1981; Kohler and Milstein, Nature 256: 495-499, 1975; Kohler and Milstein, *European Journal of Immunology* 6: 511-519, 1976).

Another aspect of the present invention contemplates a method for detecting a HLGAG fraction in a sample, said method comprising contacting said sample with an antibody specific for said HLGAG fraction or its homologs or analogs for a time and under conditions sufficient for an antibody-HLGAG complex to form, and then detecting said complex.

In the description below, the "HLGAG" molecule or its analogs or homologs is referred to as the "antigen". The HLGAG molecule or its analogs or homologs may also be detected using labeled proteins that bind to HLGAGs or their analogs or homologs. Ideal proteins for this application are avidin or lactoferrin. These proteins may be labeled with a fluorescent derivative such as fluorescein or Alexafluor 488.

The detection of a HLGAG fraction may be accomplished in a number of ways such as by Western blotting and ELISA procedures. A wide range of immunoassay techniques are available as can be seen by reference to U.S. Pat. Nos. 4,016,043, 4,424,279 and 4,018,653.

Sandwich assays are among the most useful and commonly used assays and are favoured for use in the present invention. A number of variations of the sandwich assay technique exist, and all are intended to be encompassed by the present invention. Briefly, in a typical forward assay, an unlabeled antibody is immobilized on a solid substrate and the sample containing the antigen to be detected to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of antigen. Variations on the forward assay include a simultaneous assay, in that both sample and labeled antibody are added simultaneously to the bound antibody. These techniques are well known to those skilled in the art, including any minor variations as will be readily apparent.

The solid surface is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay.

By "reporter molecule", as used in the present specification, is meant a molecule that, by its chemical nature, provides an analytically identifiable signal that allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state to excitability in the molecule, followed by emission of the light at a characteristic color visually detectable with a light microscope. As in the EIA, the fluorescent labeled antibody is allowed to bind to the first antibody-antigen complex. After washing off the unbound reagent, the remaining tertiary complex is then exposed to the light of the appropriate wavelength, the fluorescence observed indicates the presence of the antigen of interest. Immunofluorescene and EIA techniques are both very well established in the art and are particularly preferred for the present method. However, other reporter molecules, such as radioisotope, chemiluminescent or bioluminescent molecules, may also be employed.

In addition, the presence of the GAG may be detected indirectly by using antibodies recognizing the GAG binding region of the ligand or part thereof to assay the proportion of the GAG binding sites remaining on exogenous ligand.

There is considerable interest in the heparin binding sites on a wide range of different types of proteins and there have been a number of attempts to describe heparin binding motifs in protein primary sequences. Cardin and Weintraub first described heparin binding motifs as XBBBXXBX and XBBXBX, where B is a basic residue and X a hydropathic residue (Cardin and Weintraub, *Arteriosclerosis* 9: 21-32, 1989). Hileman et al. extended these motifs to include turns that bring basic interacting residues into proximity and described a new consensus sequence, TXXBXXT-BXXXTBB, where T is a turn (Hileman et al., *Bioessays* 20: 156-67, 1998). However, these motifs are not appropriate for all proteins as a GAG binding site is determined by the solution structure of the protein and heparin binding sites show no absolute dependency on specific sequences or protein folds. It is the sulfates on the heparin that interact with basic patches appropriately arranged on the surface of the protein. As the distance between sulfate clusters along one side of the heparin helix in solution is 17 Å, two patches of basic residues with a spacing between them of 17 Å on the surface of the protein in solution is a good starting point towards locating a heparin binding site (Mulloy and Forster, *Glycobiology* 10: 1147-56, 2000).

In order to identify GAG-binding regions on a target protein, it is necessary to characterize the primary, secondary, tertiary and quaternary structure of the protein. This would require a consideration of, inter alia:
1. Number and position of acidic/basic residues.
2. Number and position of polar/non-polar residues.
3. Number and position of charged/uncharged residues.
4. Number and position of hydrophobic/hydrophillic residues.
5. Number and position of naturally occurring chemical modifications of residues i.e. hydroxylation, phosphorylation, methylation, acetylation, formylation, carbohydrate addition, lipid addition and covalent attachment of cofactors such as pyridoxal-5-phosphate and hemes.

6. Number and position of covalent and non-covalent bonding i.e. disulfide bonds, hydrogen bonds, ionic bonds, hydrophobic bonds, Van der Waals forces etc.
7. Physical distance between individual and/or groups of residues.
8. Stereoisomerism of residues.
9. Number and position of α-helical and β-sheet formations.
10. Potential to form homodimers and heterodimers.

Further, the features of the carbohydrate binding partner (eg. GAG) may also be characterised with regard to features such as:
1. Chain length i.e. Extent of polymerisation.
2. Side chain modification.
3. Stereoisomerism.
4. Number and position of ring structures.
5. Number and position of glcosidic bonds.
6. Secondary structure if present, i.e. helix.

In analysing the features of protein and carbohydrate binding partners the methods used could include:
1. Comparative sequence analysis.
2. Yeast two-hydrid study.
3. Co-immunoprecipitation and other affinity methods.
4. Nuclear magnetic Resonance (NMR).
5. X-ray crystallography.
6. Computer modelling.
7. Site-directed mutagenesis and domain deletion studies.
8. Chemical cross-linking of the ligand to GAGs.

Domain deletion analysis is a low-resolution method that is used on large proteins, such as PECAM-1, to ascertain the general regions on the protein that are important for binding to GAGs. Domain deletion involves the truncation of the DNA coding sequence of a protein, such that the expressed protein is shortened by a defined length. A series of domain deletions over the length of the whole molecule are screened for their ability to bind to GAGs, using assays described in this document. Regions that contain GAG binding sites will bind GAGs, but those that have the site deleted will not. By examining the domain deletions that abrogate HLGAG binding, a relatively small region on the overall protein can be identified as being important for GAG binding [Conrad, 1998, Supra]. This region can be expressed in isolation for further analyses such as site directed mutagenesis or NMR studies.

Site directed mutagenesis involves the mutation of one or nucleotides within the DNA coding sequence of a protein, such that the expressed protein is altered in at least one amino acid. The mutant can then be screened in the heparin-binding assays described in this document for the effect on heparin binding. Mutants that affect heparin binding can be mapped on two or three dimensional protein models to ascertain their position in relation to each other, and to the protein as a whole. This technique can be used on any GAG-binding protein to gather information on any GAG-binding site on that protein [Tsiang, et al., *J. Biol. Chem.* 270: 16854-16863, 1995].

NMR is used to gather three-dimensional structural information on proteins and other molecules. The molecule to be studied is labeled with non-radioactive isotopes such as $^{13}C$ and $^{15}N$, after which the molecule is subjected to strong magnetic fields. The behaviour of the molecule in these fields is used to gather structural information on the molecules in question. To determine the GAG binding sites on proteins using NMR, the structure of the protein without the GAG is first determined. Then the structure is determined in the presence of GAG, and the two structures are compared. The amino acids whose structure is most perturbed are likely to be the amino acids that are bound to GAGs. NMR studies can be done on proteins of molecular weight less than 20 kDa, such as IL-4 and single domains of PECAM-1 [Chuang et al., *Biochem.* 39: 3542-3555, 2000].

Other methods for the determination of binding sites include competitive inhibition of binding using peptides that mimic putative heparin-binding sequences within the target protein. These may be derived by peptide synthesis, or by cleavage of the target protein by particular endoproteinases or chemicals such as cyanogen bromide. The peptides can then be purified by reversed phase HPLC [Conrad, 1998, Supra]. Alternatively, GAGs can be directly cross-linked to proteins under certain conditions. Carboxylate groups of uronic acids are activated with N-hydroxysuccinimide esters in the presence of a carbodiimide catalyst. The activated GAGs are bound to the target protein. Covalent cross-linking will occur if the activated GAG binds to a protein whose GAG binding site contains lysines within a close proximity [Lyon, et al, *J. Biol Chem.* 277(2): 1040-1046, 2002]. The HLGAG-protein complex can be examined for the site(s) of modification to elucidate which lysines within the protein are cross-linked to the GAG chains. These lysines can be mapped on two or three dimensional protein models to ascertain their position on the protein, in relation to other basic amino acids that might be candidates for contribution to GAG binding.

Accordingly, the present invention provides a method of identifying GAG-binding regions on a ligand of interest, said method comprising obtaining one or more variant forms of the ligand and comparing the binding of said variant form of the ligand to a GAG molecule, with the binding of a wild-type ligand to the same GAG molecule, wherein a reduction in binding affinity between the variant ligand and the GAG molecule compared to the binding of the wild-type ligand to the same GAG molecule is indicative of the variant form of the ligand comprising an alteration in the GAG-binding site of the ligand.

Preferably, the ligand of interest is a protein, even more preferably, the protein is a cytokine, an interleukin, an interferon or a soluble or cell- or virus-bound receptor.

As used herein the term "variant" with respect to a ligand of interest refers to any form of a ligand molecule which is structurally different or distinct from the wild-type ligand of interest to which the variant is compared for binding affinity. Examples of structural variations contemplated by the present invention are presented. Preferably, the ligand is a proteinaceous molecule and in this embodiment of the method, a "variant" ligand includes a protein which comprises one or more amino acid insertions, deletions or substitutions with respect to the wild-type of the protein. Such amino acid substitutions may also be comprised by a domain insertion, deletion or substitution in the variant protein ligand.

The present invention further extends to a site on a ligand and in particular a linear or conformational structure with which a GAG or part thereof interacts.

The present invention further provides GAG oligosaccharides, GAG-like oligosaccharides, GAG-like composite molecules or non-GAG or non-GAG-like molecules which bind to the same target site on a peptide, polypeptide or protein to which a GAG oligosaccharide binds.

The present invention is further described by the following non-limiting Examples.

EXAMPLE 1

Generation of a Library of DP 4-DP 20 Oligosaccharides from *E. coli* K5 Polymer Tailoring the Length of the *E. coli* K5 Polymer The truncating of the K5 capsular polysaccharide is achieved at one of a variety of stages: on the natural polysaccharide, the de-N-acetylated polysaccharide or the sulfated polysaccharide. The methods employed to truncate the polysaccharide include enzymatic, chemical, thermal and ultrasonic protocols. (Alban and Franz, 2001, Supra).

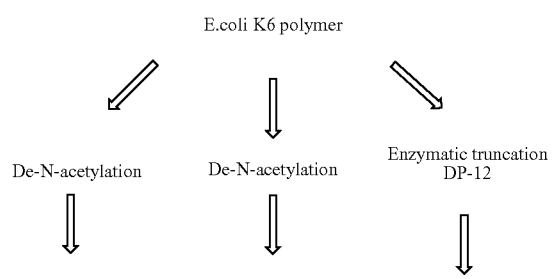

Enzymatic Truncation

Enzymatic truncation of the polysaccharide is also possible at various stages. Heparinase III, Heparinase II and Heparinase I enzymes cleave the sulfated K5 polysaccharide to give lower molecular weight fragments. Heparinase III truncates the natural K5 polysaccharide to the desired length of polymerization (Nader et al., 1999, Supra). β-D-glucuronidase and chondroitinase AC will degrade the natural unmodified K5 polysaccharide (Lidholt et al., 1997, Supra).

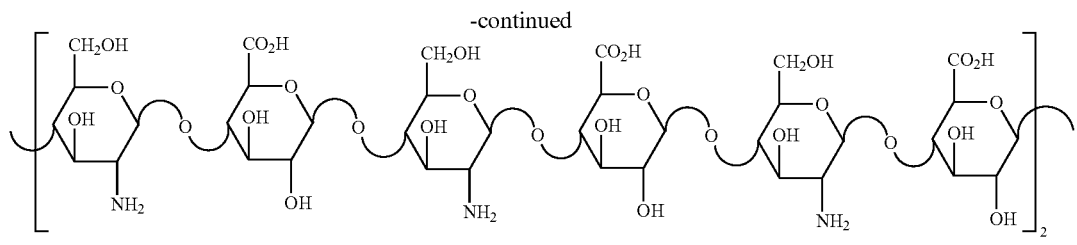
K5 de-N-acetylated DP-12

| Sulfation or phosphorylation

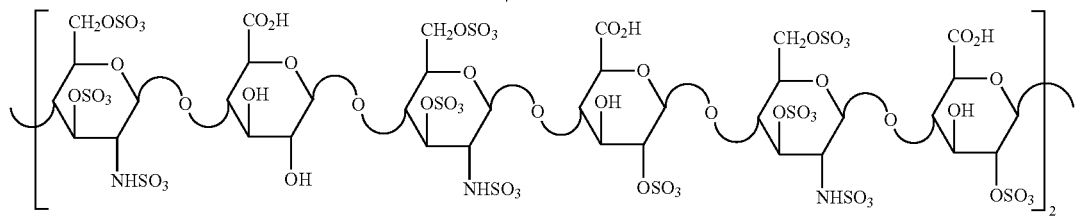

Chemical Truncation

The presence of an acetyl group on the glucosamine unit effectively protects this glycosidic linkage from cleavage when exposed to nitrous acid. The selective removal of the N-acetyl groups through the agency of hydrazine is well known to those in the art (Shaklee and Conrad, 1986, Supra; Shively and Conrad, 1976, Supra; Shaklee and Conrad, 1984, Supra). The truncation of the glucosamine-glucuronic acid polymer is possible through the use of nitrous acid that enables the cleavage of an α-glycosidic bond of the glucosamine residue. By modifying the reaction conditions it is possible to obtain varying sizes of K5 derived oligosaccharides and size exclusion chromatography is used to obtain reasonable quantities of K5 derived DP 4-DP 20 oligosaccharides.

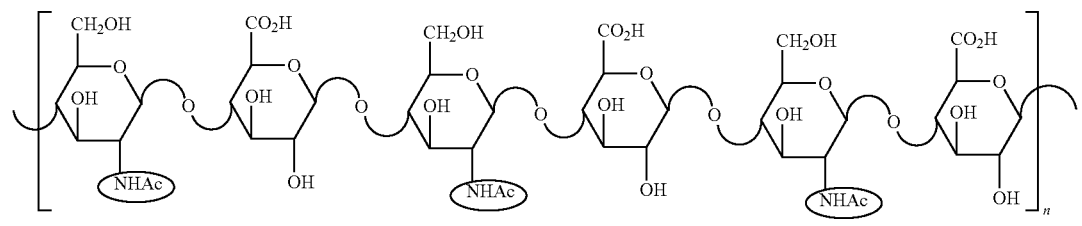
E.coli K5 capsular polysaccharide

| hydrazine hydrolysis, 1%, 100 C.

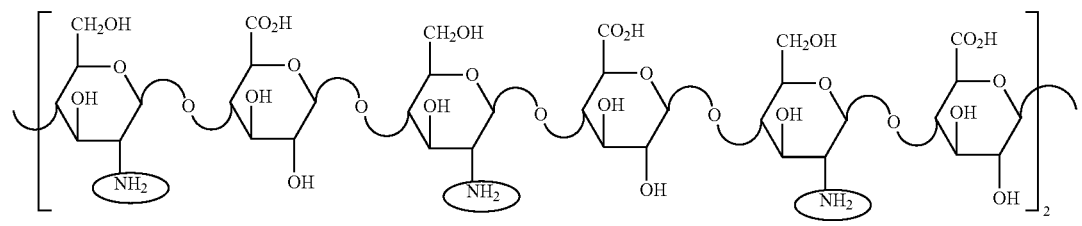
E.coli K5 de-N-acetyl polysaccharide

| Nitrous acid degradation, pH 4

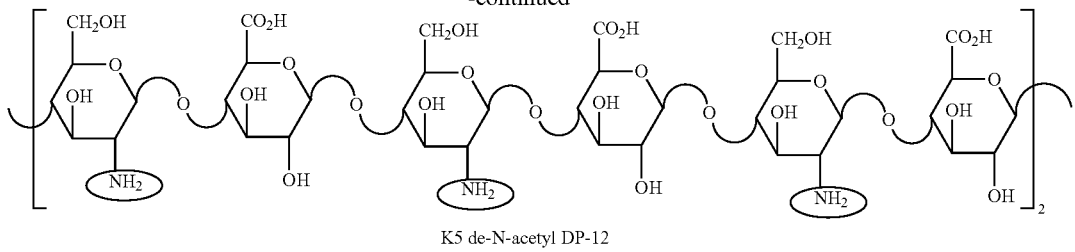

K5 de-N-acetyl DP-12

Sulfation,
SO₃:pyridine complex

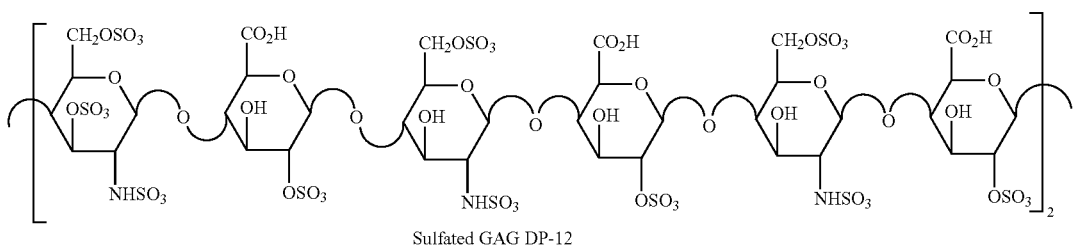

Sulfated GAG DP-12

Sulfation of the *E. coli* K5 Oligosaccharide/Polysaccharide

Preliminary investigations aimed at determining the degree of sulfation necessary for protein binding, have shown that some non-sulfated regions may improve the specificity of binding. In order to enable some control over the degree of sulfation of the DP12 oligosaccharide, controlled hydazinolysis is used to deliver a partially de-N-acetylated polysaccharide. The presence of an N-acetyl group confers protection upon the neighbouring glycosidic linkage during the nitrous acid cleavage and would not be sulfated. Thus, the presence of some N-acetyl groups result in some non-sulfated regions throughout the oligosaccharide.

Those of skill in the art are aware of methods for the selective protection of the 6-OH that then allows for the selective sulfation of the 2 and 4 hydroxyl groups. Alternatively, the 6-O sulfate is the most reactive and the most hydrolyzed, giving another way to access the free 6-OH.

Additionally, the presence of free 6-hydroxyl groups provides an opportunity to append further mono-, di- or trisaccharides on to the free hydroxyl group giving a branched structure. Branched versions of β-1,3 glucan sulfates have been shown to display a higher anticoagulant activities than the corresponding linear versions with identical molecular weight and degree of sulfation (Alban and Franz, 2001, Supra) These attached saccharide units could be either sulfated or non-sulfated, or phosphorylated or non-phosphorylated.

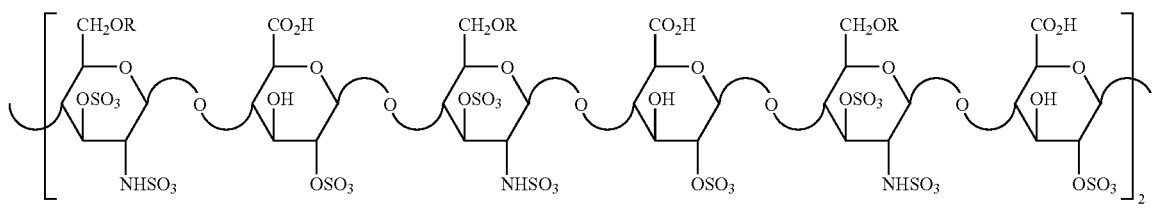

K5 6-OH modifications DP-12

R = H, SO₃, PO₃²⁻, sugar moiety, alkyl group, protecting group.

Other Chemical Modifications

Sulfation of K5, then hydazinolysis, to remove NHAc (but leave O-sulfation and N-sulfation intact), then selective N-sulfation, can be utilized to give different sulfation patterns to deacetylation then N and O-sulfation of K5.

EXAMPLE 2

Generation of a Library of DP4-DP20 Oligosaccharides from Clitosan

Tailoring the Length of the Chitosan Polysaccharide

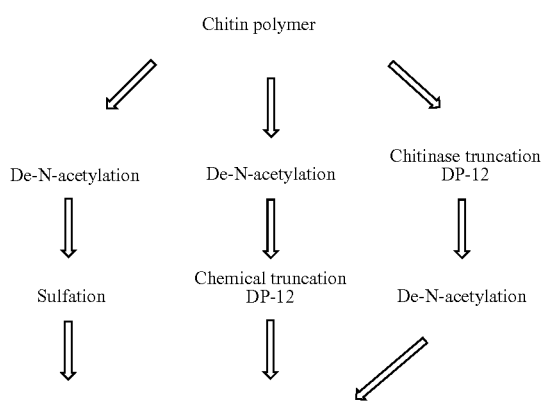

-continued

Sulfated DP-12 ligand with anti-inflammatory properties

Enzymatic Truncation

The enzymatic degradation of chitin and chitosan using chitinase enzymes is well understood [Horwitz et al., *Chitin, Chitosan and related enzymes*, Zikakis J., (ed.) Academic Press, Orlando, Fla. (1984)].

Chemical Truncation

The presence of an acetyl group on the glucosamine unit within the chitin polysaccharide effectively protects this glycosidic linkage from cleavage when exposed to nitrous acid. The selective removal of the N-acetyl groups through the agency of hydrazine is a well known procedure (Shaklee and Conrad, 1986, Supra; Shively and Conrad, 1976, Supra; Shaklee and Conrad, 1984, Supra).

The truncation of the glucosamine polymer is then achieved through the use of nitrous acid that enables the cleavage of the α-glycosidic in heparan sulfate, dermatan sulfate, keratan sulfate and chondroitin sulfate. The chitosan glycosidic linkage is β and thus gives differing reactivity and cleavage reactions to the α glycosidic linkage. However this has been described on truncated sulfated chitosan fragments (Terbojevich et al. 1989, Supra).

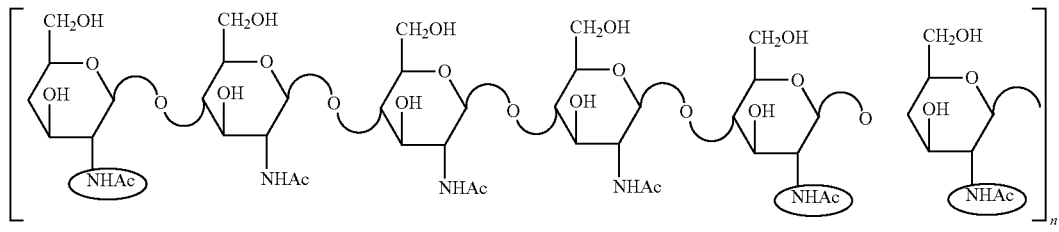

Partial hydrazine hydrolysis

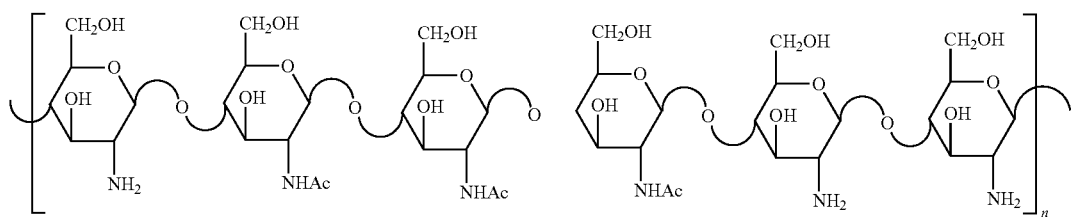

Nitrous acid truncation

-continued

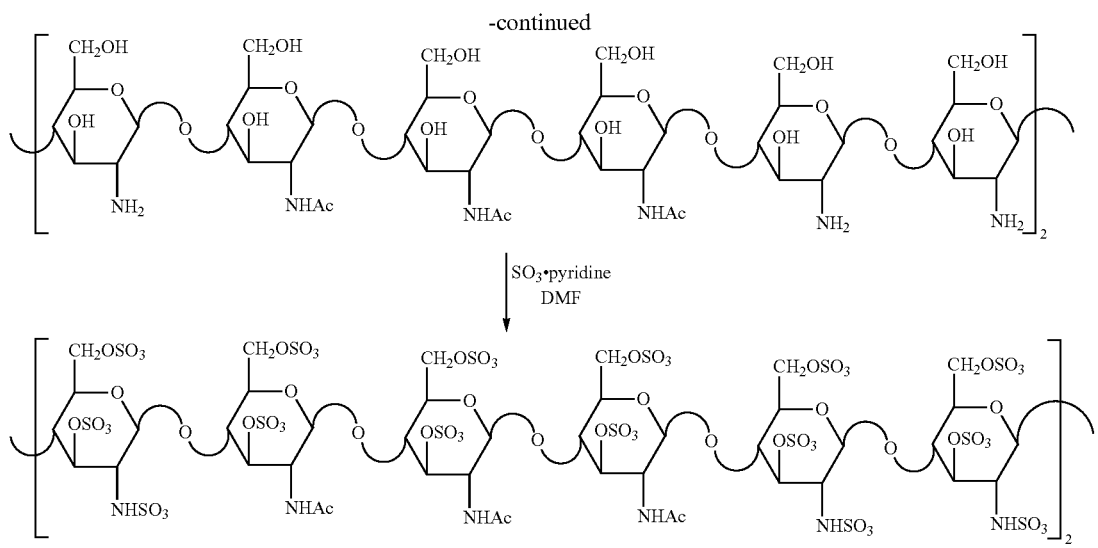

Sulfation of the Chitosan Polysaccharide

The chemical sulfation of chitosan type oligosaccharide backbones has been extensively studied (Hirano et al., 1985, Supra) Some selectivity is achieved by first per-sulfating the oligosaccharide and then selectively de-sulfating certain positions in analogous fashion to the heparan sulfate and K5 polysaccharide (Baumann et al., 1998, Supra). Additionally, protection of the 2-amino group and the 3-hydroxyl group is also achieved using copper (II) ions allowing for the selective sulfation of the 6-OH (Terbojevich et al., 1989, Supra).

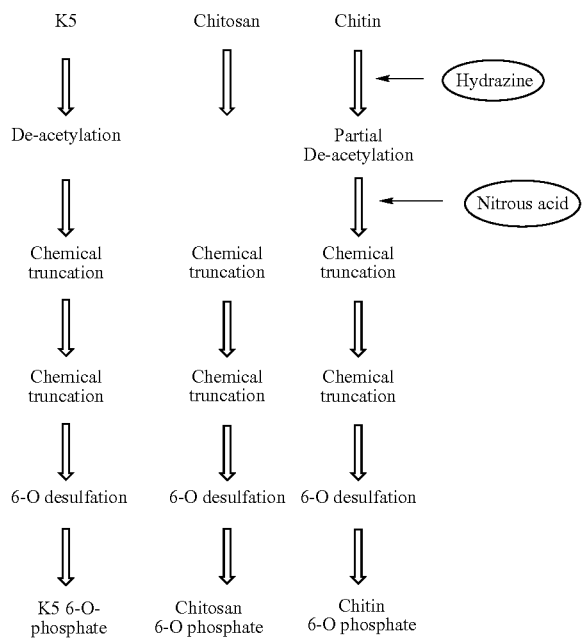

Investigations aimed at determining the degree of sulfation necessary for protein binding, have shown that some non-sulfated regions may improve the specificity of binding. In order to enable some control over the degree of sulfation of the DP12 oligosaccharide, controlled hydazinolysis delivers a partially de-N-acetylated polysaccharide. The presence of an N-acetyl group will confer protection upon the neighboring glycosidic linkage during the nitrous acid cleavage and would not be sulfated. Thus, the presence of some N-acetyl groups will result in some non-sulfated regions throughout the oligosaccharide.

EXAMPLE 3

Phosphorylation of GAG Oligosaccharides

6-O sulfate is the easiest O-sulfate to hydrolyze, providing a way to access the free 6-OH. The free 6-OH is then phosphorylated to give the 6-O phosphate. Sulfate and phosphate esters have been shown to be equipotent in many compounds. It is also possible to N-phosphorylate the glucosamine residue.

The selective phosphorylation of a hydroxyl group is readily achieved using the phosphoramidate-oxidation method. (Vieira de Almeida et al., 1999, Supra; Dubreuil et al., 1999, Supra and references cited therein). This method has been widely employed for the formation of inositol phosphates, nucleotides and oligonucleotides. Alternatively, several other more rapid methods for the introduction of a phosphate group could be employed such as phosphoryl oxychloride in the presence of pyridine followed by aqueous hydrolysis. It is also be possible to enzymatically phosphorylate these oligosaccharides through the agency of a promiscuous hexose kinase enzyme.

EXAMPLE 4

Preparation of a Library of Heparin and Heparan Sulfate Oligosaccharides

HLGAGs may be partially digested by a number of means, including enzymatic digestion with heparinases and chemical digestion using agents such as nitrous acid, alkaline β-elimination and oxidation in conjunction with alkaline depolymerisation [Conrad, 1998, Supra]. The enzymes heparinase I and heparinase III cleave at specific sites on the heparin/heparan sulfate chain: heparinase I at IdoA residues with N-sulfated glcN domains, and heparinase III at GlcA residues in unsulfated N-acetyl GlcN domains.

Heparan sulfates are depolymerized according to the procedures described by Turnbull et al. (*Proc. Natl. Acad. Sci.*

USA 96(6): 2698-2703, 1999), Heparin was depolymerized in accordance with the procedure described by Chai et al. (*Anal. Chem.* 70(10): 2060-2066, 1998). Briefly, heparin (5 g) and albumin (4 mg) were dissolved in 50 ml 30 mM $CH_3CO_2NTa$, containing 3 mM $CaCl_2$ and adjusted to pH 7 with 0.2 M $NaHCO_3$. Heparinase I, EC 4.2.2.7, (2 IU) was added and the mixture incubated at 30° C. for 16 hrs. The mixture was boiled for 3 minutes, aliquoted into small volumes (5 ml) and frozen. Aliquots were thawed, centrifuged and filtered before injection (1 ml) on the size-exclusion chromatography system.

Figure 1:
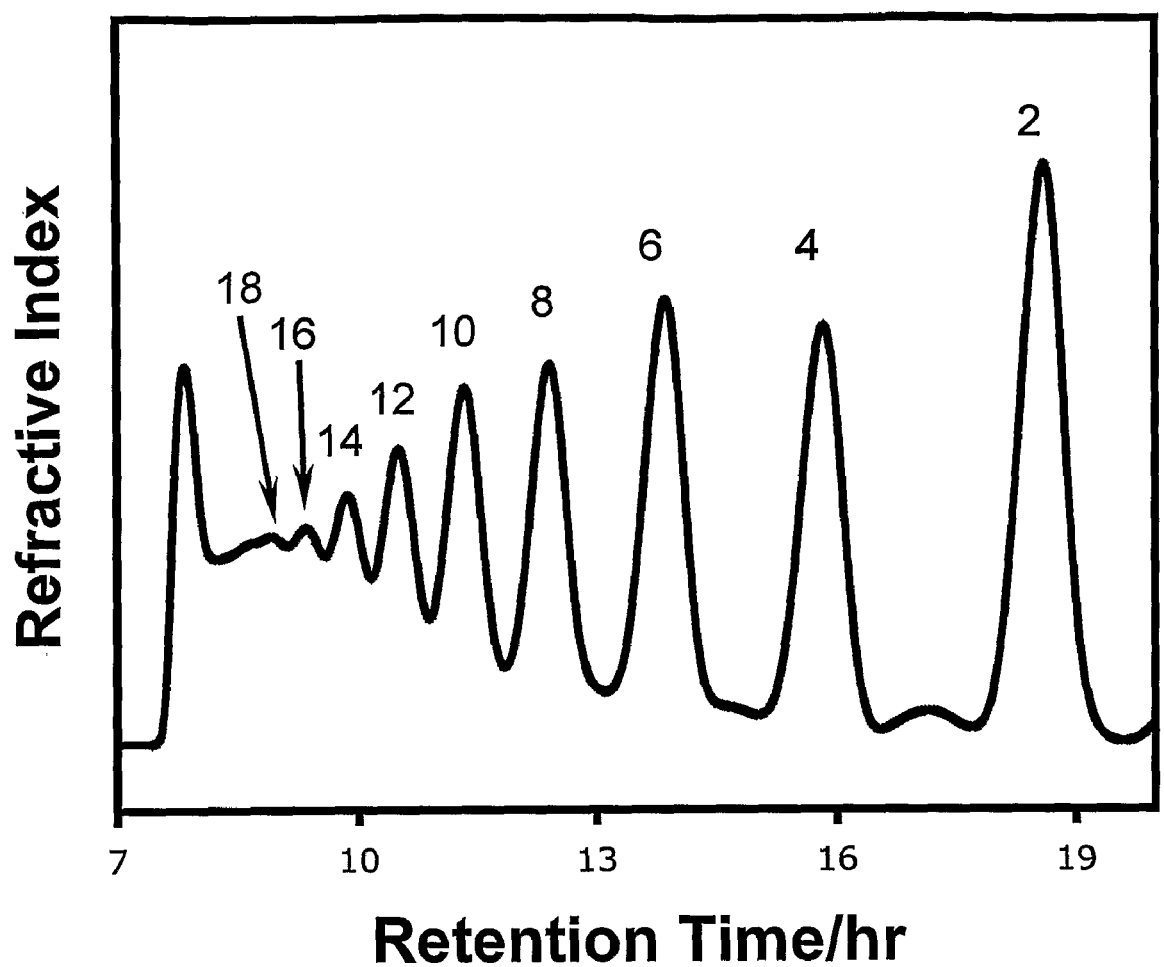
FIG. 1 is a graphical representation showing size exclusion chromatogram of the partial heparinase I digest of heparin. The numbers at the peak apices refer to the DP.
Figure 2A:
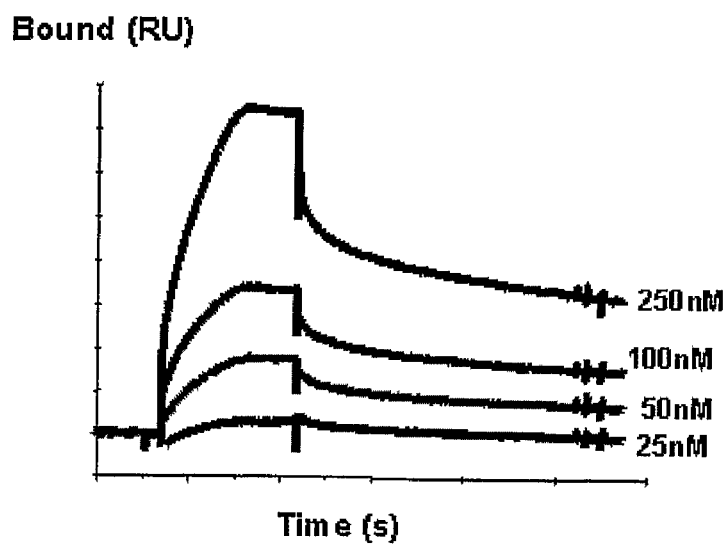
FIG. 2A-2D are graphical representations showing BIAcore HLGAG-binding assay. Proteins at the concentrations indicated were injected over heparin immobilized onto streptavidin sensor chips. The binding data were monitored during both the association and dissociation phases. Panel A, rhIL-4. Panel B, rhIL-5. Panel C, flag-PECAM-1. Panel D, CypA.
Figure 2B:
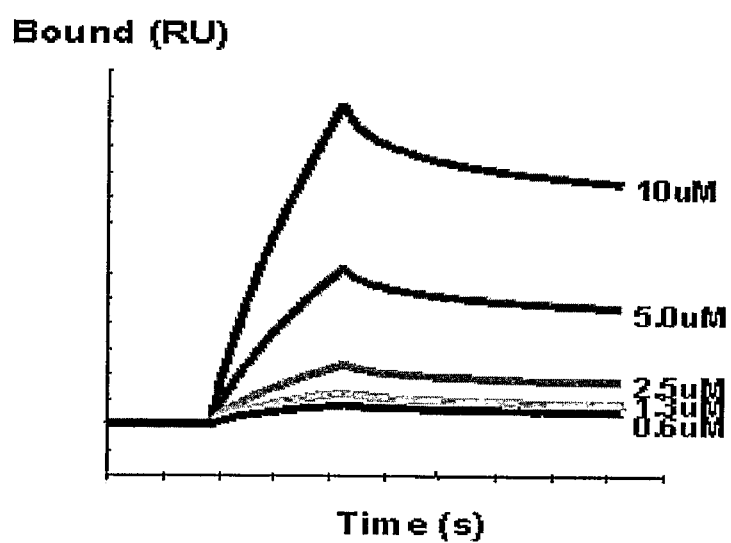
Figure 2C:
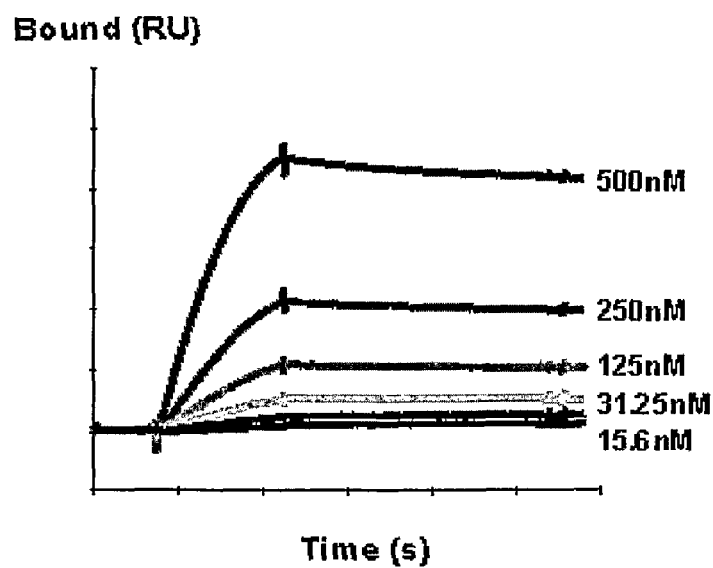
Figure 2D:
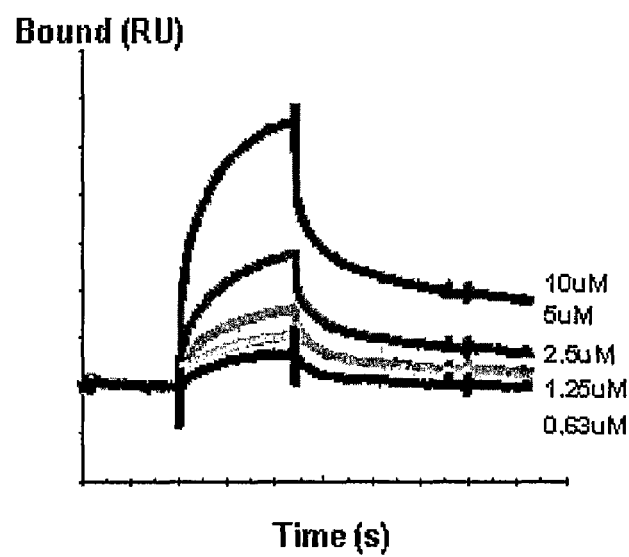

SEC was performed on a two 90×1.5 cm glass columns connected in series. The first column was packed with P6 fine and the second with P10 fine. The columns were eluted with 0.25 M NaCl at a flow rate of 0.25 ml/min using a Gilson model 307 titanium pump (Middleton, Wis., USA) and the effluent monitored with a Shimadzu RID-10 refractive index detector (Melbourne, Victoria, Australia). Data was acquired using Gilson Unipoint software. A representative chromatogram is shown in FIG. 1. Fractions of 1 ml were collected. Fractions adjacent to the peak maxima were pooled, lyophilized and desalted on a fast desalting column. The desalted fragments were lyophilized, redissolved in water and stored at −20° C. The concentration of each fragment was determined spectrophotometrically at 232 nm in 30 mM HCl using the extinction coefficient of 5500 $mol^{-1}$ $cm^{-1}$. The size of the oligosaccharides were confirmed using MALDI MS (vide infra).

This library of heparin and heparan sulfate fragments of uniform saccharide number is then used in the screening assays.

EXAMPLE 5

Screening Assays (1) BIAcore Assay

This technology uses the optical phenomenon of surface plasmon resonance to monitor physical interactions between molecules. Passing the protein solution over a sensor surface to which the ligand is coupled monitors the real-time binding of proteins to an immobilized ligand. Detection is achieved by measuring refractive index changes very close to the sensor surface. When the refractive index is altered, the angle at which plasmon resonance occurs changes and this change directly correlates with the amount of protein interacting with the surface. A BIAcore 2000 is conveniently used. It is very sensitive and its microfluidics ensures that only small amounts of material are required.

The HLGAGs are immobilized on the biosensor chip. Intact HLGAGs are biotinylated via amino groups, or reducing termini modified with ammonia by reductive amination, using sulfo-NHS-biotin. Biotinylated HLGAGs are immobilized on streptavidin-coupled sensor chips. Solutions containing proteins of interest are injected over the sensor chip surface, and the binding is measured in real time (Fernig, In: Proteoglycan protocols, Ed. R.V. Iozzo, Humana Press, Totowa, N.J., USA, 2001). The inventors have demonstrated that baculovirus and *E. coli* expressed human IL-4 (rhIL-4), baculovirus expressed human IL-5 (rhIL-5), Cos-7 cell expressed human PECAM-1 fusion proteins (flag-PECAM-1 and PECAM-Fc) and *E. coli* expressed Cyclophilin A (CypA) readily bind to heparin immobilized by this method (FIG. 2). In addition there is preliminary evidence that the IL-5 receptor chain, βc, binds to heparin. In all cases binding is specific, as there is little or no interaction with sensor chips lacking heparin with any of the targeted proteins, and binding is inhibited by exogenous heparin. Initial analyzes indicate that the binding of rhIL-5 to heparin has affinity constants of the order from $50-5\times10^{-9}$. Because unsubstituted amines are variably present in heparan sulfates from different tissues, an alternative method of biotin labeling is recommended for the heparan sulfate chip. In this case, heparan sulfate is labeled via oxidized cis-diol residues using biotinyl-LC-hydrazine.

(2) Filter Binding Assay

Figure 3:
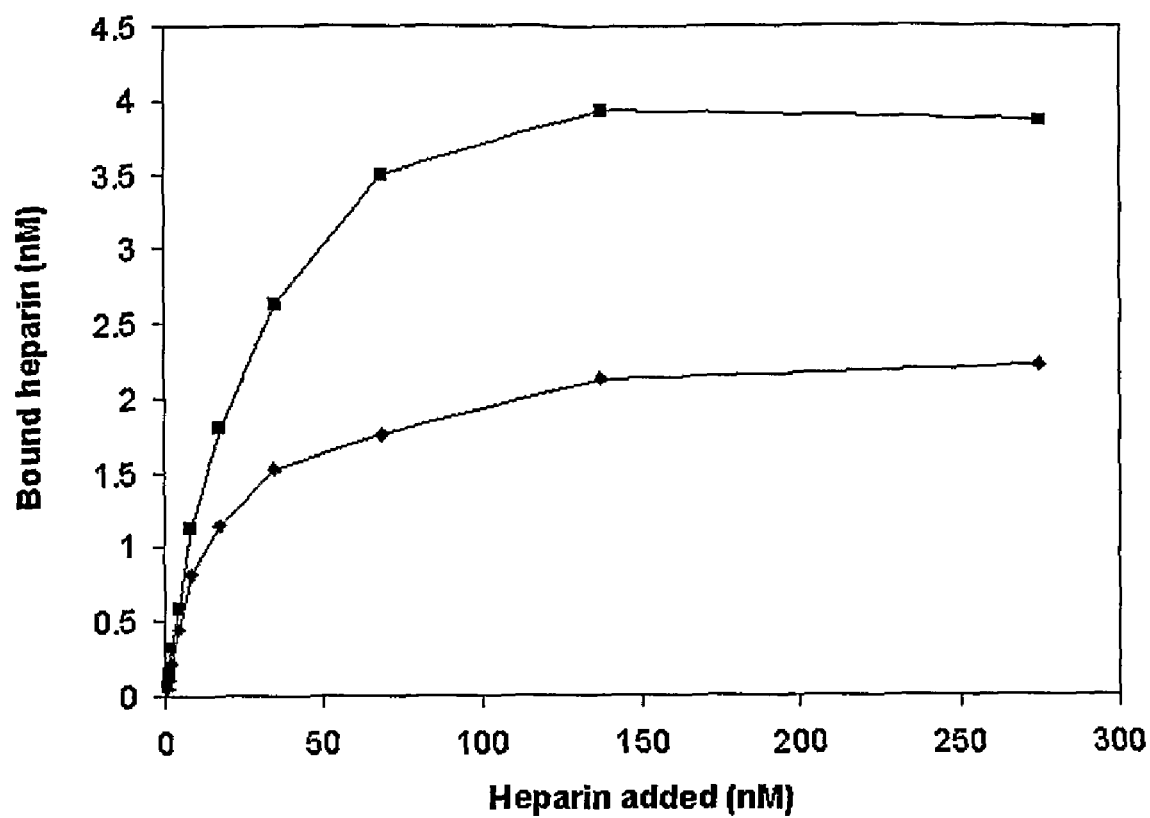

HLGAGs are labeled with a reporter molecule via carboxylate groups of uronic acids in the presence of EDC, via N-unsubstituted glucosmines, or via the reducing terminus. Labeled HLGAGs are mixed with the protein of interest and allowed to equilibrate in nitrocellulose 96 well filter plates. The mixtures are centrifuged at low speed to filter the mixture. The filter adsorbs the protein or the protein-GAG complex, but not GAG alone. The labeled GAG is re-dissolved in buffer containing 2 M NaCl, and the amount of reporter molecule retained in the wells is determined using an appropriate detection device. The amount of bound heparin in each sample is quantified using standard solutions of heparin-reporter. This method has been used to assess heparin binding of rhIL-4 (FIG. 3) and is used for other proteins of interest.

EXAMPLE 6

Screening of the Library

Figure 4A:
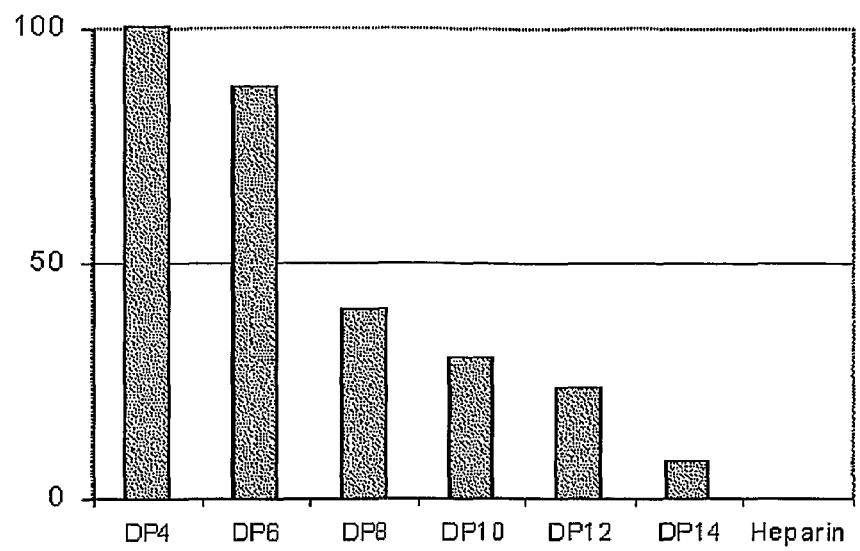
Figure 4B:
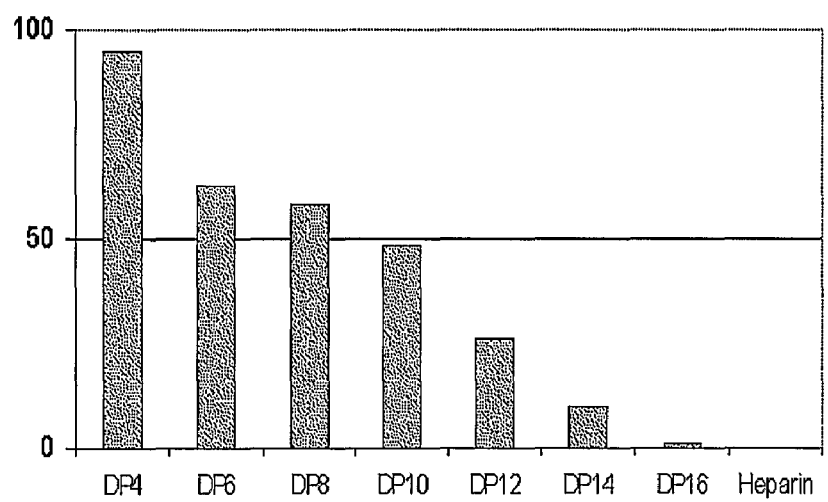

Preparations of heparin and heparan sulfate oligosaccharides of uniform saccharide number are tested for their ability to inhibit binding of the target proteins to heparin or heparan sulfate, respectively, using the BIAcore (FIG. 4).

Figure 5A:
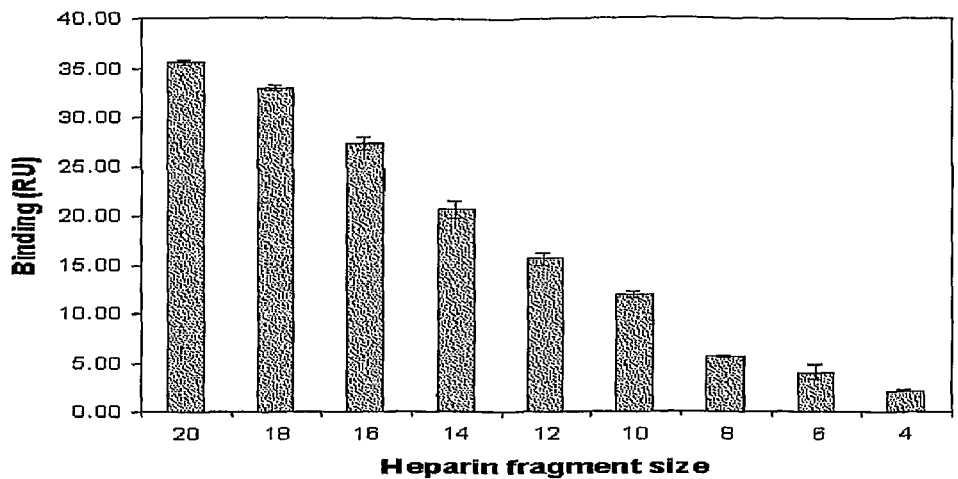
Figure 5B:
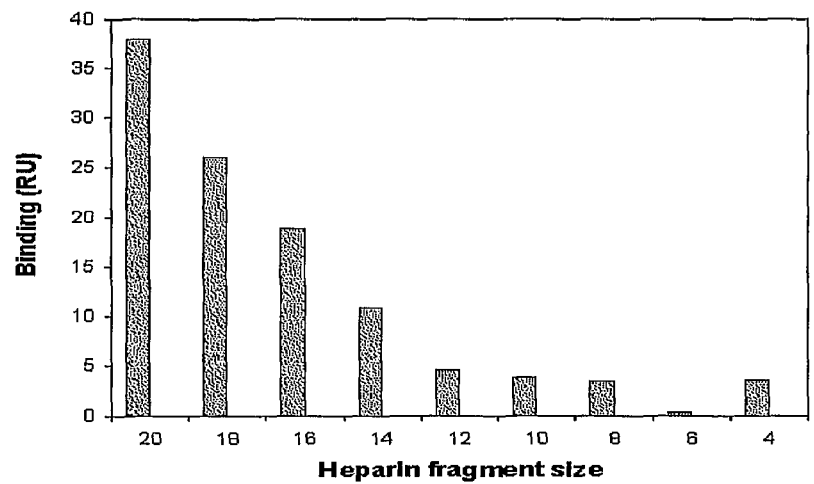
Figure 5C:
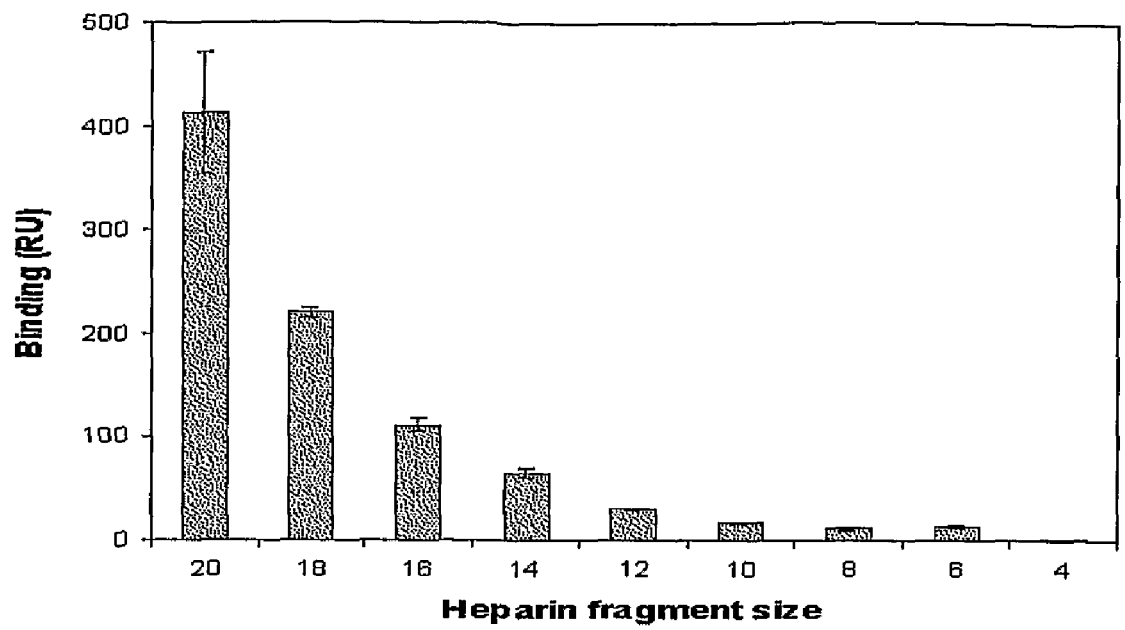

Following labeling with a reporter molecule, direct oligosaccharide binding may be assayed using the filter assay, FRET, or FP. Oligosaccharides may also be biotinylated by direct reductive amination, and immobilized on streptavidin sensor chips to assess protein binding (Delehedde, *J. Biol. Chem.* 277(14): 12456-12462, 2002). This method has been used to assess the minimal HLGAG length required for binding to rhIL-4, PECAM-1 and cypA (FIG. 5).

This initial screen indicates the smallest oligosaccharides that bind well to the target proteins. These oligosaccharides are separated on their pattern of sulfation by strong anion exchange (SAX) chromatography (mini-Q column and SMART System). The SMART HPLC system is ideal for this application as its microfluidics ensures very high resolution and very little increase in volume. The fractions produced again are screened for their ability to bind the target proteins. If fragments of the same saccharide number but differing in sulfation patterns have different activities, then it is concluded that the target proteins bind particular motifs in the heparin/heparan sulfate chain. These fractions are stored in 96-well arrays for testing in other screens.

EXAMPLE 7

Characterization of the Active Oligosaccharides

Enrichment of the active oligosaccharides for use in functional assays and for further structural analysis was achieved by affinity chromatography on a matrix coupled with the particular target protein. *E. coli*-expressed rhIL-4 was immobilized onto a HiTrap NHS-activated column by direct coupling through primary amines. Prior to coupling, amino acids involved in heparin binding were protected from reacting with the column by incubation with N-acetylated heparin. CypA is immobilized in a similar manner. rhIL-5 was immobilized onto AffiGel Hz support via periodate oxidized cisdiols on the carbohydrate portion of rhIL-5. PECAM-1 may be immobilized in either manner, or may be immobilized on a column carrying Anti-flag tag antibodies.

Oligosaccharides of size DP 10 were loaded onto the rhIL-4 column in phosphate-buffered saline (PBS). Oligosaccharide fragments bound to the column were washed with PBS, and eluted with 2 M NaCl. Oligosaccharides of size DP 12 were loaded onto the rhIL-5 column in hepes buffer containing 100 mM NaCl, 0.002% v/v Tween 20 and 50 µM $ZnSO_4$. Oligosaccharide fragments bound to the column were washed with the same buffer but containing 200 mM NaCl, and eluted with 1 M NaCl. Eluted oligosaccharides were pooled for further analysis. A similar methodology is employed to isolate oligosaccharide fragments that bind flag-PECAM-1 or Cyclophilin A.

The eluted fractions were, if necessary, diluted with water to reduce the salt concentration to less than 0.4 molar and analyzed directly by anion exchange chromatography. A Gilson (Middleton, Wis., USA) chromatograph comprised of two model 307 titanium pumps, a model 805 manometric module, a model 811 Titanium dynamic mixer, a model 215 autosampler/fraction collector and a model 151 UV detector. The chromatograph was under the control of Gilson Unipoint software. A 250×4.5 mm Dionex (Sunnyvale, Calif., USA) Propac PA1 column was used and maintained at 40° C. in an Eppendorf (Alltech Associates, Sydney, Australia) TC-40 column heater. The column was eluted at 1.0 mL/min with a binary gradient formed from two buffers. Buffer A was 10 mM $Na_2HPO_4$ adjusted to pH 7.0. Buffer B was 10 mM $Na_2PO_4$ plus 2 M NaCl adjusted to pH 7.0. The gradient was 10% initially for 3 minutes, increased linearly to 40% at 6 minutes, 70% at 75 minutes, 100% at 76 minutes, where it was maintained for 4 minutes. The column was equilibrated for 7 minutes between injections. The effluent was monitored at 232 nm. The chromatogram obtained for the DP10 fraction bound to the IL-4 affinity column is compared with the chromatogram for the total DP10 pool in FIG. 6. The chromatogram obtained for the DP12 fraction bound to the IL-5 affinity column is compared for the total DP12 pool in FIG. 7.

Subsequently, more of the oligosaccharides were prepared by preparative anion-exchange chromatography. After workup, the fractions were analyzed by matrix assisted laser desorption ionization mass spectrometry (MALDI MS) using the procedure described by Venkataraman et al. (*Science* 286 (5439): 537-542, 1999). The basic peptide $(RG)_{19}R$ was prepared as the trifluoroacetate salt by Auspep (Melbourne, Australia). Approximately 20 mg of AG-1 X2 anion exchange resin in the hydroxide form (Biorad, Sydney, Australia) was added to an ice-cold aliquot (100 µL) of 50 µM peptide. The resulting suspension was centrifuged briefly and maintained in an ice-bath. An aliquot of peptide (1 µL) was mixed with 10 mg/mL caffeic acid in 50% v/v acetonitrile (8 µL) and 5-100 µM sample (1 µL), 1 µL spotted onto a stainless steel sample plate and allowed to dry. MALDI MS spectra were acquired in the linear mode by using a PerSeptive Biosystems (Applied Biosystems, Melbourne, Australia) Voyager reflectron time-of-flight instrument fitted with a 337-nm nitrogen laser. Delayed extraction was used to increase resolution (22 kV, grid at 93%, guide wire at 0.15%, pulse delay 150 ns, low mass gate at 2000, 50 shots averaged). Mass calibration was achieved by external calibration with the peptide calibration mixture provided by the manufacturer. The mass of the oligosaccharide was deduced by subtracting the mass of the $(RG)_{19}R$ peptide observed for that sample.

The masses obtained for the fractions A-C of the chromatogram indicated the presence of oligosaccharides containing between 9-13, and possibly more sulfate groups. The spectrum of fraction A is shown in FIG. 8.

EXAMPLE 8

Functional Analyses of the Active oligosaccharide on the Allergic Rhinitis and Asthma Protein Target, IL-5

The inventors have shown that heparin and certain heparan sulfates inhibit the proliferation of an IL-5 responsive cell line. This occurs at very low doses and is not due to a toxic effect of the HLGAG because other, structurally different, heparan sulfate preparations enhance proliferation of the IL-5 responsive line at the same concentrations of HLGAG and IL-5. In addition, the GAG, chondroitin sulfate C used at the same concentration as heparin has no effect on cell proliferation (FIG. 9). These experiments are performed with the IL-5 responsive cells, TF-1.8 and a clone of Ba/F-IL-5 cells. The TF-1.8 cells are a subclone of the TF-1 cells that have been selected for growth in IL-4 or IL-5. TF-1 cells were originally established from a bone marrow sample from a male with severe pancytopenia. These cells are dependent on IL-3 or GM-CSF for long term growth and are responsive to a variety of cytokines including IL-4, but not IL-5. The Ba/F-IL-5 cells were derived from the Ba/F3 cell line.

The Ba/F3 cell line was transformed to be both IL-5 dependent and to express luciferase by co-transfection of the cells with pGL3 control vector (Promega, USA) and pEE6hcmv-IL-5Rα. The control vector, pGL3 expresses a modified luciferase under the direct control of the SV40 promoter and enhancer, but contains no selectable marker. To prepare pEE6hcmv-hIL-5Rα a full length human IL-5 receptor α chain (5R-α) was cloned by RT PCR from HL60 cells. The preparation of the Ba/F-IL-5 cells has been described by Coombe et al. (Coombe et al., *Journal of Immunological Methods* 215: 145-150, 1998).

The Ba/F-IL-5 cells may be further modified by co-transfection with pPGK-puromycin-luciferase, a vector containing luciferase under the control of the SV40 promotor with the selectable marker puromycin (Coombe et al., 1998, Supra).

After transfection, positive transfectants are selected in 3 µg/ml puromycin. The positive transfectants are then cloned to produce a line with good luciferase expression. The proliferation assays are carried out in 96-well microplates suitable for such assays (Falcon). The wells are flat bottomed, with white sides and a clear bottom. Cells are washed to remove any cytokine in the growth medium and then resuspended in RPMI/5% w/v FCS. The cells are counted with a Coulter Multisizer (Coulter Electronics, England) and routinely $1.6 \times 10^4$ cells are added to microplate wells that contain either no IL-5 (negative control) or various dilutions of IL-5. When the effect of HLGAGs, chondroitin sulfate C, or the heparin fractions of a particular length, or heparin fragments of a particular length and structure is to be measured, the wells also contain various concentrations of these molecules.

The cells proliferate for 48 hours at 37° C. in a humidified atmosphere, after which the luciferase activity is measured by the addition of 50 µl of luciferase substrate buffer (50 mM Tris-HCl, pH 7.8, 15 mM $MgSO_4$, 33.3 mM DTT, 0.1 mM EDTA, 0.5 mM Na-luciferin, 0.5 mM ATP, 0.25 mM lithium Co A and 0.5% v/v Triton X-100). Immediately after the addition of the luciferase buffer the plate is assayed for luciferase activity. Light emissions are detected on a Victor 1420 Multilabel counter (Wallac, Turku, Finland). An example of the type of data obtained is shown in FIG. 9.

Using these assays it have been demonstrated that the DP12 pool of heparin fragments inhibit IL-5 dependent Ba/F-IL-5 cell proliferation. Smaller heparin fragments, DP4 and DP6, have little or no ability to inhibit IL-5 dependent Ba/F-IL-5 cell proliferation. In addition, different structures within the DP12 pool exhibit different abilities to inhibit IL-5 dependent Ba/F-IL-5 cell proliferation (FIG. 10).

The ability of HLGAGs and of heparin fragments of various sizes to block the binding of fluorescent-labeled IL-5 to its receptor is also tested. Fractions of heparin fragments of a particular size that may or may not bind to IL-5 are tested for their ability to block the binding of fluorescent-labeled IL-5 to its receptor. The IL-5 responsive cells TF-1.8 and Ba/F-IL-5, are used for these experiments.

Because heparin and heparin fragments may not directly block IL-5 binding to its receptor, but rather may interfere with IL-5 receptor complex formation and signaling, the effect of heparin and heparin fragments on the ability of IL-5 to bind to its high affinity receptor (IL-5 receptor alpha chain (IL-5Rα)) will be examined. Briefly, IL-5Rα is immobilised on a BIAcore chip and the ability of IL-5 to bind is determined. IL-5 binding will be determined in the absence of any heparin or GAG oligosaccharides or GAG-composite molecules and in the presence of various concentrations of heparin, or GAG oligosaccharides and/or GAG-composite molecules.

To fully appreciate the effect of the oligosaccharides on IL-5 activity, primary cells responsive to IL-5 are examined. Human peripheral blood eosinophils are isolated from healthy donors by a CD16 negative selection protocol. A common way to assess eosinophil activation is by monitoring their adhesion to immobilized IgG. The number of eosinophils bound to immobilized IgG when IL-5 is presented with the selected oligosaccharides, or with heparin or heparan sulfate, compared to IL-5 alone, is determined by measuring myeloperoxidase activity. Eosinopils separated from peripheral blood do not survive more than four days in the absence of cytokine. The relative ability of IL-5, IL-5 plus the selected oligosaccharides or the intact HLGAG on eosinophil survival is assessed at a range of cytokine concentrations. Eosinophil survival is determined by flow cytometry following propidium iodide staining.

EXAMPLE 9

Functional Analyses of the Active Oligosaccharides on the Allergic Rhinitis and Asthma Target Protein, IL-4

The inventors have shown that heparin inhibits the proliferation of an IL-4 responsive cell line. This occurs at very low doses and is not due to a toxic effect of the HLGAG because other, structurally different GAGs, e.g. chondroitin sulfate C, at the same concentrations of IL-4 and GAG have no effect. These experiments utilize the TF-1.8 cells. TF-1.8 cells are a subclone of the TF-1 cells that have been selected for growth in IL-4 or IL-5. TF-1 cells were originally established from a bone marrow sample from a male with severe pancytopenia. These cells are dependent on IL-3 or GM-CSF for long term growth and are responsive to a variety of cytokines including IL-4, but not IL-5.

TF-1.8 cells have been transfected with the firefly luciferase gene contained in the expression vector, pPGK-puromycin-luciferase (Coombe et al., 1998, Supra). The positive transfectants are cloned to produce a line with good luciferase expression. The proliferation assays are carried out in 96-well microplates suitable for such assays Falcon). The wells are flat bottomed, with white sides and a clear bottom. Cells are washed to remove any cytokine in the growth medium and then resuspended in RPMI/5% w/v FCS. The cells are counted with a Coulter Multisizer (Coulter Electronics, England) and routinely $2.5 \times 10^4$ cells are added to microplate wells that contain either no IL-4 (negative control) or various dilutions of IL-4. When the effect of HLGAGs, chondroitin sulfate C, or the heparin fractions of a particular length, or heparin fragments of a particular length and structure is to be measured, the wells also contain various concentrations of these molecules.

The cells proliferate for 48 hours at 37° C. in a humidified atmosphere, after which the luciferase activity is measured by the addition of 50 µl of luciferase substrate buffer (50 mm Tris-HCl, pH 7.8, 15 mM $MgSO_4$, 33.3 mM DTT, 0.1 mM EDTA, 0.5 mM Na-luciferin, 0.5 mM ATP, 0.25 mM lithium Co A and 0.5% v/v Triton X-100). Immediately after the addition of the luciferase buffer the plate is assayed for luciferase activity. Light emissions are detected on a Victor 1420 Multilabel counter (Wallac, Turku, Finland). An example of the type of data obtained is shown in FIG. 11.

Using this assay, the inventors demonstrated that heparin fragments of size DP10 give good inhibitory activity, whereas small fragments, DP4 and DP6, display little or no ability to inhibit the IL-4 dependent proliferation of TF-1.8 cells. This assay is used to demonstrate that structurally different heparin fragments in the DP10 pool have different abilities to inhibit the IL-4 dependent proliferation of TF-1.8 cells.

The ability of fluorescent-labeled IL-4 to bind to its receptor, in the presence or absence of heparin, heparin fragments of a particular degree of polymerization, and heparin fragments of a particular degree of polymerization and structure, is examined. These experiments will be performed using different concentrations of IL-4 and the heparin or the heparin fragments. Comparisons with other GAGs shown not to have activity in inhibiting the 14 dependent proliferation of TF-1.8 cells, e.g. chondroitin sulfate C, will demonstrate broad specificity. Comparisons between structurally different heparin fragments of the same degree of polymerization, e.g. DP10, will demonstrate that the structure of the heparin fragment dictates whether or not a heparin fragment can inhibit the interaction of IL-4 with its receptor.

EXAMPLE 10

Effect of Different Size Heparin Fragments on IL-4 and IL-5 Dependent Cell Proliferation Table 1 demonstrates that different sized heparin fragments generated by heparinase I digestion differ in their ability to inhibit IL-5 and IL-4 dependent cell proliferation. Data are presented as the concentration of the various heparin fragments that is required to have equivalent activity to 0.4 µM undigested heparin.

TABLE 1

| Activity of heparinase I generated heparin fragments | |
|---|---|
| Size of heparin fragment | concentration of heparin fragments required to equal activity of 0.4 µM heparin |
| Activity Summary - IL-5: | |
| DP4 fragments | >50 µM |
| DP6 fragments | >50 µM |

TABLE 1-continued

Activity of heparinase I generated heparin fragments

| Size of heparin fragment | concentration of heparin fragments required to equal activity of 0.4 µM heparin |
|---|---|
| DP8 fragments | 10 µM |
| DP12 fragments | 2-4 µM |
| Activity Summary - IL-4: | |
| DP4 fragments | >50 µM |
| DP6 fragments | 8 µM |
| DP8 fragments | 4-8 µM |
| DP10 fragments | 4 µM |
| DP12 fragments | 0.3 µM |

EXAMPLE 11

Functional Analyses of the Active Oligosaccharides on the Melanoma Protein Target, PECAM-1

The inventors have shown that recombinant, human PECAM-1 expressed as a fusion protein (Flag-PECAM-1) binds very effectively to melanoma cell surfaces and this binding is mediated by melanoma cell surface heparan sulfate. The fusion protein consists of the extracellular domains of PECAM-1 fused to a Flag tag. The binding of Flag-PECAM-1 to melanoma cell surfaces is performed and quantified as follows. These experiments have been done using the A2058 melanoma cells. These cells were demonstrated to have significant quantities of heparan sulfate on their cell surfaces by quantification of the binding of the HepSS-1 monoclonal antibody. The HepSS-1 monoclonal antibody recognizes a sulfated epitope contained within heparan sulfate chain (Kure and Yoshie, *Journal of Immunology* 137: 3900-3908, 1986). To examine the binding of Flag-PECAM-1 A2058 cells are harvested using 2.5 mM EDTA in PBS, washed and resuspended in 10 mM Bistris (pH 6.3) containing 150 mM NaCl (Bistris buffer) and 0.5% w/v BSA. The number of cells used for each binding reaction was $1 \times 10^5$. These cells were pelleted in a polystyrene tube suitable for use on the flow cytometer and 60 µg Flag-PECAM-1 in the Bistris buffer was mixed with the cells and binding proceeds for 1 hour at room temperature. Excess Flag-PECAM-1 is then washed off using the Bistris buffer.

The bound Flag-PECAM-1 is detected using an anti-human PECAM-1 polyclonal antibody and a FITC conjugated anti-rabbit second antibody. The level of fluorescence was determined using a Coulter EPICS XL flow cytometer (Coulter Electronics, UK). For inhibition experiments 250 µg of a heparin solution or a chondroitin sulfate C solution was added to the Flag-PECAM-1 prior to adding to the cells. The binding of Flag-PECAM-1 to the A2058 cells could be titrated out and heparin was able to block binding, whereas chondroitin sulfite C was ineffective.

The ability of heparin to block Flag-PECAM-1 binding was dependent upon the concentration of heparin used. Treatment of the A2058 cells with 1 milli international Unit of heparanase III (Grampian Enzymes) for 30 min at 37° C. prior to assessing Flag-PECAM-1 binding was found to markedly decrease the amount of Flag-PECAM-1 that bound (FIG. 12). Similarly, treating the A2058 cells with chlorate, an inhibitor of sulfate adenylyltransferase and, hence, sulfation of heparan sulfate chains, markedly reduced the amount of Flag-PECAM-1 that bound to the cell surface. The inhibition of PECAM-1 binding to melanoma cells by heparin oligosaccharides is assessed using this assay.

The inhibition of melanoma cell binding to PECAM-1 is likely to affect both the passaging of melanoma cells across capillary endothelia (diapedesis) and the formation of protective platelet aggregates around melanoma cells in the circulation. Both endothelial cells and platelets express PECAM-1. Both diapedesis and platelet aggregation are critical for metastatic disease. A model of diapedesis utilizing human umbilical vein endothelial cell monolayers grown on the membrane of a transwell chamber has been developed. The melanoma cells are placed in the upper chamber on the endothelial monolayer and their migration into the lower chamber is quantified using the CyQuant assay kit (Molecular Probes) with fluorescence being read on a Victor 1420 Multilabel counter (Wallac, Turku, Finland). The interaction of melanoma cells with platelets is examined by placing melanoma cells on platelet monolayers prepared on extracellular matrix as described by others (Varon et al., *Blood* 91: 500-507, 1998) or on a 3-aminopropyltriethoxysilane coated surface (Rainger et al., *Thromb. Haemost.* 79: 1177-1183, 1998) and their adhesion and spreading examined microscopically. The interactions of melanoma cells with endothelial cell layers, the interactions of platelets with endothelial cell layers and the interactions of melanoma cells with platelets under flow conditions are examined. The flow conditions are designed to mimic that of blood flow. The ability of the oligosaccharides to interfere with melanoma cell migration in the diapedesis model and with the interaction of melanoma cells with platelets is assessed.

EXAMPLE 12

Functional Analyses of the Active Oligosaccharides on the Inflammation Protein Target, PECAM-1

The inventors prepared a fluorescent heparan sulfate complex that demonstrated binding to the surface of the monocytic cell line, U937. The fluorescent heparan sulfate complex and a fluorescent heparin complex is used to bind to the surface of peripheral blood leukocytes. These complexes are prepared by biotin-labeling the HLGAGs with sulfo-NHS-LC-biotin which reacts with bare amines located along the sugar chain. The biotin labeled HLGAGs are reacted with AlexaFluor 488 conjugated streptavidin at a ratio which will give on average 4 GAG chains per streptavidin molecule. The unincorporated AlexaFluor 488 conjugated streptavidin is separated from the HLGAG-streptavidin-AlexaFluor-488 complex (HLGAG complex) by a gel filtration step. The complex is then reacted with $2.5 \times 10^4$ cells for 1 hour at room temperature and, after fixing with 1% w/v paraformaldehyde the level of fluorescence is measured by flow cytometry.

Experiments with U937 cells have demonstrated that a heparan sulfate form of the complex binds to the cell surface and binding is blocked with free unlabeled heparan sulfate but not with chondroitin sulfate.

When monitoring the contribution of PECAM-1 expressed by leukocytes to the binding of the HLGAG complex the assay is performed in 10 mM Bistris (pH 6.3) containing 150 mM NaCl (Bistris buffer) and 0.5% w/v BSA. The ability of a polyclonal anti-PECAM-1 antibody to block binding is assessed. Similarly, the ability of heparin fragments of a uniform degree of polymerization, and structurally defined heparin figments of a uniform degree of polymerization to block complex binding will be assessed.

PECAM-1 has been demonstrated to be involved in the migration of leukocytes across an endothelium in response to an inflammatory stimulus (Muller and Randolph, *Journal of Leukocyte Biology* 66: 698-704, 1999). PECAM-PECAM interactions are believed to be involved in this migration. In addition, PECAM-1 has been shown to be involved in leukocyte migration through the basal lamina that underlies endothelial cells. The PECAM-1 ligand involved has not been defined. The inventors propose heparan sulfate in the basal lamina is involved in this PECAM-1-dependent migration. Moreover, the binding of exogenous heparin or heparin fragments to PECAM-1 on either the endothelial cells or the leukocytes may interfere with PECAM-PECAM interactions.

Leukocyte migration across an endothelial cell layer is examined using the transwell assay. Human umbilical vein endothelial cells are grown in the top surface of a transwell and the migration of leukocytes across this cell layer into the bottom chamber is quantified using the CyQuant assay kit (Molecular Probes) with fluorescence being read on a Victor 1420 Multilabel counter (Wallac). The endothelial cells may be stimulated with inflammatory cytokines such as TNFα and IL-1β and chemotactic factors like N-formyl-methionylleucylphenylalanine (FMLP), RANTES (regulated on activation, normal T cell expressed and secreted), IL-8 and others may be added to the bottom chamber to direct leukocyte migration. The ability of heparin and heparin fragments to inhibit leukocyte migration across an endothelial cell layer will be assessed. The ability of heparin and heparin fragments to block leukocyte migration across a basal lamina is also assessed.

In these experiments, the endothelial cells may be grown on a collagen gel and the levels of leukocyte migration into the gel determined, or the endothelial cells may be stripped from the collagen gel exposing the underlying basal lamina and leukocyte migration examined. A transwell assay may also be used, in which endothelial cells are grown on the upper surface of the transwell and then removed allowing leukocyte migration directly through the basal lamina to be monitored.

EXAMPLE 13

Specialized Reagents (1) Oligosaccharide Standards

These standards are used to determine the number of saccharide units within each oligosaccharide fragment. They are produced from lung heparan (almost homogeneously IdoA2S-GlcN6S). This heparin is cleaved by $HNO_2$, pH 3, borohydride reduced and separated into DP 2 to ~18 oligosaccharides.

(2) IL-5 and IL-4

Recombinant human IL-4 and IL-5 are prepared using a baculovirus expression system. Recombinant human IL-4 is also expressed in an *E. coli* expression system. Recombinant human IL-4 or IL-5 carrying site directed mutations are expressed using a baculovirus expression system. The resulting proteins are then purified by affinity chromatography on HiTrap activated NHS columns derivatized with hydrazine and coupled with either the monoclonal antibody H30 which recognizes IL-5, or the monoclonal antibody, 11B4, which recognizes IL-4.

(3) PECAM-1

The PECAM-1 fusion protein, flag-PECAM-1, consisting of the extracellular domain of PECAM-1 fused to the flag affinity tag, is produced by transient transfection of Cos-7 cells and purified by affinity chromatography on columns of anti-flag tag coupled to Sepharose. In addition, the inventors used expression vectors carrying truncated forms of the Flag-PECAM-1 fusion protein that allow the binding analysis of individual Ig-like domains of PECAM-1.

(4) Cyclophilin A

Cyclophilin A has been cloned by RT-PCR from cells, and the DNA ligated into an *E. coli* expression vector. CypA is expressed into inclusion bodies, solubilized with 6M urea, and refolded by extensive dialysis against dilute buffer. Refolded CypA is purified from other bacterial proteins by a combination of ammonium sulfate fractional precipitation, anion exchange chromatography and size exclusion chromatography.

(5) IL-3, IL-5 and GM-CSF Common Receptor β (βc)

The IL-3, IL-5 and GM-CSF common receptor β (βc), consisting of the extracellular domain of the receptor fused to the flag affinity tag, is produced by transient transfection of Cos-7 cells and purified by affinity chromatography on columns of anti-flag tag coupled to Sepharose.

EXAMPLE 14

ELISA

The Principle

Heparin or heparin fragments coupled to the wells of a 96-well plastic assay plate are used to selectively immobilize cytokines or other heparin-binding proteins. The identity of the immobilized proteins is determined from the binding of an antibody specific to the cytokine or protein of interest. The methodology is developed for coupling intact heparin onto the plate, but later heparin or heparan fragments.

A number of different methods are examined to determine the best way to couple heparin onto the plate without (a) reducing the protein binding activity of the heparin, or (b) interfering with the detection of the protein-specific antibody. Exemplary methods for coupling GAG and GAG-like molecules such as heparin to a solid substrate are set out in International Patent Publication WO 03/01476, particularly see Examples 4, 5, and 6. This document is herein incorporated by reference. Further examples of methods for coupling heparin to a solid substrate include:—

(1) Heparin is complexed with tridodecylmethylammonium (TDMAC) and this complex is then adsorbed to the plate. The hydrocarbon chains of TDMAC form a strong hydrophobic association with the plate leaving the ammonium moiety to form ionic bonds with the heparin.

(2) Heparin is immobilized via its reducing terminus to microtiter plates coated with methyl vinyl ether-maleic anhydride copolymer (MMAC). The introduction of hydrazino groups of MMAC coated plates using adipic acid dihydrazide provides a means of stably coupling heparin to the plate. Reductive amination is used to react the hydrazino groups with formyl groups on the saccharide.

(3) Heparin is immobilized through ionic complexation using a polymerizable cationic lipid, diallyl(dioleyl)ammonium bromide (DADOA). DADOA is composed of a long chain hydrophobic part and a hydrophilic head with double bonds that render it polymerizable. Heparin forms an ionic complex with DADOA and the complex is retained on the plastic surface via hydrophobic association.

EXAMPLE 15

Orally Active Heparin

Generally heparin has not been administered orally because of difficulties in adsorption from the gastrointestinal tract. However, recent data [Money and York, *Cardiovascular Surgery* 9: 211-218, 2001) have indicated that the addition of the organic chemical N-(8-(2-hydroxybenzoyl)amino)caprylate (SNAC) to heparin markedly enhances its adsorption. NMR data suggest that heparin interacts rather non-specifically with the delivery agent at points near OH groups on the heparin chain. The oral delivery of heparin will greatly expand the usefulness of this drug, particularly so for long term therapy.

EXAMPLE 16

Synthetic Heparin Mimetics/Analogs

Synthetic heparin mimetics/analogs have been successfully produced. Slight changes in the chemical structure of the molecules have altered which proteins bind to the heparin analog. This finding confirms the inventors' idea that by adjusting the chemical structure of the heparin analog, it is possible to selectively bind particular proteins. Moreover, the activity of the synthetic heparin analog significantly exceeds that of native heparin, again confirming the inventors' idea that by choosing the correct structure, it is possible to achieve the same or better activities as native heparin with reduced side-effects. The development of GAG-composite structures was performed to facilitate binding to the GAG-binding site on the ligand. Yet these composite structures have less side-effects than native heparin, binding to platelet factor IV for example is reduced compared to native heparin.

EXAMPLE 17

IL-4

Figure 14:
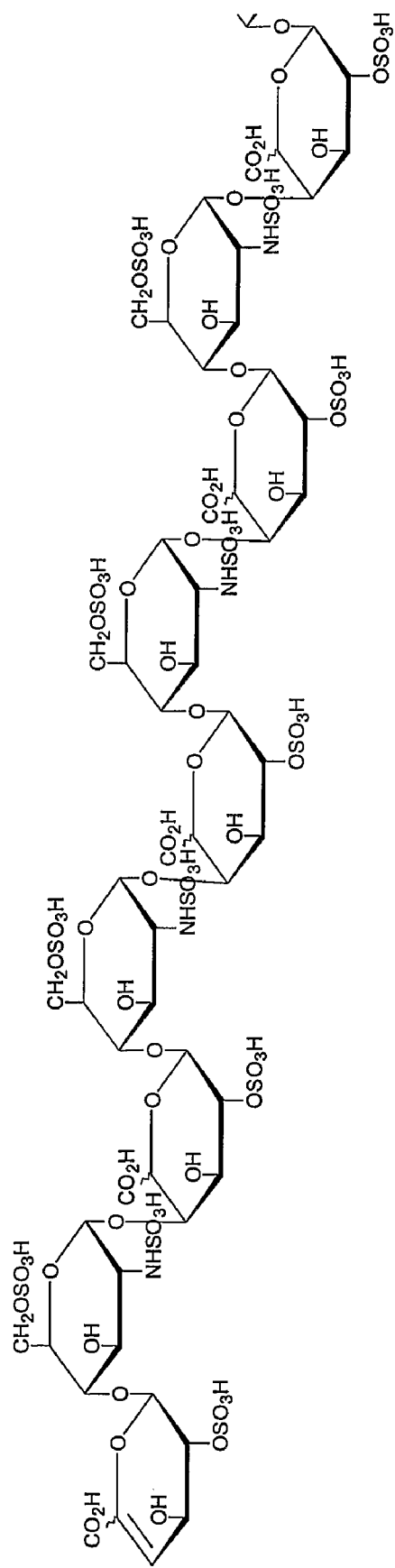
Figure 15:
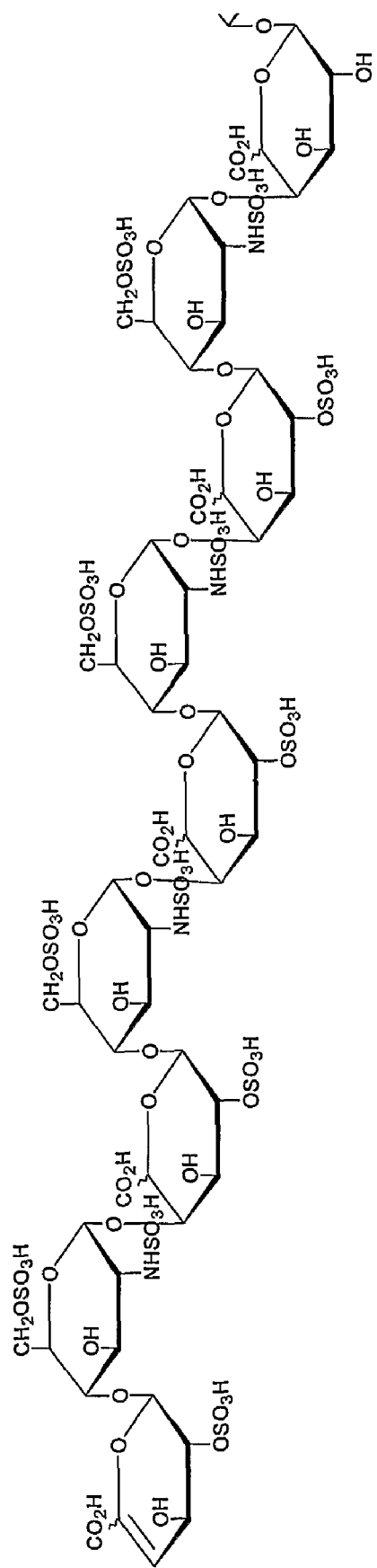

Fragments of size DP 10 were screened for binding ability to IL-4. Since the fragments were produced by heparinase I digestion, they contained an unsaturation at the non-reducing terminus. Moreover, some of the structures derived were particularly highly sulfated. The fragments showed a graduation in activity and there may be elements (i.e. sulfates) in the targets that are not strictly necessary for binding. Three targets were used, i.e.:—
Target 1:
This structure (fragment 10.8.1.5) comprises five repeating units of the trisulfated disaccharide, i.e. ΔUA2SGlcNS6S-(UA2SGlcNS6S)$_4$. It is represented schematically in FIG. 14.
Target 2:
This structure (fragment 10.7.2.4) comprises four repeating units of the trisulfated disaccharide with a disulfated disaccharide at the reducing terminus, i.e. ΔUA2SGlcNS6S-(UA2SGlcNS6S)$_3$-UAGlcNS6S. It is represented schematically in FIG. 15.
Target 3:
This fragment (10.9.1.2) includes one of the following four possible structures containing 8 O-sulfates and 4 N-sulfates:—
(1)　ΔUA2SGlcNS6S-UAGlcNAc6S-UA2SGlcNS6S-UA2SGlcNS-UA2SGlcNS6S;
(2)　ΔUA2SGlcNS6S-UAGlcNAc6S-UA2SGlcNS6S-UA2SGlcNS6S-UA2SGlcNS;
(3)　ΔUA2SGlcNS6S-UA2SGlcNS-UA2SGlcNS6S-UAGlcNAc6S-UA2SGlcNS6S;
(4)　ΔUA2SGlcNS6S-UA2SGlcNS6S-UA2SGlcNS6S-UAGlcNAc6S-UA2SGlcNS6S.

With regard to Targets 1-3, above, "UA2S" refers to 2-O-sulfated-uronic acid, "GlcNS6S" refers to 6-O-sulfated-N-sulfated glucosamine and "GlcNAc6S" refers to 6-O-sulfated-N-acetylated glucosamine. Δ means "unsaturated" thus ΔUA means an unsaturated uronic acid and in this case is the result of enzymatic cleavage.

EXAMPLE 18

IL-5

Figure 16:
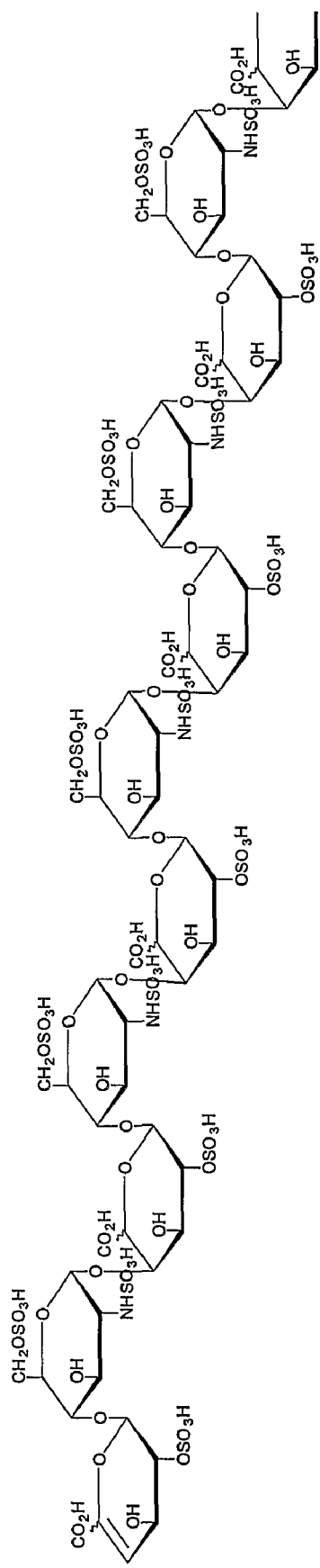
Figure 17:
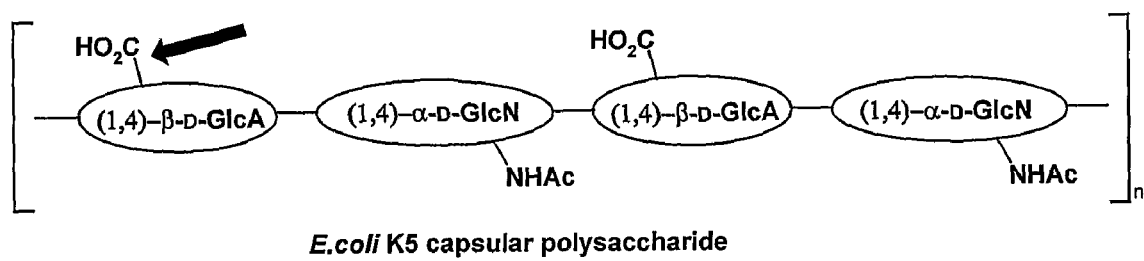
Figure 17:
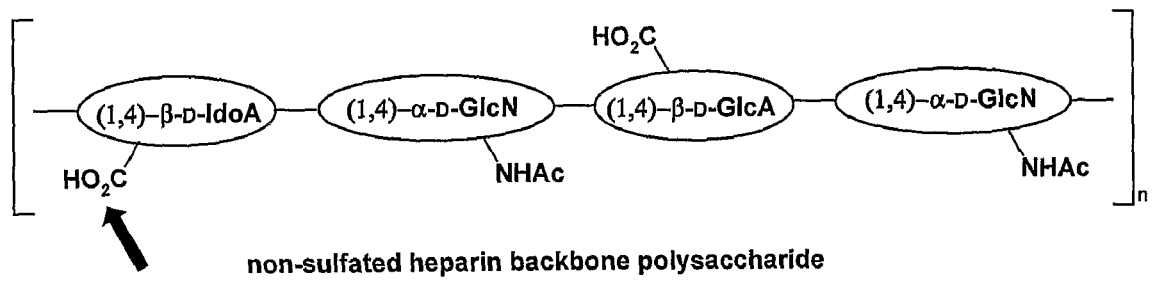
Figure 18:
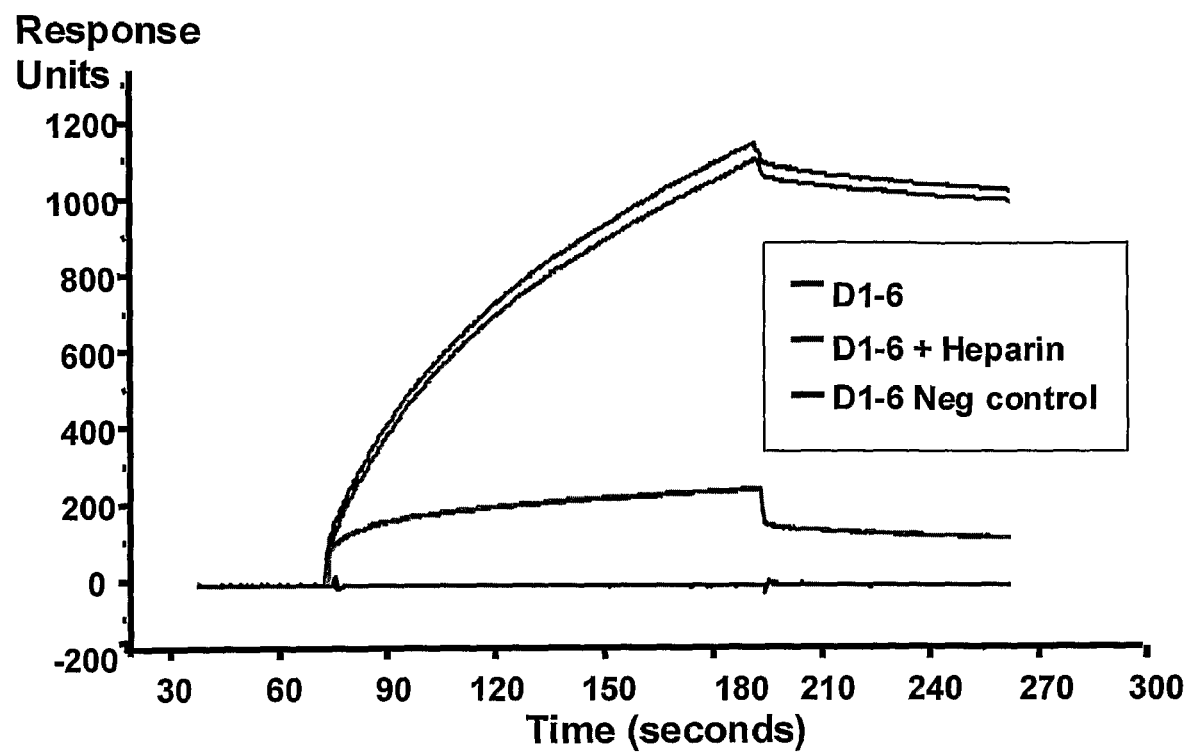
Figure 19:
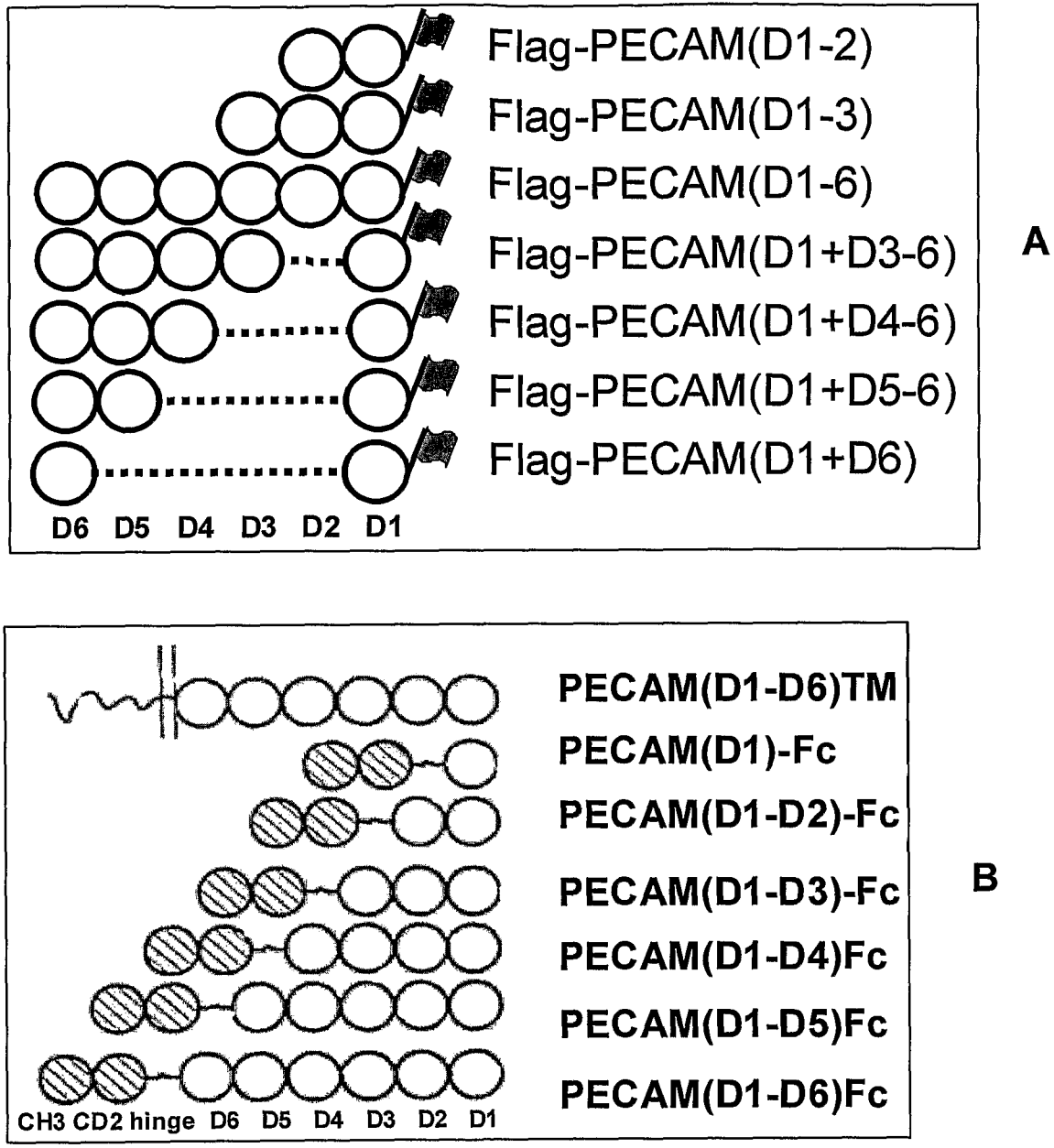
Figure 20:
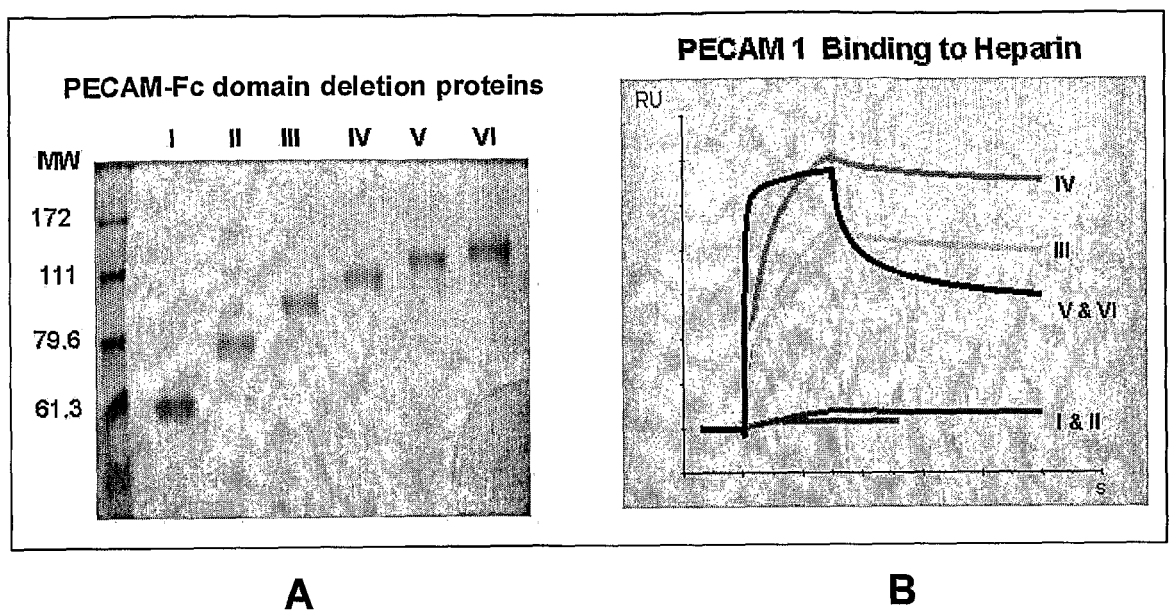
Figure 21:
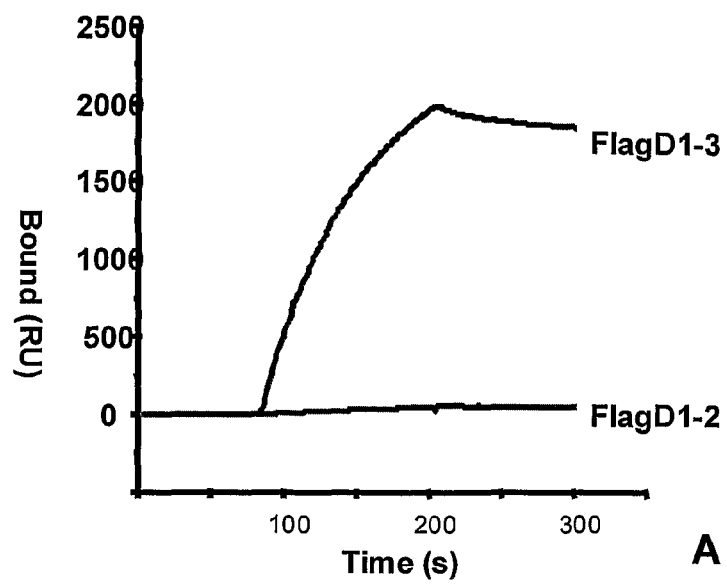
Figure 21:
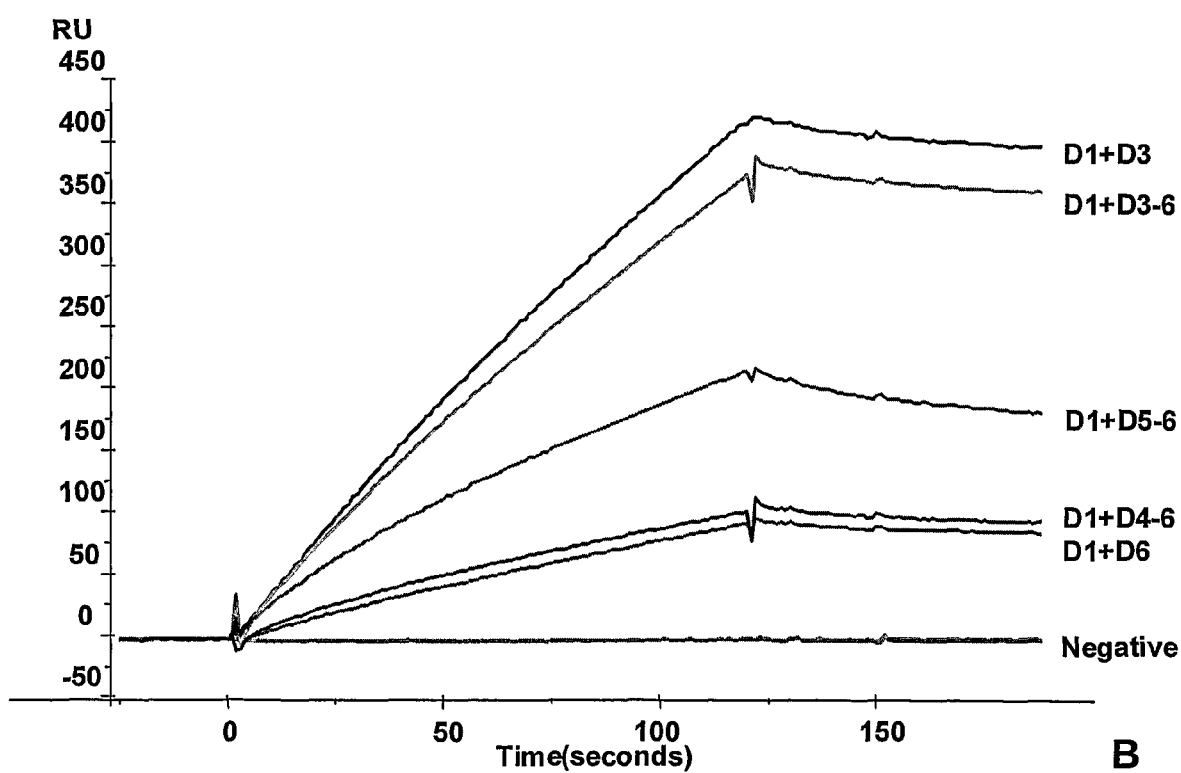
Figure 22:
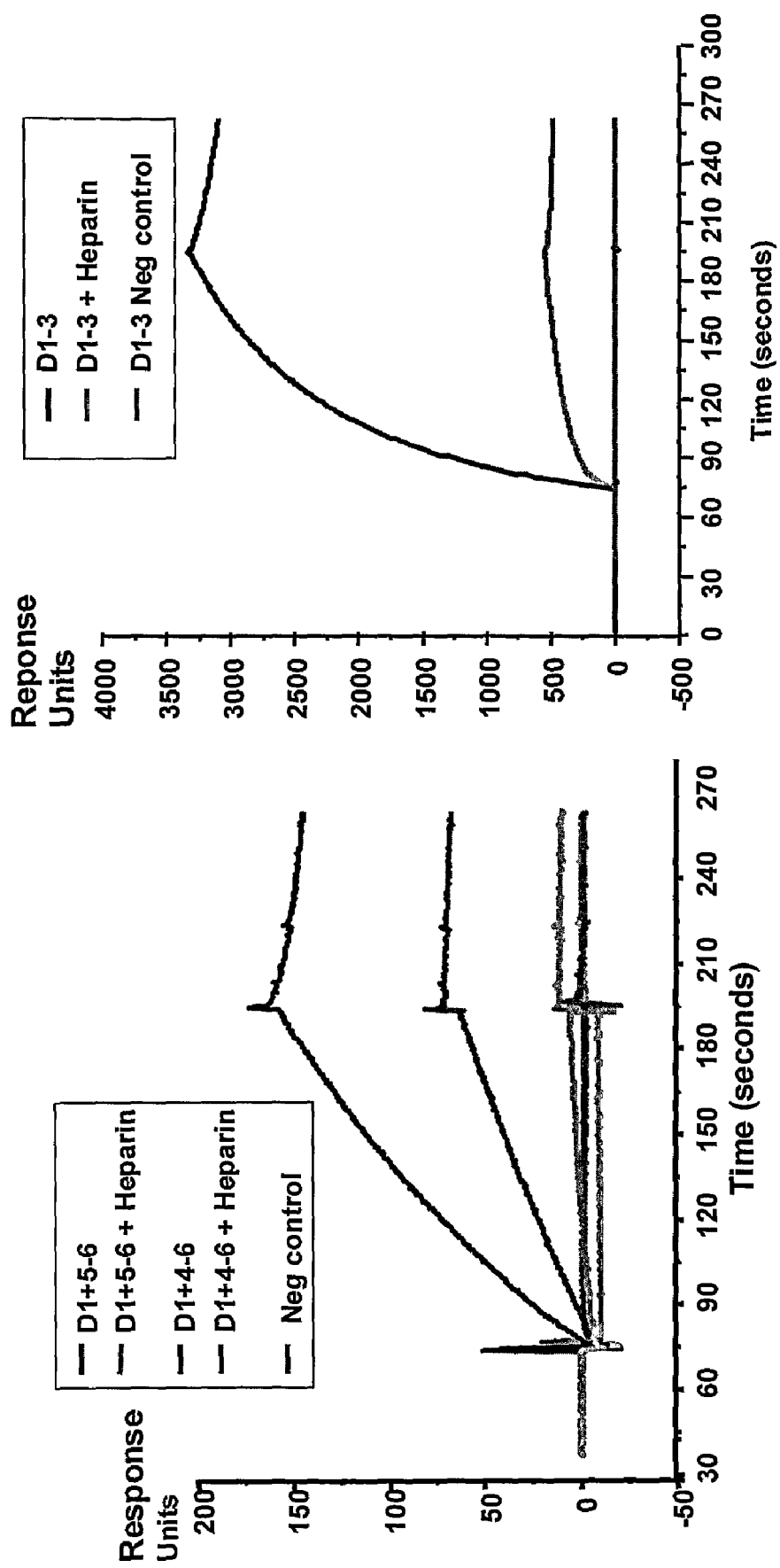

The focus for fragment that bind to IL-5 was upon fragments of size DP 12. The fragments contained an unsaturation at the non-reducing terminus. The following structures have been found in the penultimate pools. The rank of activity is 12.8.3>12.9.1~12.9.2>12.9.4~12.9.3>12.8.1~12.10.2>12.2.3.
Target 1:
The major component of fraction 12.8.3 is 12.8.3.5+6, which is a sequence of repeating trisulfated disaccharides, i.e. ΔUA2SGlcNS6S-(UA2SGlcNS6S)$_5$, wherein "UA2S" refers to 2-O-sulfated-uronic acid, "GlcNS6S" refers to 6-O-sulfated-N-sulfated glucosamine and "GlcNAc6S" refers to 6-O-sulfated-N-acetylated glucosamine. Δ means "unsaturated" thus ΔUA means an unsaturated uronic acid and in this case this is the result of enzymatic cleavage. This structure is represented schematically in FIG. 16.

In the main, the remaining sequences are less sulfated than Target 1, although the major component in each case is the trisulfated disaccharide (≧50%). A common motif within these sequences is the DP6 sub-sequence UA2SGlcNS6S-UA2SGlcNAc6S-UA2SGlcNS6S.

EXAMPLE 19

Structure produced by 3-O-sulfotransferase-3 is highly active for IL-5 binding

Heparan sulfate 3-O-sulfotransferases add a sulfate to the 3-O position of glucosamine residues in heparan sulfate. The 3-O-sulfation of heparan sulfate is a rare modification in nature and constitutes the final step of the biosynthetic pathway for heparan sulfate. Heparan sulfate biosynthetic enzymes, including the 3-O-sulfotransferases, are present in a number of different isoforms and each isoform has slightly different substrate specificities and recognises different monosaccharides sequences. The isoform, designated 3-O-sulfotransferase-3 (3-OST-3) transfers a sulfate to the 3-O position of N-unsubstituted glucosamine in the tetrasaccharides, UA2S-GlcNS-IdoA2S-GlcNH$_2$6S or UA2S-GlcNS-IdoA2S-GlcNH$_2$ (Liu et al., *J. Biol. Chem.* 274: 38155-38162, 1999). A crystal structure of a ternary complex of human 3-OST-3 with 3'-phosphoadenosine 5'-phosphate (PAP) and the tetrasaccharide ΔUA2S-GlcNS6S-IdoA2S-GlcNS6S was identified. The central GlcNS6S of this tetrasaccharide is modified as a result of 3-OST-3 activity to become 3-0 sulfated (Moon et al., *J. Biol. Chem.* 279: 45185-45193, 2002), indicating that GlcNS units in an oligosaccharide can also be substituted by 3-OST-3. A glucosamine flanked on either side by IdoA2S in a skew-boat configuration seems critical for 3-OST-3 recognition.

Heparan sulfate modified by 3-OST-3 was extremely effective at inhibiting the binding of IL-5 to heparin and heparan sulfate immobilised on a biosensor chip. DP12 fragments obtained by heparinase III cleavage of heparan sulfate and modified with this enzyme were similarly active (FIGS. 27 and 28). These Figures show sensorgrams obtained using a BIAcore 2000 when IL-5 (in HEPES buffered saline containing 20 μM Zn SO$_4$) in the presence or absence of 3-OST-3 modified heparan sulfate or 3-OST-3 modified DP12 fragments are passed over immobilised heparin. These data indicate that an oligosaccharide containing the structure produced as a result of 3-OST-3 activity binds IL-5 far more readily than heparan sulfate that does not contain this modification, thereby very effectively inhibiting IL-5 binding to heparin. The heparan sulfate and the DP 12 heparan sulfate oligosaccharides were modified with 3-OST-3 according to the published method (Liu et al., 1999 Supra). Briefly, a reaction mixture consisting of heparan sulfate (or heparan sulfate oligosaccharide), [$^{35}$S]PAPS, 50 mM MES pH 7.0, 2 mM $MnCl_2$ 1 mM $MgCl_2$, bovine serum albumin and 1% v/v Triton X-100 (v/v) was incubated at 37° for 1.5 hours. The reaction was halted by adding twice the resulting volume of stopping buffer (50 mM sodium acetate pH 5.0, 150 mM NaCl, 0.1% v/v Triton X-100, 6M urea and 1 mM EDTA). The [$^{35}$S]heparan sulfate or [$^{35}$S]heparan sulfate oligosaccharide being isolated by DEAE chromatography with elution using 1M NaCl. The eluted material was dialysed against 20 mM ammonium bicarbonate and freeze dried.

EXAMPLE 20

Determination of Heparin Binding Sites on IL-5

Proteins expressed as truncated forms, or carrying point mutations, are used to determine amino acids that are important for interaction with heparin. The altered proteins are purified as described and screened in HLGAG binding assays as described. Proteins carrying amino acid changes that affect the level of heparin binding are compiled, and mapped on three-dimensional protein models. Using this methodology, several amino acids on rhIL-5 have been shown to be important for HLGAG binding. Namely, mutation of histidine 38, lysine 39, histidine 41, lysine 84 or lysine 85 all reduce the rhIL-5 binding by over 50% when 1 μM solutions are injected over heparin surfaces. These amino acids all map with close proximity to each other on the IL-5 surface. However, it is likely that histidine 38 and histidine 41 are components of a zinc binding site on IL-5. Zinc is required for heparin to bind to IL-5, therefore loss of a zinc binding capability reduces the heparin binding capability. These amino acids contribute in an indirect way to heparin binding to IL-5, whereas the amino acids lysine 84 and lysine 85 are key components of the heparin binding site and interact directly with the GAG chain. Other amino acids that contribute to the GAG binding site on IL-5 include K77, K70, R67, R90 and R91. These amino acids are on the exposed surface of the C-helix and adjacent β-pleated sheet composed of the C-D loop of one IL-5 monomer and the A-B loop of the other monomer (Milburn et al., *Nature* 363: 172-176, 1993). Because IL-5 is a homodimeric protein, there are two identical regions on the protein that can potentially interact with HLGAGs FIG. 13).

The charged residues, E88, E89, R90, R91 and R92, in the CD loop have been shown to be involved in the binding of the IL-5 receptor alpha chain (IL-5Rα) (Tavernier et al., *Proc Nail Acad Sci USA* 92: 5194-8, 1995; Wu et al., *J Biol Chem* 274: 20479-88, 1999). Interestingly, it appears that R90 is the critical residue for IL-5Rα binding, and it was suggested that the other charged amino acids were acting to provide an electrostatic balance of one net positive charge (Wu et al., *J Biol Chem* 274: 20479-88, 1999). The ability of heparin to impede IL-5 binding to its receptor will be determined using the assay described in Example 8. The fact that heparin inhibits IL-5 dependent cell proliferation (FIG. 9) supports the conclusion that the heparin binding site on IL-5 overlaps with the binding site for IL-5Rα. The heterodimeric IL-5 receptor consists of IL-5Rα and βc (β chain common to receptors of IL-3, IL-5 and GM-CSF). The receptor is not preformed on the cell surface, rather IL-5 binds IL-5Rα and this complex interacts with βc (Scibek et al., *Anal Biochem* 307: 258-65, 2002). Thus, interfering with IL-5 binding to IL-5Rα also interferes with the formation of functional IL-5 receptors, and with receptor signaling.

EXAMPLE 21

Determination of Heparin Binding Sites on PECAM-1

PECAM-1 expressed in truncated form has been used to localize the heparin binding domains.

FIG. 18 shows the BIAcore profile of the extracellular domains of PECAM-1 binding to heparin immobilised on the BIOsensor chip. The negative control is PECAM-1 binding to a dextran chip (no immobilised heparin). The addition of 2.5 μM of heparin markedly blocks binding. In these experiments 1 μM of purified PECAM-1 was used. The extracellular domains (1-6) of PECAM-1 were expressed in a FLAG expression system where a Flag-tag is attached to the amino terminus of the protein and the protein was truncated at the end of domain 6.

In order to determine the GAG-binding regions of PECAM-1, various constructs of PECAM-1 using both the Flag expression system and a fusion protein expression system were prepared (see FIG. 19). In the fusion protein expression the extracellular domains of PECAM1 were fused with the Fc region of human IgG1 (i.e. CH3 and CD2 domains and the hinge region). Various extracellular domains have been selectively deleted and the indicated constructs expressed and purified.

Binding experiments with these proteins has indicated to which PECAM-1 domains heparin binds. Two binding assays were used: the assay where PECAM-1 is reacted with a BIAcore biosensor chip to which heparin has been immobilised and the second assay is the binding of PECAM-1 to heparan sulfate on the cell surface.

BIAcore Analysis of the Fusion Proteins

FIG. 20 shows the binding of PECAM-FC fusion proteins to heparin immobilised on a biosensor chip. The purity of the proteins is indicated in the silver gel. These data indicate that there is a heparin binding region in domain 3 as D1-Fc, D1-2-Fc do not bind but D1-3-Fc does bind. The difference in the kinetics of binding of the longer constructs suggests that there may be a secondary heparin binding region in domains 5-6.

BIAcore Analysis of the Flag Expression System Proteins

The various Flag-PECAM-1 domain constructs were bound to heparin immobilised on a BIAcore chip. The results of the BIAcore analyses are shown in FIG. 21. As shown in Panel A of FIG. 21, although different Heparin-chips were used it is clear that Flag-D1-3 binds the chip very well whereas Flag-F1-2 does not bind. Comparing the Response Unit (RU) score shown for D1-D3 in Panel A and the data in Panel B of FIG. 21 suggests that although domain 3 binds in its own right, better binding occurs when domain 2 is present. Specifically, Flag D1-D3 shown in Panel A has an RU score of ~2000, whereas D1+D3 shown in Panel B has an RU score of ~425. There is also evidence for a weaker binding region that involves domains 5 & 6.

The effect of exogenously added heparin to the binding of PECAM-1 to the heparin biosensor chip was investigated. As shown in FIG. 22, binding of the Flag-constructs, D1+5-6; D1+4-6 and D1-D3, to the heparin biosensor chip is virtually totally inhibited by the addition of 2.5 μM heparin.

These experiments have shown that there appears to be two heparin binding regions on PECAM-1. One binding region requires PECAM-1 Ig-like domain 3 whereas the other region is located in the membrane proximal domains, most probably in PECAM-1 Ig-like domains 5 and/or 6.

Binding of PECAM-1 Proteins to a Cell Surface

PECAM-1 extracellular domains (1-6) expressed in the Flag-expression system bind to the surface of A2058 melanoma cells. A2058 melanoma cells express significant levels of heparan sulfate as demonstrated by the HepSS-1 antibody. PECAM-1 binding was detected by an anti-PECAM-1 polyclonal antibody and a FITC-labeled second antibody and quantified by flow cytometry.

The data presented in FIG. 12 suggests that PECAM-1 binding to these cells is via cell surface heparan sulfate because binding is diminished by treating the cells with heparinase III prior to adding the PECAM-1 (Panel B). Chlorate treatment of the cells also abolishes PECAM-1 binding (Panel A). Chlorate is an inhibitor of ATP sulfurylase and subsequently, the production of PAPS, the active donor for sulfotransferases. Thus cells treated with chlorate do not have correctly sulfated heparan sulfate on their surfaces. This indicates that PECAM-1 is recognising the sulfates displayed by heparan sulfate expressed on cell surfaces.

Figure 23:
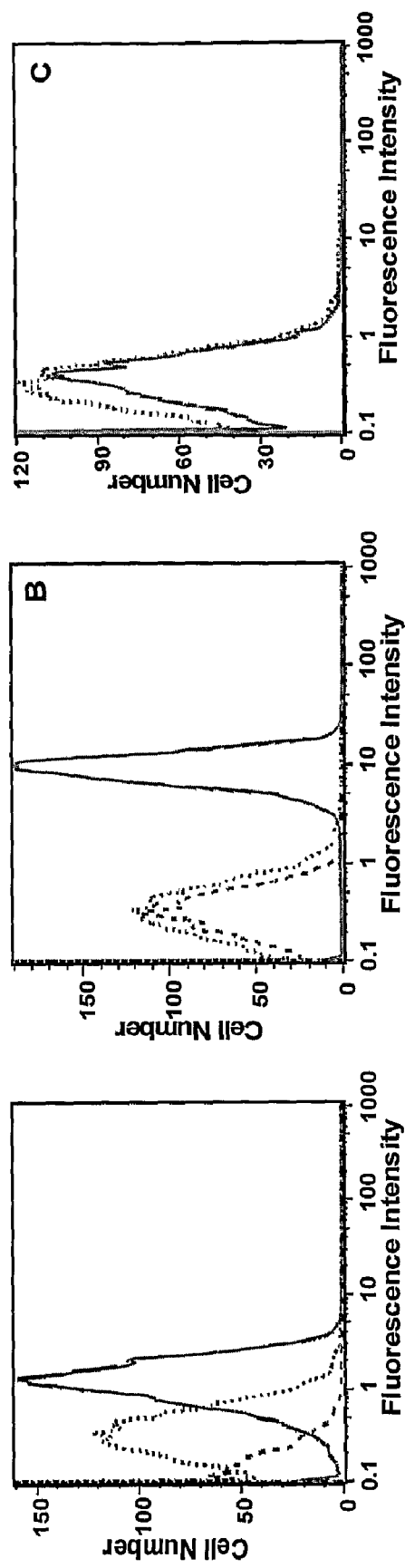

FIG. 23 shows Flag-PECAM-1 extracellular domains binding to A2058 cells. The data shown in FIG. 24 demonstrate that D1-D6 and D1-D3 can bind to the heparin chip and D1-D2 do not bind. Further, it is demonstrated that exogenous heparin can inhibit binding of both the D1-D6 and D1-D3 proteins. These data further support the view that a key domain of PECAM-1 for heparin binding is domain 3.

EXAMPLE 22

Determination of Heparin Binding Sites on IL-4

Figure 24:
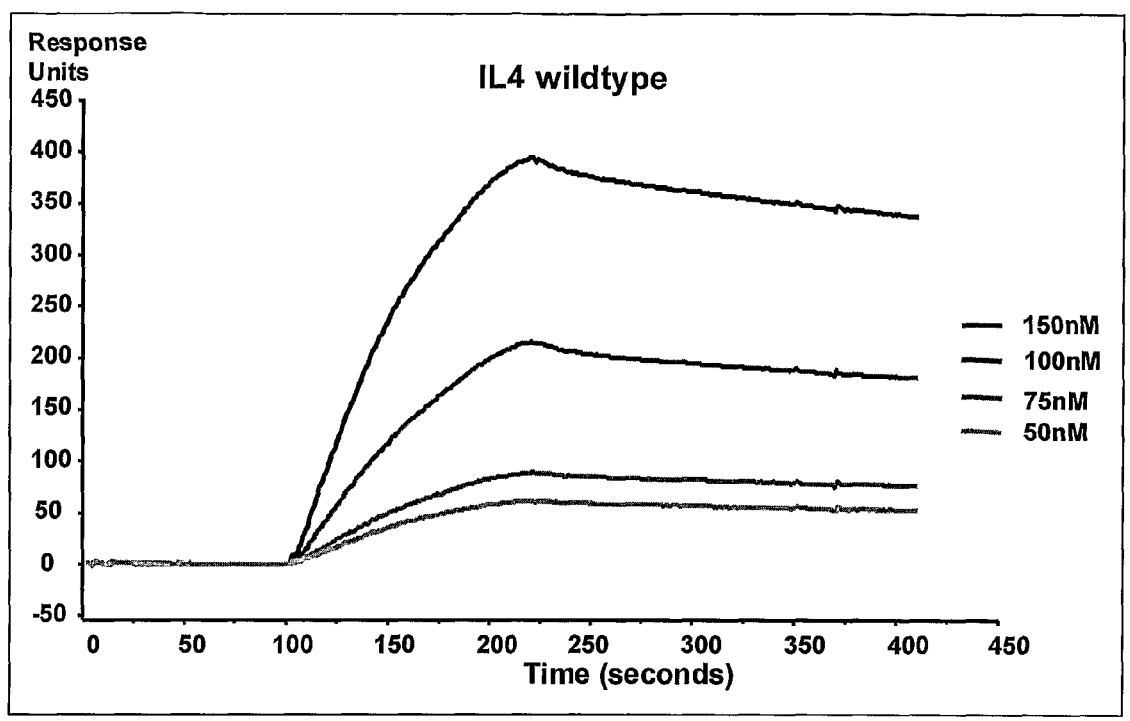

FIG. 24 shows the BIAcore binding curves of wild-type IL-4 binding to heparin immobilised on a biosensor chip. A number of different concentrations of IL-4 are shown. Calculation of the affinity constants indicates an estimated KD in the range of 5-10 nM.

Figure 25:
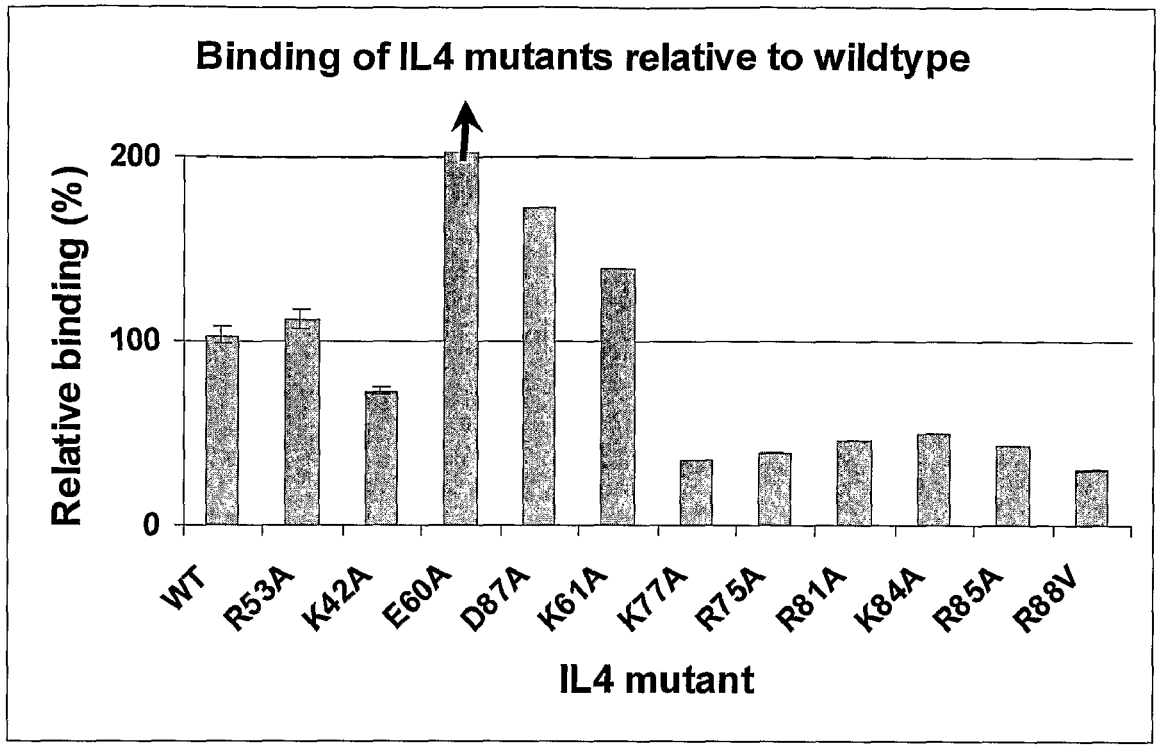

Site directed mutagenesis was performed on IL-4. Basic residues within the proposed heparin binding site were changed to alanine and the proteins expressed using the baculovirus expression system. The one exception was R88 which was changed to valine. Insect cell expressed proteins were purified on an anti-IL-4 affinity column and checked for purity by SDS-PAGE and silver staining. Mutant IL-4 proteins were examined for their ability to bind heparin immobilised on a biosensor chip and binding assessed using a BIAcore 2000. These results, expressed as a % relative binding compared to wild type IL-4 at the same concentration, are presented in FIG. 25. These data suggest that R75, K77, R81, R84, R85 and R88 are part of the heparin binding site on IL-4—this data fits with our molecular modeling predictions.

It is also noteworthy that the E60A mutant displays an increased ability to bind heparin. This may be because removing an acidic residue near to, or in, the binding region which produces a more favourably charged region for heparin binding. The same explanation may also apply to the D87A mutant.

Figure 26:
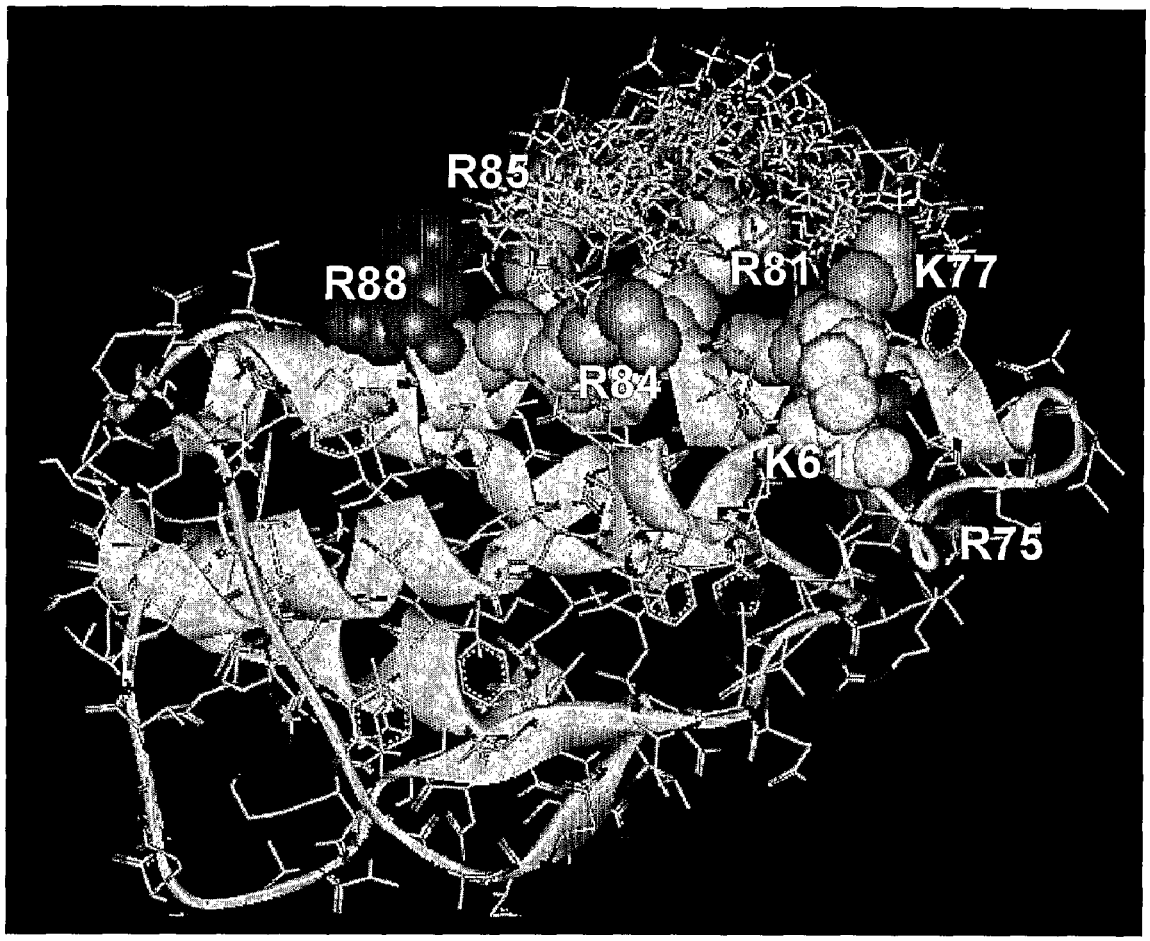

FIG. 26 shows a molecular model of a heparin pentasaccharide, consisting of repeats of the trisulfated disaccharide (Ido2SGlcNS6S), binding to IL-4. The twenty best binding positions are shown. The helical structure of the protein has been displayed and the amino acids believed to contribute to the heparin binding site are indicated as space-filled models.

The modeling of the binding site fits very well with the data obtained from site-directed mutagenesis studies.

In IL-4 the helices are anti-parallel and juxtaposed, (A, C, B, D) with two long end-to-end loops, loop AB and CD which are connected by a short β-sheet located against helices B and D. The binding site for the high-affinity receptor chain IL-4Rα is located on helices A and C, the main binding determinants being E9 and R88 (Wang et al., *Proc Natl Acad Sci USA* 94: 1657-62, 1997). Whereas the binding site for the low affinity receptor chains, γc and IL-13Rα1, is located on helices A and D. The very large contribution of E9 and R88 to the binding of IL-4 to IL-4Rα is because the interacting side chains of both E9 and R88 are surrounded by a shell of minor determinants. The hydrophobic shell around E9 consists of IL-4 residues, 15, K12, T13 and N89 and a set of residues on IL-4Rα and that around R88 consists of R53, Y56 and W91 on IL-4 with a corresponding set of residues on IL-4Rα (Mueller et al., *Biochim Biophys Acta* 1592: 237-50, 2002). The helix AC face of human IL-4 has a large positive charge due to several basic residues namely, K12, R53, R75, K77, R81, K84, R85 and R88. In contrast the binding region on IL-4Rα contains a series of acidic residues. This charge complementarity is believed to steer the association of IL-4 onto IL-4Rα and as a consequence the association rate constant is exceedingly high (Mueller et al., Supra). Our data from the site directed mutagenesis study (FIGS. 25 and 26) indicates that the heparin binding site on IL-4 does overlap with the site involved in binding IL-4Rα. This conclusion is supported by the biological data demonstrating the heparin inhibits IL-4 dependent cell proliferation (FIG. 11).

EXAMPLE 23

Kinetics of IL-4-Heparin-Binding

The kinetics of IL-4-heparin binding indicate a critical role for K77 and R88 (Table 2). R85A produced stronger binding than the wild type (WT) indicating that possibly the bulky arginine is inhibiting binding. R81 and R84 appear also to be important for binding with contributions from K61 and R53. Removing acidic residues: D87 and E60 increases binding. The same is true for E9 but less so. R75 is not orientated towards this face—the increased KD of R75A is possibly due to an altered orientation of other critical amino acids.

A shallow trough involving the C-helix and part of the adjacent B-helix would describe the binding site the heparin binding site on IL-4.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 2

| | Kinetics of IL-4 binding | | |
|---|---|---|---|
| | | Kinetics | |
| | ka | kd | KD (nM) |
| WT | 5.68E+04 | 2.88E−03 | 52.7 |
| E9A | 1.72E+05 | 8.45E−03 | 49.3 |
| K12A | 5.03E+04 | 3.95E−03 | 78.5 |
| K21A | 4.86E+04 | 2.53E−03 | 52.1 |

TABLE 2-continued

Kinetics of IL-4 binding

| | Kinetics | | |
|---|---|---|---|
| | ka | kd | KD (nM) |
| K42A | 4.63E+04 | 2.50E-03 | 53.9 |
| R53A | 5.83E+04 | 5.40E-03 | 92.5 |
| E60A | 8.44E+04 | 2.76E-03 | 32.7 |
| K61A | 4.96E+04 | 3.99E-03 | 80.5 |
| H74A | 2.05E+04 | 6.37E-04 | 31.1 |
| R75A | 3.32E+04 | 3.63E-03 | 109 |
| K77A | 6.42E+03 | 2.24E-03 | 349 |
| R81A | 2.43E+04 | 2.37E-03 | 97.8 |
| K84A | 3.06E+04 | 2.57E-03 | 83.9 |
| R85A | 1.04E+05 | 2.42E-03 | 23.4 |
| D87A | 4.42E+04 | 1.59E-03 | 36 |
| R88V | 1.05E+04 | 3.92E-03 | 372 |
| R121A | 5.13E+04 | 2.13E-03 | 41.5 |
| K77A/K12A | 1.65E+04 | 3.44E-03 | 209 |
| K77A/R53A | 1.79E+04 | 3.08E-03 | 172 |
| K77A/R81A | 9.82E+03 | 1.55E-03 | 158 |
| K77A/K84A | 1.26E+04 | 2.23E-03 | 176 |
| K77A/R85A | 1.51E+04 | 1.78E-03 | 117 |
| K77A/R88V | 1.36E+04 | 1.94E-03 | 142 |

IL-4 mutants were compared with WT for their ability to support the proliferation of TF1.8 cells. Titration curves were performed for each of the mutants and the concentration needed to support 50% of cell growth was determined.

Of the mutants tested E9A and R88V had markedly decreased proliferative activity. A few of the others also had slightly decreased proliferative activity notably R53A and R81A and possibly K84A. Although all mutants bound both a polyclonal and a monoclonal anti-IL-4 antibody some conformational aberrations are still possible. E60A may be in this category.

With the exception of E60A all mutants that have shown reduced activity are known to contribute to the IL-4 receptor alpha (IL-4Ra) binding site. Key residues for IL-4Ra binding are E9 and R88 but these are surrounded by a shell of minor determinants that also contribute (Mueller et al. *Biochim. Biophys. Acta* 1592:237-250, 2002).

The IL-4Ra binding site is described on page 87 of the patent lines 15-20 and our data (sable 3) fit with that which has been published.

TABLE 3

| TF1.8 Bioassay Conc needed for 50% growth | | |
|---|---|---|
| | ng/ml | |
| | average | std dev |
| IL4 wt | 0.99 | 0.22 |
| E9A | 76.1 | 26.7 |
| K12A | 0.6 | 0.21 |
| K21A | 1.36 | 0.18 |
| K42A | 0.67 | 0.25 |
| R53A | 9.39 | 0.87 |
| E60A | 19.37 | 3.09 |
| K61A | 2.4 | 0.57 |
| R75A | 0.63 | 0.13 |
| K77A | 1.55 | 0.37 |
| R81A | 4.85 | 1.25 |
| K84A | 2.95 | 0 |
| R85A | 0.71 | 0.23 |
| R88V | 415 | 87 |
| R121A | 1.01 | 0.34 |
| K77A/K84A | 1.69 | 0.56 |

TABLE 3-continued

| TF1.8 Bioassay Conc needed for 50% growth | | |
|---|---|---|
| | ng/ml | |
| | average | std dev |
| K77A/R53A | 11.3 | 1.04 |
| K77A/R81A | 1.65 | 0.25 |

BIBLIOGRAPHY

Alban and Franz, *Biomacromolecules* 2: 354-361, 2001

Baumann et al., *Carbohydr. Res.* 308: 381-388. 1998

Cardin and Weintraub, *Arteriosclerosis* 9: 21-32, 1989

Casu, *Adv. Carbohydr. Chem. Biochem.* 43: 51-134, 1985

Casu, *Ann. N.Y. Acad. Sci.* 556: 1-17, 1989

Chai et al., *Anal. Chem.* 70(10): 2060-2066, 1998

Chuang et al., *Biochemistry* 39: 3542-3555, 2000

Conrad, Heparin binding proteins. Academic Press, San Diego, 1998

Coombe et al., *Journal of Immunological Methods* 215: 145-150, 1998

Delehedde, *J. Biol. Chem.* 277(14): 12456-12462, 2002

Doullard and Hoffman, Basic Facts about Hybridomas, in *Compendium of Immunology* Vol. II, ed. by Schwartz, 1981

Dubreuil et al., *Tetrahedron* 55: 7573-7582, 1999

Eckert and Kim, *Annu. Rev. Biochem.* 70: 777-810, 2001

Faham et al., *Science* 271: 1116-1120, 1996

Finke et al., *J. Bacteriol* 173: 4088-4094, 1991

Hileman et al., *Bioessays* 20: 156-67, 1998

Hirano et al., *Chitin. Nat. Tecnool, [Proc. Int. Conf. Chitin Chitosan],* 3rd Ed., (Pub 1986) 416-468, 1985

Horowitz et al., *Chitin, Chitosan and related enzymes*, Zikakis J., (ed)., Academic Press, Orlando, Fla., 1984;

Kohler and Milstein, *Nature* 256: 495-499, 1975

Kohler and Milstein, *European Journal of Immunology* 6: 511-519, 1976

Lander and Selleck, *J. Cell Biol.* 148(2): 227-232, 2000

Leali et al., *J. Biol. Chem.* 276: 37900-37908, 2001

Lidholt et al., *J. Biol. Chem.* 272: 2682-2387, 1997

Liu et al., *J. Biol. Chem.* 274: 38155-38162, 1999

Lyon et al., *J. Biol. Chem.* 269: 11216-11223, 1994

Lyon et al., *J. Biol. Chem.* 277(2): 1040-1046, 2002;

Maccarana et al., *J. Biol. Chem.* 268(32): 23898-23905, 1993

Milburn et al., *Nature* 363: 172-176, 1993

Money and York, *Cardiovascular Surgery* 9: 211-218, 2001

Moon et al., *J. Biol. Chem.* 279: 45185-45193, 2002

Mueller et al., *Brochim Biophys Acta* 1592: 237-50, 2002

Muller and Randolph, *Journal of Leukocyte Biology* 66: 698-704, 1999

Mulloy and Forster, *Glycobiology* 10: 1147-56, 2000

Nader et al., *Glyconjugate Journal.* 16: 265-270, 1999

Nicola, In: Guidebook to cytokines and their receptors, Ed. N. A. Nicola, Oxford University Press, Oxford, U.K., 1994

Ogamo et al., *Carbohydr. Res.* 193: 165-172, 1989

Petitou et al., *Nature* 398: 417-422, 1999

Rainger et al., *Thromb. Haemost.* 79: 1177-1183, 1998

Sasisekharan and Venkataraman, *Curr. Opin. Chem. Biol.* 4(6): 626-631, 2000

Scibek et al., *Anal Biochem* 307: 258-65, 2002

Shaklee and Conrad, *Biochem. J.* 271:187-197, 1984

Shaklee and Conrad, *Biochem. J.* 235:225-236, 1986

Shively and Conrad, *Biochemistry* 15:3932-39, 1976

Tavernier et al., *Proc Natl Acad Sci USA* 92: 5194-8, 1995

Terbojevich et al., *Makromol. Chem.* 190: 2847-2855, 1989

Tsiang et al., *J. Biol. Chem.* 270: 16854-16863, 1995
Turnbull et al., *Proc. Natl. Acad. Sci. USA* 96(6): 2698-2703, 1999
Varon et al., *Blood* 91: 500-507, 1998
Venkatarman et al., *Science* 286(5439): 537-542, 1999
Vieira de Almeida et al., *Tetrahedron* 55: 7251-7270, 1999
Wang et al., *Proc Natl Acad Sci USA* 94: 1657-62, 1997
Whisstock et al., *J. Mol. Biol.* 301: 1287-1305, 2000
Wu et al., *J. Biol Chem* 274: 20479-88, 1999

The invention claimed is:

1. A method of identifying a molecule as a candidate for treatment of inflammatory disease, comprising identifying a molecule that interacts with a three dimensional site on IL-5 comprising amino acid residues R32, R67, K70, K76, K77, K83, K84, K85, E88, E89, R90, R91 and R92, wherein the molecule is a candidate for treatment of inflammatory disease if it interacts with said three dimensional site.

* * * * *